US007794945B2

(12) United States Patent
Hedgpeth et al.

(10) Patent No.: US 7,794,945 B2
(45) Date of Patent: *Sep. 14, 2010

(54) HYBRIDIZATION AND MISMATCH DISCRIMINATION USING OLIGONUCLEOTIDES CONJUGATED TO MINOR GROOVE BINDERS

(75) Inventors: Joel Hedgpeth, San Francisco, CA (US); Irina A. Afonina, Mill Creek, WA (US); Igor V. Kutyavin, Bothell, WA (US); Eugeny A. Lukhtanov, Bothell, WA (US); Evgeniy S. Belousov, Mill Creek, WA (US); Rich B. Meyer, Jr., Bothell, WA (US)

(73) Assignee: Elitech Holding B.V. (NL)

( * ) Notice: Subject to any disclaimer, the term of this patent is extended or adjusted under 35 U.S.C. 154(b) by 3 days.

This patent is subject to a terminal disclaimer.

(21) Appl. No.: 12/172,999

(22) Filed: Jul. 14, 2008

(65) Prior Publication Data

US 2009/0048427 A1    Feb. 19, 2009

Related U.S. Application Data

(60) Continuation of application No. 11/784,539, filed on Apr. 6, 2007, now Pat. No. 7,556,923, which is a continuation of application No. 10/870,578, filed on Jun. 16, 2004, now abandoned, which is a continuation of application No. 10/127,936, filed on Apr. 22, 2002, now Pat. No. 6,884,584, which is a continuation of application No. 09/640,953, filed on Aug. 16, 2000, now Pat. No. 6,492,346, which is a division of application No. 09/054,832, filed on Apr. 3, 1998, now Pat. No. 6,312,894, which is a continuation of application No. 08/415,370, filed on Apr. 3, 1995, now Pat. No. 5,801,155.

(51) Int. Cl.
   C12Q 1/68   (2006.01)
   C07H 21/02  (2006.01)
   C07H 21/04  (2006.01)

(52) U.S. Cl. .................... 435/6; 536/23.1; 536/24.3
(58) Field of Classification Search .............. 435/6; 536/23.1, 24.3
See application file for complete search history.

(56) References Cited

U.S. PATENT DOCUMENTS

| | | | |
|---|---|---|---|
| 4,358,535 A | 11/1982 | Falkow et al. | |
| 4,458,066 A | 7/1984 | Caruthers | |
| 4,683,195 A | 7/1987 | Mullis et al. | |
| 4,683,202 A | 7/1987 | Mullis | |
| 4,800,159 A | 1/1989 | Mullis et al. | |
| 4,835,263 A | 5/1989 | Nguyen et al. | |
| 4,868,103 A | 9/1989 | Stavrianopoulos et al. | |
| 4,868,105 A | 9/1989 | Urdea et al. | |
| 4,883,750 A | 11/1989 | Whiteley et al. | |
| 5,124,246 A | 6/1992 | Urdea et al. | |
| 5,210,015 A | 5/1993 | Gelfand et al. | |
| 5,237,101 A | 8/1993 | Nicolaou et al. | |
| 5,419,966 A | 5/1995 | Reed et al. | |
| 5,446,137 A | 8/1995 | Maag et al. | |
| 5,449,767 A | 9/1995 | Ward et al. | |
| 5,492,806 A | 2/1996 | Drmanac et al. | |
| 5,512,667 A | 4/1996 | Reed et al. | |
| 5,525,464 A | 6/1996 | Drmanac et al. | |
| 5,556,752 A | 9/1996 | Lockhart et al. | |
| 5,574,142 A | 11/1996 | Meyer, Jr. et al. | |
| 5,646,126 A | 7/1997 | Cheng et al. | |
| 5,659,022 A | 8/1997 | Kutyavin et al. | |
| 5,776,907 A | 7/1998 | Kohn et al. | |
| 5,786,138 A | 7/1998 | Swenson | |
| 5,801,155 A | 9/1998 | Kutyavin et al. | |
| 6,492,346 B1 * | 12/2002 | Hedgpeth et al. | ......... 514/44 R |

FOREIGN PATENT DOCUMENTS

| | | |
|---|---|---|
| EP | 070685 | 10/1985 |
| EP | 320308 B1 | 11/1993 |
| EP | 336731 B1 | 5/1994 |
| WO | WO 90/03370 | 4/1990 |
| WO | WO 90/14353 | 11/1990 |
| WO | WO 92/10588 | 6/1992 |
| WO | WO 92/20698 | 11/1992 |
| WO | WO 93/03736 | 3/1993 |
| WO | WO 94/17092 | 8/1994 |
| WO | WO 95/29184 | 11/1995 |

(Continued)

OTHER PUBLICATIONS

Afonina et al., "Sequence-specific arrest of primer extension on single-stranded DNA by an oligonulcleotide-minor groove binder conjugate," Proc. Natl. Acad. Sci. USA, vol. 93:3199-3204 (1996).

(Continued)

Primary Examiner—Ethan Whisenant
(74) Attorney, Agent, or Firm—Jackson Walker L.L.P.

(57) ABSTRACT

Conjugates between a minor groove binding molecule, such as the trimer of 1,2-dihydro-(3H)-pyrrolo[3,2-e]indole-7-carboxylate ($CDPI_3$), and an oligonucleotide form unusually stable hybrids with complementary target sequences, in which the tethered $CDPI_3$ group resides in the minor groove of the duplex. These conjugates can be used as probes and primers. Due to their unusually high binding affinity, conjugates as short as 8-mers can be used as amplification primers with high specificity and efficiency. MGB conjugation also increases the discriminatory power of short oligonucleotides, providing enhanced detection of nucleotide sequence mismatches by short oligonucleotides. The MGB-conjugated probes and primers described herein facilitate various analytic and diagnostic procedures, such as amplification reactions, PCR, detection of single-nucleotide polymorphisms, gene hunting, differential display, fluorescence energy transfer, hydrolyzable probe assays and others; by allowing the use of shorter oligonucleotides, which have higher specificity and better discriminatory power.

5 Claims, 5 Drawing Sheets

FOREIGN PATENT DOCUMENTS

| | | |
|---|---|---|
| WO | WO 96/17957 | 6/1996 |
| WO | WO 96/32496 | 10/1996 |
| WO | WO 96/40711 | 12/1996 |
| WO | WO 97/12896 | 4/1997 |
| WO | WO 98/02448 | 1/1998 |

OTHER PUBLICATIONS

Agrawal et al., "Pharmacokinectics, biodistribution, and stability of oligodeoxynucleotide phosphorothioates in mice," Proc. Natl. Acad. Sci. USA, vol. 88:7595-7599 (1991).

Animati et al., "Synthesis of Two Distamycin Analogues and Their Binding Mode to d(CGCAAATTTGCG)$_2$ in the 2:1 Solution Complexes as Determined by Two Dimensional $^1$H-NMR," J. Med. Chem., vol. 38:1140-1149 (1995).

Asseline et al., "Nucleic acid-binding molecules with high affinity and base sequence specificity: Interacting agents covalently linked to oligodeoxynucleotides," Proc. Natl. Acad. Sci. USA, vol. 81:3297-3301 (1984).

Atkinson T., and Smith M., "Solid-phase Synthesis of Oligodeoxyribonucleotides by the Phosphite-triester Method," In *Oligonucleotide Synthesis, A Practical Approach*, M.J. Gait, ed., IRL Press, Oxford, UK, pp. 35-81 (1984).

Boger et al., "Studies on the Total Synthesis of CC-1065: Preparation of a Synthetic, Simplified 3-Carbamoyl-1,2-dihydro-3H-pyrrolo[3,2-e]indole Dimer/Trimer/Tetramer (CDPI Dimer/Trimer/Tetramer) and Development of Methodology for PDE-I Dimer Methyl Ester Formation," J. Org. Chem., vol. 52:1521-1530 (1987).

Boger et al., "CC-1065 Partial Structures: Enhancement of Noncovalent Affinity for DNA Minor Groove Binding through Introduction of Stabilizing Electrostatic Interactions," J. Org. Chem., vol. 57:1277-1284 (1992).

Boger et al., "CC-1065 and the duocarmycins: Unraveling the keys to a new class of naturally derived DNA alkylating agents," Proc. Natl. Acad. Sci. USA, vol. 92:3642-3649 (1995).

Bolli et al., "Watson-Crick base-pairing properties of bicyclo-DNA," Nucleic Acids Res., vol. 24:4660-4667 (1996).

Caetano-Anolles et al., "DNA Amplification Fingerprinting Using Very Short Arbitrary Oligonucleotide Primers," Biotechnology, vol. 9:553-557 (1991).

Cardullo et al., "Detection of nucleic acid hybridization by nonradiative fluorescence resonance energy transfer," Proc. Natl. Acad. Sci. USA, vol. 85:8790-8794 (1988).

Chen et al., "A New DNA Minor Groove Binding Motif: Cross-Linked Lexitropsins," J. Am Chem. Soc., vol. 116:6995-7005 (1994).

Cosstick et al., "Synthesis of d(GC) and d(CG) Octamers Containing Alternating Phosphorothioate Linkages: Effect of the Phosphorothioate Group on the B-Z Transiton," Biochemistry, vol. 24:3630-3638 (1985).

Demidov et al., "Kinetics and mechanism of polyamide ("peptide") nucleic acid binding to duplex DNA," Proc. Natl. Acad. Sci. USA, vol. 92:2637-2641 (1995).

Dempcy et al., "Synthesis of a thymidyl pentamer of deoxyribonucleic guanidine and binding studies with DNA homopolynucleotides," Proc. Natl. Acad. Sci. USA, vol. 92:6097-6101 (1995).

Don et al., "'Touchdown' PCR to circumvent spurious priming during gene amplification," Nucleic Acids Res., vol. 19:4008 (1991).

Draper et al., "A Method for Linking Fluorescent Labels—to Polynucleotides: Application to Studies of Ribosome-Ribonucleic Acid Interactions," Biochemistry, vol. 19:1774-1781 (1980).

Eckstein et al., "Polyribonucleotides Containing a Phosphorothioate Backbone," Eur. J. Biochem., vol. 13:558-564 (1970).

Fagan et al., Cooperative Binding of Distamycin-A to DNA in the 2:1 Mode, J. Am Chem. Soc., vol. 114:1080-1081 (1992).

Freifelder, "Fluorescence Spectroscopy," Physical Biochemistry, Second Edition, W.H. Freeman & Co., San Francisco pp. 537-542 (1982).

Gamper et al., "Facile preparation of nuclease resistant 3' modified oligodeoxynucleotides," Nucleic Acids Res., vol. 21(1):145-150 (1993).

Gibson K.J. & Benkovic, S.J.., "Synthesis and application of derivatizable oligonucleotides," Nucleic Acids Res., vol. 15:6455-6467 (1987).

Giovannangeli et al., "Oligonucleotide clamps arrest DNA synthesis on a single-stranded DNA target," Proc. Natl. Acad. Sci. USA, vol. 90:10013-10017 (1993).

Godovikova et al., "Reactive Oligonucleotide Derivatives with a Zwitter-Ionic Terminal Phosphate Group for Affinity Reagents and Probe Construction," Bioorgan. Khim., vol. 15:1246-1259 (1989).

Grehn L., et al., "Novel Efficient Total Synthesis of Antiviral Antibiotic Distamycin A," J. Org. Chem., vol. 46:3492-3497 (1981).

Gryaznov et al., "Oligodeoxyribonucleotide N3'→P5' Phosphoramidates: Synthesis and Hybridization Properties," J. Am Chem. Soc., vol. 116:3143-3144 (1994).

Gryaznov et al., "Modulation of oligonuceotide duplex and triplex stability via hydrophobic interactions," Nucleic Acids Res., vol. 21(25):5909-5915 (1993).

Heid et al., "Real Time Quantitative PCR," Genome Res., vol. 6:986-994 (1996).

Huang et al., "Diagnosis of Glucose-6-Phosphate Dehydrogenase (G6PD) Mutations by DNA Amplification and Allele-Specific Oligonucleotide Probes," Acta Haematol., vol. 88:92-95 (1992).

Hurley et al., "Reaction of the Antitumor Antibiotic CC-1065 with DNA: Structure of a DNA Adduct with DNA Sequence Specificity," Science, vol. 226:843-844 (1984).

Inoue et al., "Synthesis and hybridization studies on two complementary nona(2'-O-methyl)ribonucleotides," Nucleic acids Res., vol. 15(15):6131-6148 (1987).

Jones, "Preparation of protected deoxyribonucleotides," in *Oligonucleotide Synthesis, A Practical Approach*, M.J. Gait, ed., IRL Press, Oxford, UK, pp. 23-34 (1984).

Jost et al., "Quantitative precipitation of short oligonucleotides with low concentrations of cetyltrimethylammonium bromide," Nucleic Acids Res., vol. 17(5):2143 (1989).

Kazimierczuk et al., "Synthesis of 2'-Deoxytubercidin, 2'-Deoxyadenosine, and Related 2'-Deoxynuclesides via a Novel Direct Stereospecific Sodium Salt Glycosylation Procedure," J. Am Chem. Soc., vol. 106:6379-6382 (1984).

Kessler (ed.), *Nonradioactive Labeling and Detection of Biomolecules*, Springer-Verlag, Berlin, pp. 13-14 (1992).

Kim et al., "Helix-Stabilizing Compounds CC-1065 and U-71,184 Bind to RNA-DNA and DNA-DNA Duplexes Containing Modified Internucleotide Linkages and Stabilize Duplexes Against Thermal Melting," Antisense Res. Dev., vol. 5:49-57 (1995).

Kim et al., "Helix-Stabilizing Agent, CC-1065, Enhances Suppression of Translation by an Antisense Oligodeoxynucleotide," Antisense Research and Development, vol. 5:149-154 (1995).

Kubista et al., "Characterization of Interaction between DNA and 4',6-Diamidino-2-phenylindole by Optical Spectroscopy," Biochemistry, vol. 26:4545-4553 (1987).

Lamm et al., "Antisense probes containing 2-aminoadenosine allow efficient depletion of U5 snRNP from HeLa splicing extracts," Nucleic Acids Res., vol. 19(12):3193-3198 (1991).

LaPlanche et al., "Phosphorothioate-modified oligodeoxyribonucleotides. III. NMR and UV spectroscopic studies of the $R_p$-$R_p$, $S_p$-$S_p$, and $R_p$-$S_p$ duplexes, [d(GG$_s$AATTCC)$_2$, derived from diasteromeric O-ethyl phosphorothioates," Nucleic Acids Res., vol. 14(22):9081-9093 (1986).

Larhammar et al., "Exon-intron organization and complete nucleotide sequence of a human major histocompatibility antigen DCβ gene," Proc. Natl. Acad. Sci. USA, vol. 80:7313-7317 (1983).

Lee et al., "Mapping of DNA Alkylation Sites Induced by Adozelesin and Bizelesin in Human Cells by Ligation-Mediated Polymerase Chain Reaction," Biochemistry, vol. 33:6024-6030 (1994).

Liang et al., "Differential Display of Eukaryotic Messenger RNA by Means of the Polymerase Chain Reaction," Science, vol. 257:967-971 (1992).

Livak et al., Oligonucleotides with Fluorescent Dyes at Opposite Ends Provide a Quenched Probe System Useful for Detecting PCR Product and Nucleic Acid Hybridization, PCR Meth. and App., vol. 4:357-362 (1995).

Lokhov et al., "Synthesis and high stability of complementary complexes of N-(2-Hydroxyethyl)phenazinium derivatives of oligonucleotides," Bioconjugate Chem., vol. 3:414-419 1992).

Lukhtanov et al., "Oligodeoxyribonucleotides with Conjugated Dihydropyrroloindole Oligopeptides: Preparation and Hybridization Properties," Bioconjugate Chem., vol. 6:418-426 (1995).

Lukhtanov et al., "Direct, Solid Phase Assembly of Dihydropyrroloindole Peptides with Conjugated Oligonucleotides," Bioconjugate Chem., vol. 7:564-567 (1996).

Marck et al., "Specific interaction of netropsin, distamycin-3 and analogs with I.C duplexes: reversion towards the B form of the 2'deoxy-.2'deoxy-2'-fluoro-hybrid duplexes upon specific interaction with netropsin, distamycin-3 and analogs,:" Nucleic Acids Res., vol. 10(19):6147-6161 (1982).

Mohan et al., "Flexibility of DNA In 2:1 Drug-DNA Complexes-Simultaneous Binding of Two DAPI Molecules to DNA," J. Biomol. Struct. Dyn., vol. 9(3):695-704 (1991).

Monia et al., "Evaluation of 2'-Modified Oligonucleotides Containing 2'-Deoxy Gaps as Antisense Inibitors of Gene Expression," J. Biol. Chem., vol. 268(19):14514-14522 (1993).

Moon et al., "DNA Structural Features Responsible for Sequence-Dependent Binding Geometries of Hoescht 33258," Biopolymers, vol. 38:593-606 (1996).

Mrksich et al., "Antiparallel side-by-side dimeric motif for sequence-specific recognition in the minor groove of DNA by the designed peptide 1-methylimidazole-2-carboxamide netropsin," Proc. Natl. Acad. Sci. USA, vol. 89:7586-7590 (1992).

Mullis and Faloona, "Specific Synthesis of DNA in Vitro via a Polymerase-Catalyzed Chain Reaction," Meth. Enzymol., vol. 155:335-50, Academic Press, New York (1987).

Nielsen et al., "Sequence-Selective Recognition of DNA by Strand Displacement with a Thymine-Substituted Polyamide," Science, vol. 254:1497-1500 (1991).

Nielsen et al., "Peptide Nucleic Acid (PNA). A DNA Mimic with a Peptide Backbone," Bioconjugate Chem., vol. 5:3-7 (1994).

ørum et al. "Single base pair mutation analysis by PNA directed PCR clamping," Nucleic Acid Research, vol. 21(23):5332-5336 (1993).

Parris et al., "A signature element distinguishes sibling and independent mutations in a shuttle vector plasmid," Gene, vol. 117:1-5 (1992).

Petrie et al., "An Improved CPG Support for the Synthesis of 3'-Amine-Tailed Oligonucleotides," Bioconugate Chemistry, vol. 3:85-87 (1992).

Rao et al., "Synthesis of novel thiazole-containing DNA minor groove binding oligopeptides related to the anitbiotic distamycin," J. Org. Chem., vol. 55:728-737 (1990).

Reed et al., "Acridine- and Cholesterol-Derivatized Solid Supports for Imporved Synthesis of 3' -Modified Oligonucleotides," Bioconjugate Chem., vol. 2:217-225 (1991).

Reynolds et al., "Reaction of the Antitumor Antibiotic CC-1065 with DNA. Location of the Site of Thermally Induced Strand Breakage and Analysis of DNA Sequence Specificity," Biochemistry, vol. 24:6228-6237 (1985).

Robins et al., "Nucleic acid related compounds. 38. Smooth and high-yield iodination and chlorination at C-5 of uracil bases and p-toluyl-protected nucleosides," Can. J. Chem., vol. 60:554-557 (1982).

Robins et al., "Nucleic acid Related Compounds. 39. Efficient Conversion of 5-Iodo to 5-Alkynyl and Derived 5-Substituted-Uracil Base and Nucleosides," J. Org. Chem., vol. 48:1854-1862 (1983).

Rougeon et al., "Insertion of a rabbit β-globin gene sequence into an E. coli plasmid," Nucleic Acids Res, vol. 2(12):2365-2378 (1975).

Saiki et al., "Enzymatic Amplification of β-Globin Genomic Sequences and Restriction Site Analysis for Diagnosis of Sickle Cell Anemia," Science, vol. 230:1350-1354 (1985).

Saiki, Chapter 1: The Design and Optimization of the PCR, In Erlich, H.A. (ed.), *PCR Technology: Principles and Applications for DNA Amplification*. Stockton Press, pp. 7-16 (1989).

Sanger et al., "DNA sequencing with chain-terminating inhibitors," Proc. Natl. Acad. Sci. USA., vol. 74:5463-5467 (1977).

Scahill et al., "An NMR Study of the Covalent and Noncovalent Interactions of CC-1065 and DNA," Biochemistry, vol. 29:2852-2860 (1990).

Schaeffer et al., "DNA variation and the future of human genetics," Nature Biotechnology, vol. 16:33-39 (1998).

Shabarova et al., "DNA-like duplexes with repetitions. III. Efficient template-guided chemical polymerization of d(TGGCCAAGCTp)," Nucleic Acids Res., vol. 9:5747-5761(1981).

Sinyakov et al., "Exceptional and Selective Stabilization of A-T Rich DNA-DNA Duplexes by N-Methylpyrrole Carboxamide Peptides Conjugated to Oligodeoxynucleotides," J. Am Chem. Soc., vol. 117:4995-4996(1995).

Smits et al., "Detection and typing of human papillomaviruses present in fixed and stained archival cervical smears by a consensus polymerase chain reaction and direct sequence analysis allow the identification of a broad spectrum of human papillomavirus types," J. Gen. Virol., vol. 73:3263-3268 (1992).

Sproat et al., "2'-O-Alkyloligoribonucleotides." In Crooke, S.T. and Lebleu, B. (eds), *Antisense Research and Applications*, CRC Press, Boca Raton, FL., pp. 351-362 (1993).

Sonveaux, "The Organic Chemistry Underlying DNA Synthesis," Bioinorganic Chemistry, vol. 14:274-325 (1986).

Stein et al., "Physiochemical properties of phosphorothioate oligodeoxynucleotides," Nucleic Acids Res., vol. 16(8):3209-3221(1988).

Suggs et al., "Evidence for sequence-specific conformational changes in DNA from the melting temperatures of DNA phosphorothioate derivates," Nucleic Acids Res., vol. 13(15):5707-1716 (1985).

Tabone et al., "Factors influencing the extent and regiospecificity of cross-link formation between single stranded DNA and reactive complementary oligodeoxynucleotides," Biochemistry, vol. 33: 375-383 (1994).

Tautz, "Notes on the definition and nomenclature of tandemly repetitive DNA sequences," in *DNA Fingerprinting: State of the Science*, Pena et al., ed., Birkhauser, Basel, pp. 21-28 (1993).

Tung et al., Chapter 9: PCR Amplification of Specific Sequences from a cDNA Library, In Erlich, H.A. (ed.), *PCR Technology: Principles and Applications for DNA Amplification*, Stockton press, pp. 99-104 (1989).

van Ness et al., "The use of oligodeoxynucleotide probes in chaotrope-based hybridization solutions," Nucleic Acids Res., vol. 19:5143-5151 (1991).

Wagner et al., "Antisense Gene Inhibition by Oligonucleotides Containing C-5 Propyne Pyrimidines," Science, vol. 260:1510-1513 (1993).

Wartell et al., "Netropsin: A Specific Probe for A-T Regions of Duplex Deoxyribonucleic Acid," J. Biol. Chem., vol. 249(21):6719-6731 (1974).

Webb, et al., "Hybridization triggered cross-linking of deoxyoligonucleotides," Nucleic Acids Res., vol. 14:7661-7674 (1986a).

Webb, et al.; "Seqtience-Specific Cross-Linking of Deoxyoligonucleotides via Hybridization-Triggered Alkylation," J. Am Chem. Soc., vol. 108:2764-2765 (1986b).

Wiederholt et al., "Oligonucleotides Tethering Hoechst 33258 Derivatives: Effect of the Conjugation Site on Duplex Stabilzation and Fluorescence Properties," Bioconjugate Chem., vol. 8:119-126 (1997).

Wiederholt et at, "DNA-Tethered Hoechst Groove-Binding Agents: Duplex Stabilzation and Fluorescence Chararcteristics," J. Am Chem. Soc., vol. 118:7055-7062 (1996).

Williams et al., "Genetic Analysis Using Random Amplified Polymorphic DNA Markers," *In Methods in Enzymology, vol. 218 Recombinant DNA Part I*, Academic Press, New York, pp. 704-740 (1993).

Wittwer et al., "Continuous Fluorescence Monitoring of Rapid Cycle DNA Amplification," Biotechniques, vol. 22(1):130-138 (1997a).

Wittwer et al., "The LightCyler™: A Microvolume Multisample Fluorimeter with Rapid Temperature Control," Biotechniques, vol. 22(1):176-181(1997a).

Afonina et al. (1997) "Efficient priming of PCR with short oligonucleotides conjugated to a minor groove binder," *Nucleic Acids Res.* 25(13):2657-2660.

Bailly et al. (Nov./Dec. 1991). "DNA Recognition by Intercalator-Minor-Groove Binder Hybrid Molecules," *Bioconjugate Chem.* 2(6):379-393.

Greenidge et al. (1993). "DNA Minor Groove Recognition Properties of Pentamidine and its Analogs: A Molecular Modeling Study," *Molecular Pharmacology*. 43:982-988.

Turner et al. (1996). "The mutagenic properties of DNA minor-groove binding ligands," *Mutation Research*. 355:141-169.

Wemmer et al. (1997). "Targeting the minor groove of DNA," *Structural Biology* 7:355-361.

* cited by examiner

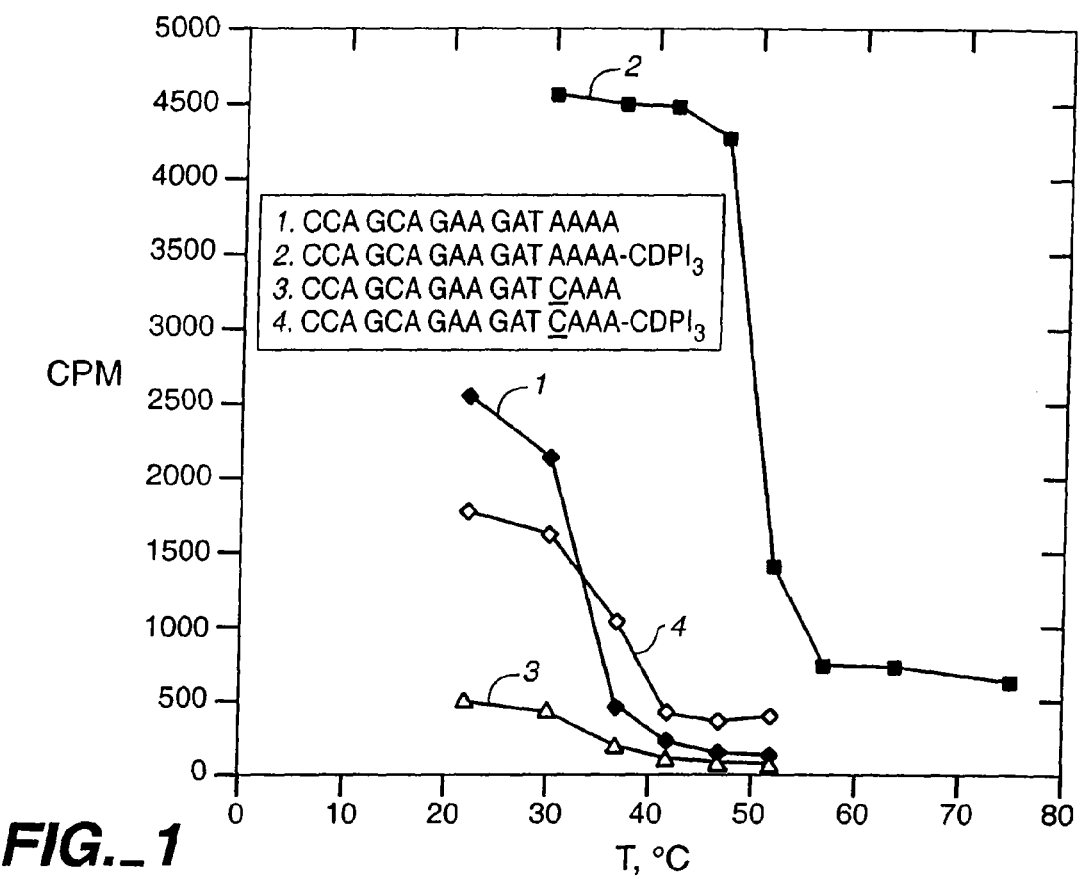
FIG._1
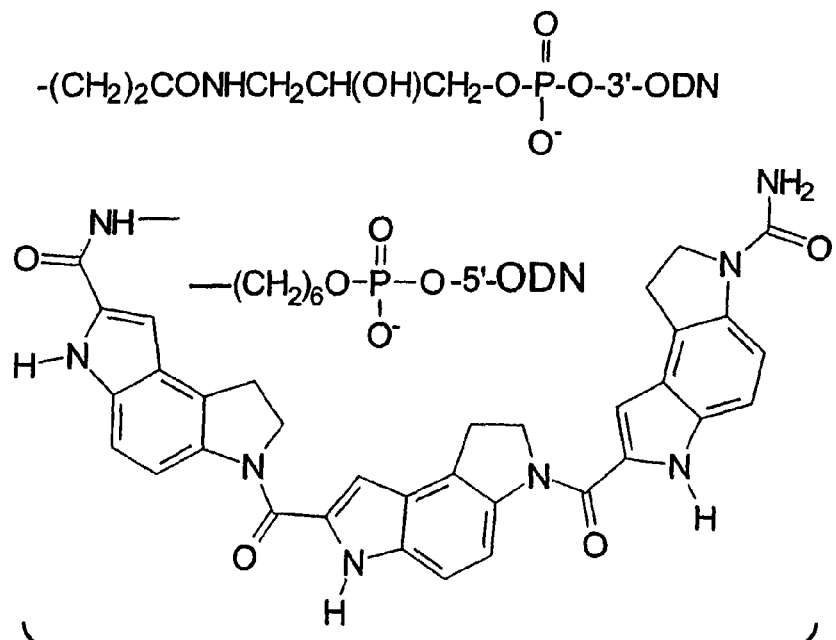
FIG._2

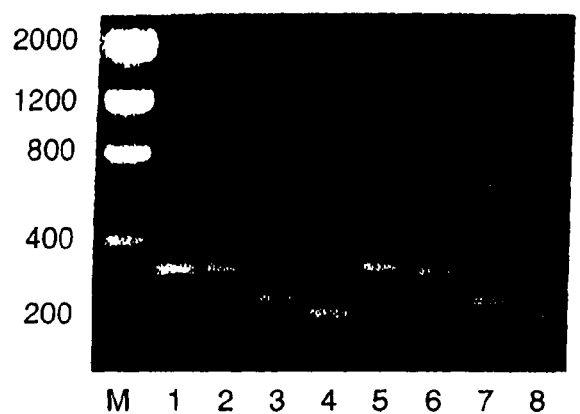
FIG._3A
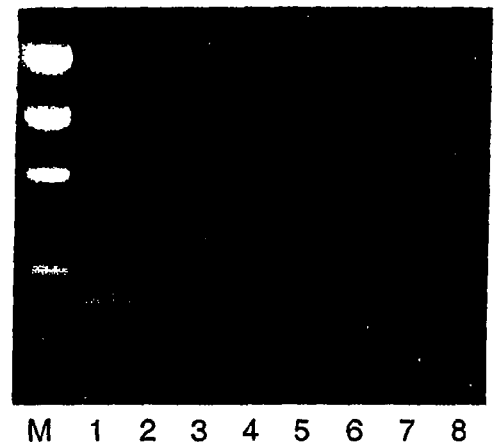
FIG._3B
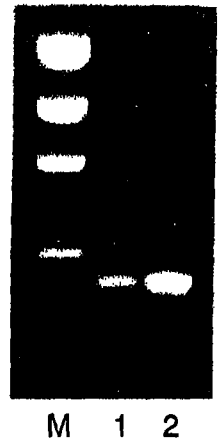
FIG._3C

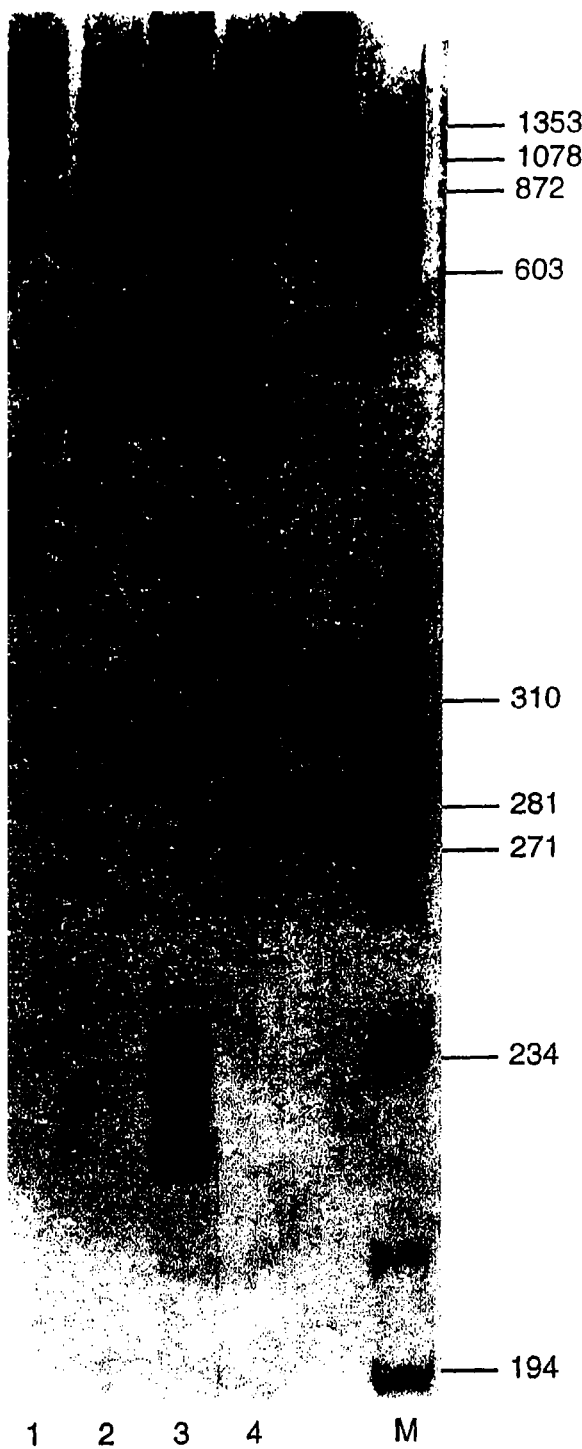
FIG._4A
FIG._4B

```
                                                                        PRIMER 1
4741 AAAACTCTCA AGGATCTTAC CGCTGTTGAG ATCCAGTTCG ATGTAACCCA CTCGTGCACC

4801 CAACTGATCT TCAGCATCTT TTACTTTCAC CAGCGTTTCT GGGTGAGCAA AAACAGGAAG

4861 GCAAAATGCC GCAAAAAAGG GAATAAGGGC GACACGGAAA TGTTGAATAC TCATACTCTT

SUPF NUCLEOTIDE 1         11
4921 CCTTTTTCAA TATTATTGAA GCATTTATCA GG          GAATTCGAGA GCCCTGCTCG

18-MER
                  15-MER
        21        12-MER
        AGCTGTGGTG GGGTTCCCGA GCGGCCAAAG GGAGCAGACT CTAAATCTGC CGTCATCGAC
             32  A
             36     T
             36     G
             36     A
             37       T
             37       A
             39         C
             41            A
             41            C
             43               A
             43               T
             44                 T

81
    TTCGAAGGTT CGAATCCTTC CCCCACCACC ACGGCCGAAA TTCGGTACCC GGATCCTTAG

141
    CGAAAGCTAA GATTTTTTTT ACGCGTGAGC TCGACTGACT CCNNNNNNNN GAGCTCAATT

201                                                        PRIMER 2
    CGGTCGAGGT CGGGCCGCGT TGCTGGCGTT TTTCCATAGG CTCCCCCCCC CTGACGAGCA

261
        TCACAAAAAT CGACGCTCAA GTCAGAGGTG GCGAAACC
```

FIG. 5

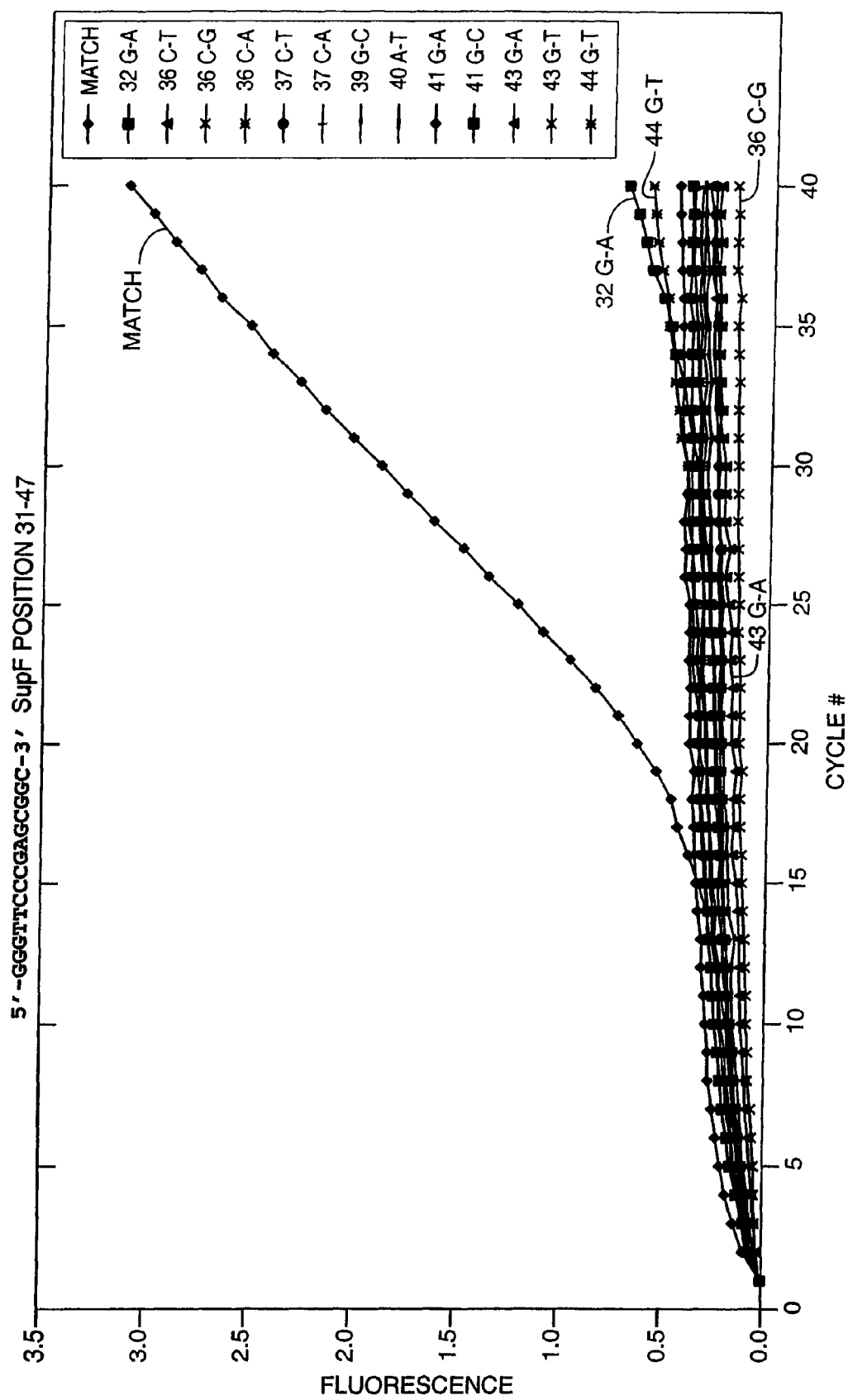
FIG._6

HYBRIDIZATION AND MISMATCH DISCRIMINATION USING OLIGONUCLEOTIDES CONJUGATED TO MINOR GROOVE BINDERS

CROSS-REFERENCE TO RELATED APPLICATIONS

This application is a continuation of U.S. patent application Ser. No. 11/784,539 (filed Apr. 6, 2007), which is a continuation of U.S. patent application Ser. No. 10/870,578 (filed Jun. 16, 2004), which is a continuation of U.S. patent application Ser. No. 10/127,936 (filed Apr. 22, 2002), which is a continuation of U.S. patent application Ser. No. 09/640,953 (filed Aug. 16, 2000, now U.S. Pat. No. 6,492,346, which is a division of U.S. patent application Ser. No. 09/954,832 (filed Apr. 3, 1998), now U.S. Pat. No. 6,312,894, which is a continuation-in-part of U.S. patent application Ser. No. 08/415,370 (filed Apr. 3, 1995), now U.S. Pat. No. 5,801,155, all of the disclosures of which are hereby incorporated herein by reference in their entirety.

TECHNICAL FIELD

The present invention is in the field of molecular biology. More specifically, the invention is in the field of assays that utilize oligonucleotides as primers or hybridization probes.

BACKGROUND

Minor groove binding agents which non-covalently bind into the minor groove of double stranded DNA are known in the art. Intercalating agents which bind to double stranded DNA or RNA are also well known in the art. Intercalating agents are, generally speaking, flat aromatic molecules which non-covalently bind to double stranded DNA or RNA by positioning (intercalating) themselves between interfacing purine and pyrimidine bases of the two strands of double stranded DNA or RNA. U.S. Pat. No. 4,835,263 describes oligonucleotides which are covalently bound to an intercalating group. Such oligonucleotides carrying an intercalating group can be useful as hybridization probes.

In many analytic, diagnostic and experimental systems in modern biology, oligonucleotides are used in procedures that require that they base pair (i.e., hybridize) with a nucleic acid sequence that is complementary to the oligonucleotide. This hybridization process may be used to directly detect a sequence in a nucleic acid molecule (i.e., probing), to initiate synthesis at a specific sequence (i.e., priming), or to block synthesis by inhibiting primer extension (i.e., clamping). In all these procedures, the technique relies on the formation of a nucleic acid duplex (or hybrid) based on the principle that the duplex will form only if the two strands are complementary over a significant portion of their lengths. Complementarity is determined by the formation of specific hydrogen bonds between the nucleotide bases of the two strands such that only the base pairs adenine-thymine, adenine-uracil and guanine-cytosine form hydrogen bonds, giving sequence specificity to the double stranded duplex. In a duplex formed between an oligonucleotide and another nucleic acid molecule, the stability of the duplex is a function of its length, the number of specific (i.e., A-T, A-U and G-C) hydrogen bonded base pairs, and the base composition (ratio of guanine-cytosine to adenine-thymine or adenine-uracil base pairs), since guanine-cytosine pairs provide a greater contribution to the stability of the duplex than do adenine-thymine or adenine-uracil pairs.

Usually, the relative stability of a duplex is measured experimentally by heating the duplex in solution until the strands of the duplex separate. The quantitative stability of a duplex is expressed by the temperature at which one-half the base pairs have dissociated, commonly known as the "melting temperature" or $T_m$. In practice, this is usually measured by monitoring the ultraviolet absorbance of a solution of nucleic acid while the temperature is increased and denoting the $T_m$ as the temperature at half the maximal absorbance at 260 nm (since an increase in absorbance at 260 nm accompanies the dissociation of the two strands of a duplex).

Essentially all procedures involving analysis of a target nucleic acid sequence require a hybridization step, either to determine directly if the complement of a known sequence (the probe) is present in a sample or to initiate synthesis (prime) from a specific sequence. Control of the specificity of the hybridization step is key to successful and accurate nucleic acid analysis. In most cases, exact matching between the sequence of the probe or primer and the sequence of its target is required. Nevertheless, in some cases, the analytical approach requires the stabilization of a probe or primer in a duplex that is not a perfect match. Therefore, techniques and material that can be used to control hybridization procedures such that it is possible, on the one hand, to obtain only perfectly matched duplexes and, under alternate conditions, to stabilize mismatched duplexes, would extend the use of oligonucleotides and allow analytical and experimental procedures that are now very difficult or unreliable.

For example, many analytical procedures require primer extension as a means of amplifying or labeling a DNA or RNA sequence so that it may be examined further. See, for example, Sambrook et al., MOLECULAR CLONING: A LABORATORY MANUAL, Second Edition, Cold Spring Harbor Laboratory Press (1989). These procedures include, but are not limited to, chain-termination sequencing-based on the Sanger Method (Sanger et al. (1977) *Proc. Natl. Acad. Sci. USA* 74:5463-5467), polymerase chain reaction (PCR) amplification of DNA or RNA sequences (U.S. Pat. Nos. 4,683,202; 4,683,195 and 4,800,159; Mullis and Faloona; *Meth. Enzymol.*, vol 155, Academic Press, New York, 1987, pp. 335-50; and Saiki et al. (1985) *Science* 230:1350-1354), cDNA synthesis (Rougeon et al. (1975) *Nucleic Acids Res.* 2:2365-2378) and combinations of these procedures for specific purposes such as "differential display" (Liang et al. (1992) *Science* 257:967-971), mRNA indexing (Kato et al. (1996) *Nucleic Acids Res.* 24:294) and gene hunting (Tung et al. (1989) In Erlich, H. A. (ed.), *PCR Technology: Principles and Applications for DNA Amplification*. Stockton press, pp. 99-104) among others.

Each of these procedures requires hybridization, to a target sequence, of an oligonucleotide primer from whose 3' terminus synthesis is initiated. The ability of an oligonucleotide to serve as a primer depends upon die stability of the duplex it forms with its template, especially at its 3' terminus. The ability of an oligonucleotide to serve as a unique, specific primer depends upon the stability of the duplex its forms with its perfect complement and, conversely, on the lack of stability of a duplex including one or more noncomplementary (i.e., mismatched) base pairs. Current priming methods rely on the use of oligonucleotides sufficiently long to form stable duplexes at temperatures necessary or convenient for extension. However, longer oligonucleotides are more prone to mismatch pairing than shorter oligonucleotides. Further, specific information may restrict the use of longer oligonucleotides.

To give one example, many methods involving oligonucleotides utilize some type of amplification technology, often based on a polymerase chain reaction (PCR). See, for example, U.S. Pat. Nos. 4,683,195; 4,683,202; and 4,800,159. PCR has become an exceptionally powerful tool in molecular biology, but certain factors limit its versatility. Because PCR involves multiple cycles of DNA denaturation, elevated temperatures are usually required, making the use of a thermophilic polymerizing enzyme necessary to avoid the inconvenience of supplying fresh polymerizing enzyme at each cycle. However, at the elevated temperatures optimal for activity of a thermophilic polymerase and required for denaturation, oligonucleotides shorter than about 20 nucleotides (20-mers) do not form hybrids that are stable enough to serve as primers for polymerase-catalyzed elongation. Consequently, current PCR-based techniques generally require primers at least 20 nucleotides in length to form hybrids that will be stable at the temperatures and stringencies commonly used for PCR. Saiki (1989) In Erlich, H. A. (ed.), *PCR Technology: Principles and Applications for DNA Amplification.* Stockton Press, pp. 7-16.

In another example, mRNA "indexing" requires priming from the 3' end of a messenger RNA (mRNA) molecule or from a cDNA made from the mRNA. Kato et al., supra. This technique employs separate populations of oligo-dT-containing primers, each additionally containing an extension of one to approximately three nucleotides adjacent to the oligo A sequence on the 5' side of the oligo A. The objective is to cause synthesis of specific segments of DNA corresponding to the 3' end of each mRNA (determined by the oligo A sequence) but separated into specific populations, determined by the specific base at positions 1 to (approximately) 3, upstream of the oligo A. If each primer is used in a separate reaction, separate populations of cDNAs are generated, each of which is a subset of the total mRNA. These can be used to analyze cellular expression. This procedure is usually combined with PCR, by including a second primer in each separate reaction. The practicability of this method is limited by the necessity to use sufficiently long oligo thymidylate, complementary to the oligo A, to stabilize the first primer. This can result in stabilization of mismatches within the one to three specific bases at the 3' end of the primer. In a population of primer and templates, these mismatches allow synthesis of improperly primed, and therefore misleading cDNA molecules leading to incorrect indexing of mRNA. Alternatively, some primers are insufficiently stable to prime efficient synthesis; consequently, the extension products they would have generated are underrepresented in the population, again leading to incorrect indexing of the corresponding mRNA. Short primers that are stable at elevated temperatures commonly used for PCR, but that form only perfect duplexes (i.e., do not prime mismatches) would increase the utility of this technique.

Important new techniques, such as gene hunting and differential display, would also benefit from the use of shorter primers. In some cases, short primers are essential for these methods. In gene hunting, a family of amplified transcripts shares a short degenerate sequence that specifies a conserved peptide motif, and this priming sequence is necessarily limited in length. Tung et al., supra. Stockton press, pp. 99-104. In differential display, complete representation of a transcript pool is sought, and this is optimally achieved by priming with 6-mers. The impracticality of using such short primers necessitates the use of longer degenerate ODNs. Liang et al., supra. However, long degenerate ODNs may not provide an accurate representation of the complexity of a mRNA population, since mispriming can generate non-specific products, and inefficient hybridization of the primer can lead to under representation of certain transcripts. Buchner et al. (1995) *Stat. Mol. Biol.* 8:12-14. Application of longer oligonucleotides to viral diagnostics are limited, because amplification of a common sequence from multiple strains can be complicated by the presence of genomic variability. Smits et al. (1992) *J. Gen. Virol.* 73:3263-3268. Again, shorter primers are desirable, since the shorter the sequence used for priming, the less likely that it will encompass a region characterized by genomic variability.

In addition to priming, oligonucleotide hybridization is used in several techniques to probe nucleic acid sequences. In general, these assays require that the probes form perfectly-matched duplexes with target sequences. These assays are usually based on one of three schemes: 1) The probe or target is labeled (e.g., with a radioactive isotope, a fluorescent dye or a reactive compound), the nucleic acids are placed under hybridization conditions following hybridization, the non-hybridized labeled material is removed and the remaining label is quantitated. 2) The probe is specifically labeled and placed with the target DNA under hybridization conditions, following hybridization, the hybridized probe is detected by virtue of a property unique to a duplex containing the probe such as susceptibility to a duplex-specific nuclease (e.g., U.S. Pat. No. 5,210,015), 3) fluorescence generated by interaction of a dye with duplex DNA (Wittwer et al. (1997) *BioTechniques* 22:130-138) or separating a fluorophore from a quenching dye by the extension of the probe as a result of hybridization.

A method that could be used in essentially all these types of nucleic acid hybrid detection systems to enhance the distinction between exact duplexes and duplexes with one or more mismatched base pairs would be a very useful tool in specific nucleic acid sequence determination and clearly be valuable in clinical diagnosis, genetic research and forensic laboratory analysis.

For example, many diseases are associated with known inherited polymorphisms or mutations. Many of these are due to single nucleotide changes and, to be useful, a genetic assay based on hybrid formation must be able to distinguish between a hybrid with all base pairs matched and one with a single mismatch. A group of single base differences at certain points in the sequences of human DNA called single nucleotide polymorphisms have been determined to be stably inherited genetic markers (Schaeffer et al. (1998) *Nature Biotechnology* 16:33). These markers can be associated with ancestral populations and in some cases can be associated with characteristics such as disease susceptibility or response to environmental factors such as chemicals, drugs, etc. Although these polymorphisms can theoretically be discovered by the tedious process of gene sequencing, their use as genetic markers associated with a phenotype in, for example, medical practice or research, necessitates a screening or typing system that is capable of analyzing DNA from tens to hundreds of individuals. This process will not easily be accommodated by current methods of DNA sequencing. Single nucleotide polymorphism analysis thus represents an additional field in which there exists a need for a reliable method for distinction of single base differences in DNA sequences by a process such as hybridization.

Various additional assays that involve oligonucleotide priming are known in the art. These include, but are not limited to, assays that utilize the nuclease activity of a polymerase enzyme to release label from a probe hybridized to an extension product (see, for example; U.S. Pat. No. 5,210,015), and assays in which hybridization of two or more oligonucleotides to adjacent sites on a target nucleic acid results in interactions between the oligonucleotides, such as, for example, fluorescence resonance energy transfer. See, for example, Stavrianopoulos et al., U.S. Pat. No. 4,868,103; and Heller et al., European Patent Publication 070,685. These techniques are also limited by the length of the oligonucleotide that can be used for efficient hybridization and/or priming. The ability to use shorter oligonucleotides would therefore be beneficial in these procedures and, indeed, in any application that involves hybridization of an oligonucleotide to a target nucleic acid.

Chemical modification of short oligonucleotides has been attempted, with an eye toward improving hybrid stability while retaining effective priming ability. Certain modifications, such as N3'→P5' phosphoramidates (Gryaznov et al. (1994) *J. Am. Chem. Soc.* 116:3143-3144) and peptide (Nielsen et al. (1994) *Bioconjugate Chem.* 5:3-7) or guanidine (Dempcy et al. (1995) *Proc. Natl. Acad. Sci. USA,* 92:6097-6101) linkages, have been shown to enhance hybrid stability. However, such modified oligonucleotides are non-extendible, because they lack a 3'-OH group, and are therefore unable to serve as primers. Other hybrid-stabilizing modifications that have not been investigated with respect to their ability to support primer extension are 2'-modified sugars (Monia et al. (1993) *J Biol. Chem.* 268:14514-14522; Sproat et al. (1993) In Crooke, S. T. and Lebleu, B. (eds), *Antisense Research and Applications.* CRC Press, Boca Raton, Fla., pp. 352-362), conjugated intercalating agents (Asseline et al. (1984) *Proc. Natl. Acad. Sci. USA* 81:3297-3301) and substituted bases such as 2-aminoadenine (Lamm et al. (1991) *Nucleic Acids Res.* 19:3193-3198) or C5 propynyl pyrimidines (Wagrier et al. (1993) *Science* 260:1510-1513). Thus, the need remains for a method of modifying short oligonucleotides so that they form more stable hybrids, such that the modification will not interfere with the ability of the oligonucleotides to serve as primers.

A further shortcoming in the use of oligonucleotides as probes and primers is the difficulty of obtaining specificity such as single nucleotide mismatch discrimination using oligonucleotide probes and/or primers. In many cases, it is necessary to distinguish target sequences which differ by a single nucleotide and, in some cases, it would be desirable to do so using oligonucleotides. That is, it would be useful to have a given oligonucleotide which is able to hybridize to a target sequence with which it is complementary along its entire length (a perfect hybrid or perfect match), but which, under identical stringency conditions, will not hybridize to a target sequence that is non-complementary to the oligonucleotide at a single nucleotide residue (a single-nucleotide mismatch). Unfortunately, this type of single nucleotide mismatch discrimination is possible only when fairly short (for example, <20 mer) oligonucleotides are used. The disadvantage of using such short oligonucleotides is that they hybridize weakly, even to a perfectly complementary sequence, and thus must be used under conditions of reduced stringency. If it were possible to achieve single nucleotide mismatch discrimination under conditions of high stringency (such as those under which most amplification reactions are conducted), improvements in speed and efficiency would accrue in techniques such as allele-specific oligonucleotide hybridization, single nucleotide polymorphism analysis, and functional genomics, to name just a few.

DISCLOSURE OF THE INVENTION

The present invention relates to a covalently bound oligonucleotide and minor groove binder combination which includes an oligonucleotide having a plurality of nucleotide units, a 3'-end and a 5'-end, and a minor groove binder moiety covalently attached to at least one of said nucleotides. The minor groove binder is typically attached to the oligonucleotide through a linking group comprising a chain of no more than 15 atoms. The minor groove binder moiety is a radical of a molecule having a molecular weight of approximately 150 to approximately 2000 Daltons which molecule binds in a non-intercalating manner into the minor groove of double stranded DNA, RNA or hybrids thereof with an association constant greater than approximately $10^3$ $M^{-1}$.

In another aspect, the present invention relates to the process of synthesizing certain covalently bound oligonucleotide minor groove binder combinations, and to the manner of using such combinations for hybridization probe and related analytical and diagnostic, as well as therapeutic (anti-sense and anti-gene) purposes.

It has now been discovered that conjugation of a minor groove binder (MGB) to an oligonucleotide (ODN) dramatically increases the stability of the hybrid formed between the oligonucleotide and its target. Increased stability (i.e., increased degree of hybridization) is manifested in a higher melting temperature ($T_m$: the temperature at which half of the base pairs have become unpaired) of hybrid duplexes formed by such MGB-oligonucleotide conjugates, compared to those formed by an unconjugated oligonucleotide of identical length and sequence. This effect is particularly pronounced for short oligonucleotides (e.g., less than about 21 nucleotides in length) and makes possible, for the first time, the use of short oligonucleotides as probes and primers, under high stringency conditions. Conjugation of an oligonucleotide with a MGB, with its attendant increase in hybrid stability, does not adversely affect the ability of the conjugated oligonucleotide to serve as a primer. Therefore, it is now possible, using the methods and compositions of the present invention, to use shorter oligonucleotides than previously required in techniques in which hybridization is required, such as polymerase chain reactions and hydrolyzable probe assays, which are generally conducted at high stringency, due to the use of high temperatures and thermophilic enzymes.

In addition to increased duplex stabilization, MGB-oligonucleotide conjugates retain the heightened sensitivity to sequence mismatch that is characteristic of unconjugated short oligonucleotides with low melting temperatures. Thus, conjugation to a MGB endows very short oligonucleotides (e.g. oligonucleotides containing less than about 21 nucleotides) with greater specificity, by endowing them with the potential to form hybrids having a stability characteristic of much longer oligonucleotides, while retaining the ability to discriminate between sequences differing by a single nucleotide. Use of short oligonucleotides at high stringency now becomes possible, using MGB-oligonucleotide conjugates.

The use of MGB-oligonucleotide conjugates as probes and primers provides improvements in speed, sensitivity and versatility to a variety of assays involving hybridization of oligonucleotides. Such assays are well-known in the art and include, but are not limited to, single nucleotide mismatch detection, in situ hybridization, polymerase chain reaction (PCR, see U.S. Pat. Nos. 4,683,202; 4,683,195 and 4,800, 159), allele-specific oligonucleotide (ASO) hybridization (Huang et al. (1992) *Acta Haematol.* 88:92-95), detection of single-nucleotide polymorphism (Mullis and Faloona; *Meth. Enzymol.,* vol. 155, Academic Press, New York, 1987, pp. 335-50), microsatellite analysis using short tandem repeats (Tautz (1993) in "DNA Fingerprinting: State of the Science," Pena et al., ed, Birkhauser, Basel, pp. 21-28), random amplification of polymorphisms in DNA (Williams et al, *Meth. Enzymology,* vol. 218, Academic Press, New York, 1993, pp. 704-740), DNA amplification fingerprinting (Caetano-Anollés et al. (1991) *Biotechnology* 9:553-557), assays involving fluorescence energy transfer, assays involving release of label by exonuclease-mediated hydrolysis of a hybridized oligonucleotide probe, assays involving ligation of two or more oligonucleotides, etc.

All patents, patent applications and publications mentioned herein, either supra or infra, are hereby incorporated by reference in their entirety.

BRIEF DESCRIPTION OF THE DRAWINGS

FIG. 1 is a graph showing the results of a slot blot hybridization assay.

FIG. 2 shows the structure of 1,2-dihydro-(3B)-pyrrolo[3,2-e]indole-7-carboxylate, also known as $CDPI_3$. Also shown are the structures of the linkers used for conjugation of $CDPI_3$ to the 5' and 3' ends of oligonucleotides.

FIG. 3 shows a comparison of unmodified and MGB-conjugated 16-mer, 12-mer and 10-mer oligonucleotides as PCR primers. Conjugated oligonucleotides contained a 5'-$CDPI_3$ moiety. The indicated pair of primers was used to amplify a segment of single-stranded M13mp19 DNA according to the procedure described in Example 1. PCR products were analyzed on 2% agarose gels stained with ethidium bromide.

In FIG. 3A, MGB-oligonucleotide conjugates (lanes 1-4) were compared to unmodified oligonucleotides (lanes 5-8) as reverse primers. In all cases, the oligonucleotides were 16-mers, and the annealing temperature was 45° C. The specific pairs of oligonucleotides used as primers, and the predicted sizes of the products, were as follows. Lane 1: 4-C and 1 (307 nucleotides). Lane 2: 9-C and 1 (297 nucleotides). Lane 3: 12-C and 1 (217 nucleotides). Lane 4: 13-C and 1 (181 nucleotides). Lane 5: 4 and 1 (307 nucleotides). Lane 6: 9 and 1 (297 nucleotides). Lane 7: 12 and 1 (217 nucleotides). Lane 8: 13 and 1 (181 nucleotides); See Table 6 for the sequences and structures of the oligonucleotides, and for their location within the M13mp19 genome. Lane M comprises molecular weight markers, whose size (in nucleotides) is given to the left of the Figure.

In FIG. 3B, MGB-oligonucleotide conjugates (lanes 1-4) were compared to unmodified oligonucleotides (lanes 5-8) as reverse primers. In all cases, the oligonucleotides were 16-mers, and the annealing temperature was 68° C. The specific pairs of oligonucleotides used as primers, and the predicted sizes of the products, were as follows. Lane 1: 4-C and 1 (307 nucleotides). Lane 2: 9-C and 1 (297 nucleotides). Lane 3: 12-C and 1 (217 nucleotides). Lane 4: 13-C and 1 (181 nucleotides). Lane 5: 4 and 1 (307 nucleotides). Lane 6: 9 and 1 (297 nucleotides). Lane 7: 12 and 1 (217 nucleotides). Lane 8: 13 and 1 (181 nucleotides). See Table 6 for the sequences and structures of the oligonucleotides, and for their location within the M13mp19 genome. Lane M comprises molecular weight markers as in FIG. 3A.

In FIG. 3C, 10-mer (lane 1; oligonucleotides 3-C and 7-C) and 12-mer (lane 2; oligonucleotides 6-C and 2-C) MGB-oligonucleotide conjugates were used as primers and the annealing temperature was 55° C. The predicted product length was 307 nucleotides for both lanes. Lane M comprises molecular weight markers as in FIG. 3A.

FIG. 4 shows a comparison of unmodified and MGB-conjugated 8-mer and 6-mer oligonucleotides as PCR primers. Conjugated oligonucleotides contained a 5'-$CDPI_3$ moiety. The indicated pair of primers were used to amplify a segment of single-stranded M13mp19 DNA using a touchdown PCR protocol as described in Example 1. Products were analyzed on 8% polyacrylamide sequencing gels and visualized by silver staining.

In FIG. 4A, the forward primer was a 10-mer, the reverse primers were 8-mers, and the annealing temperature was gradually decreased from 55 to 41° C. The specific primer pairs, and the predicted sizes of the products, were as follows. Lane 1: 11 and 3 (217 nucleotides). Lane 2: 8 and 3 (297 nucleotides). Lane 3: 11-C and 3-C (217 nucleotides). Lane 4: 8-C and 3-C (297 nucleotides). Lane M denotes molecular weight markers from a Hae III digest of ΦX174 DNA, whose sizes (in nucleotides) are given to the right of the figure.

In FIG. 4B, the forward primer was a 10-mer, the reverse primers were 6-mers, and the annealing temperature was gradually decreased from 50 to 37° C. The specific primer pairs, and the predicted sizes of the products, were as follows. Lane 1: 10-C and 3-C (295 nucleotides). Lane 2: 5-C and 3-C (305 nucleotides). Lane M denotes molecular weight markers from a Hae III digest of ΦX174 DNA, as in FIG. 4A.

FIG. 5 shows the nucleotide sequence of the E. coli supF gene contained in the plasmid pSP189 (SEQ ID No.: 40), indicating the locations of the target sequences for the amplification primers (labeled "Primer 1" and "Primer 2"), the region that served as target in a hydrolyzable probe assay (labeled "15-mer"), and the single-nucleotide substitutions that were introduced into the target sequence for the experiment shown in FIG. 6 (shown underneath the region labeled "15-mer").

FIG. 6 shows results of a hydrolyzable probe assay, using MGB-conjugated 15-mer probes wherein all guanine bases in the probe were substituted with the guanine analogue ppG. The target was the E. coli supF gene. Annealing/elongation was conducted at 75° C. for 20 sec per cycle.

MODES FOR CARRYING OUT THE INVENTION

The practice of the present invention will employ, unless otherwise indicated, conventional techniques in organic chemistry, biochemistry, oligonucleotide synthesis and modification, nucleic acid hybridization, molecular biology, microbiology, genetics, recombinant DNA; and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook et al., supra; Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIES AND ANALOGUES: A PRACTICAL APPROACH, IRL Press (1991).

A prominent feature of the novel composition of matter of the present invention is that a minor groove binding molecule is covalently bound to an oligonucleotide. As is noted in the introductory section of the present application for patent, a minor groove binder is a molecule that binds within the minor groove of double stranded deoxyribonucleic acid (DNA). Although a general chemical formula for all known minor groove binding compounds cannot be provided because such compounds have widely varying chemical structures, compounds which are capable of binding in the minor groove of DNA, generally speaking, have a crescent shape three dimensional structure. Most minor groove binding compounds of the prior art have a strong preference for A-T (adenine and thymine) rich regions of the B form of double stranded DNA. The minor groove binding compounds, or more accurately stated moieties of the oligonucleotide-minor groove binding conjugates of the present invention, also have the same preference. (The oligonucleotide-minor groove binding conjugates of the present invention are hereinafter sometimes referred to as ODN-MGB.) Nevertheless, minor groove binding compounds which would show preference to C-G (cytosine and guanine) rich regions are also theoretically possible. Therefore, ODN-MGB compounds incorporating a radical or moiety derived from minor groove binder molecules having preference for C-G regions are also within the scope of the present invention. The preference for A-T regions of the known minor groove binders is currently explained by the existence of an unfavorable steric interference between the 2-amino group of guanine and some well known minor groove binders. However, as it will become apparent from the ensuing further description, when guanine is replaced by hypoxanthine in an ODN-MGB of the present invention, the potential for the above-noted unfavorable steric interference no longer exists and strong binding of the ODN-MGB to a complementary strand may occur.

Generally speaking, minor groove binding compounds known in the prior art do not bind to double stranded RNA or to a double stranded hybrid of DNA and RNA. However, the ODN-MGB compounds of the present invention exhibit potential for binding to single stranded RNA, and the foregoing feature forms another interesting and novel aspect of the present invention.

Examples of known minor groove binding compounds of the prior art, which can, in accordance with the present invention, be covalently bound to ODNs to form the novel ODN-MGB conjugates are certain naturally occurring compounds such as netropsin, distamycin and lexitropsin, mithramycin, chromomycin A₃, olivomycin, anthramycin, sibiromycin, as well as further related antibiotics and synthetic derivatives. Certain bisquarternary ammonium heterocyclic compounds, diarylamidines such as pentamidine, stilbamidine and berenil, CC-1065 and related pyrroloindole and indole polypeptides, Hoechst 33258, 4'-6-diamidino-2-phenylindole (DAPI) as well as a number of oligopeptides consisting of naturally occurring or synthetic amino acids are minor groove binder compounds. The chemical structures of the following examples are illustrated below.

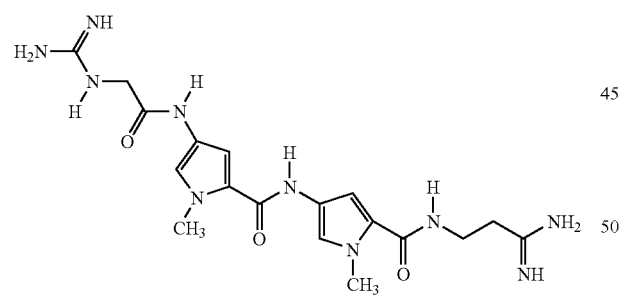

Netropsin

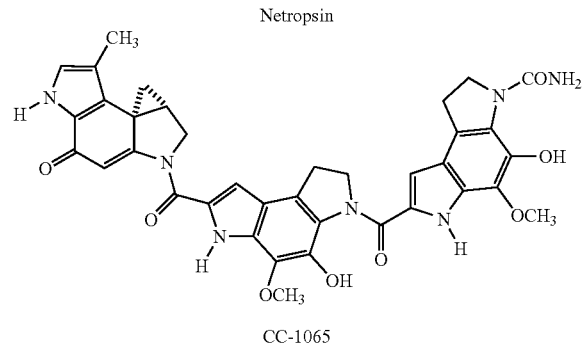

CC-1065

-continued

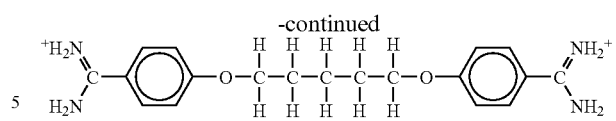

Pentamidine

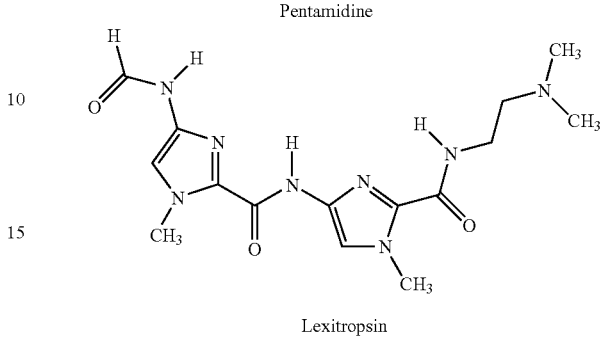

Lexitropsin

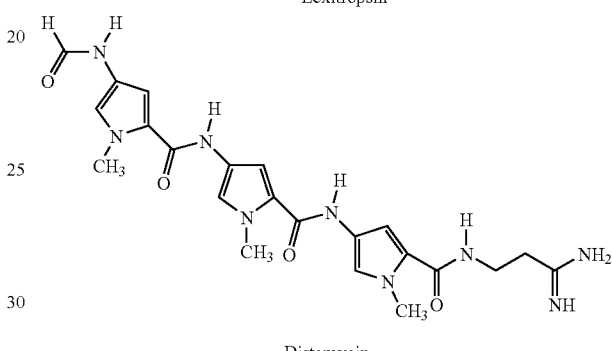

Distamycin

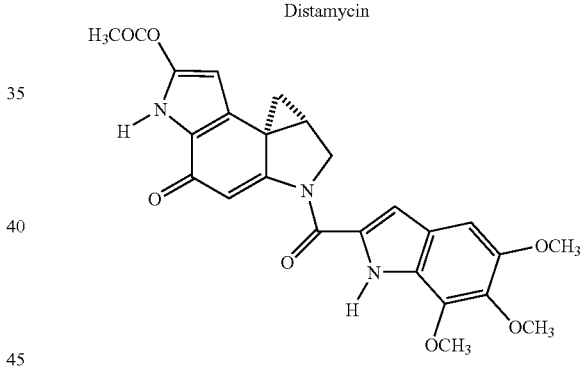

Duocarmycin SA

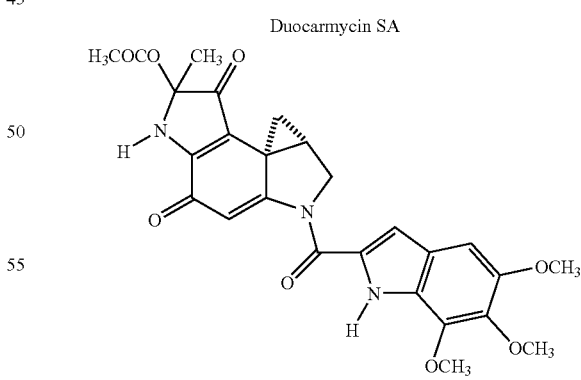

Duocarmycin A

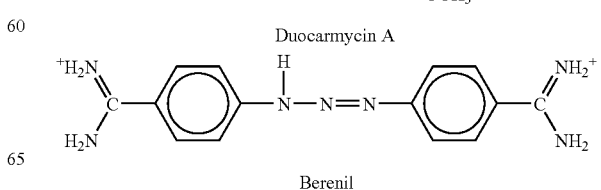

Berenil

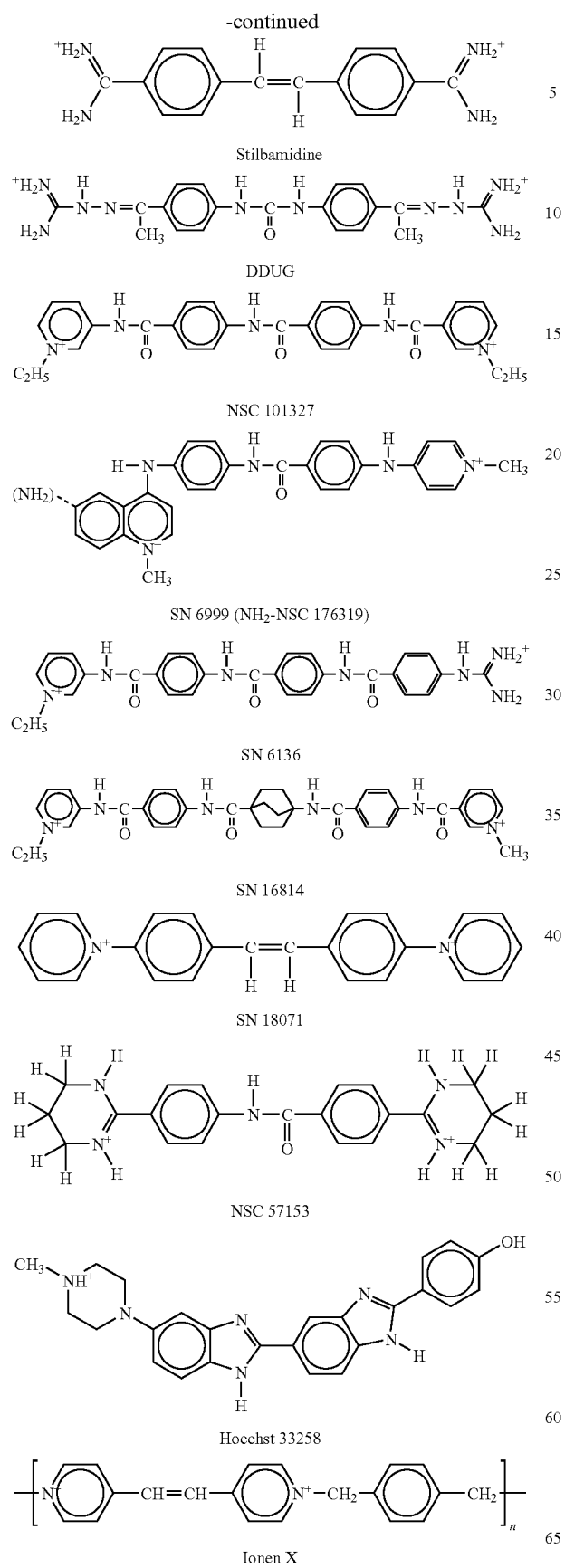

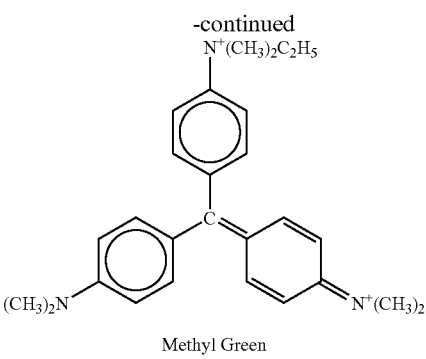

For the purposes of the present invention a molecule is a minor groove binder if it is capable of binding within the minor groove of double stranded DNA with an association constant of $10^3$ $M^{-1}$ or greater. This type of binding can be detected by well established spectrophotometric methods, such as ultraviolet (u.v.) and nuclear magnetic resonance (nmr) spectroscopy and also by gel electrophoresis. Shifts in u.v. spectra upon binding of a minor groove binder molecule, and nmr spectroscopy utilizing the "Nuclear Overhauser" (NOSEY) effect are particularly well known and useful techniques for this purpose. Gel electrophoresis detects binding of a minor groove binder to double stranded DNA or fragment thereof, because upon such binding the mobility of the double stranded DNA changes.

Intercalating molecules or agents are readily distinguished from minor groove binders on the basis that the intercalating agents are flat aromatic (preferably polycyclic) molecules versus the "crescent shape" or analogous geometry of the minor groove binders. An experimental distinction can also be made by nmr spectroscopy utilizing the Nuclear Overhauser effect.

As noted above, for the purposes of the present invention a molecule is a minor groove binder if its association constant within the minor groove of double stranded DNA is $10^3$ $M^{-1}$ or greater. However, some minor groove binders bind to the high affinity sites of double stranded DNA with an association constant of the magnitude of $10^7$ to $10^9$ $M^{-1}$.

In accordance with the present invention, the minor groove binder molecule is derivatized, in essence formed into a "radical" and linked to an appropriate covalent structure or chain of atoms that attaches the minor groove binder to the ODN. In a sense, the linking "chain" can and sometimes is considered as part of the minor groove binder since the nature of the linkage is such that it does not adversely affect the minor groove binding properties of the ODN-MGB molecule. However, it suits the present description better to conceptually separate the minor groove binder from the group that covalently attaches it to the ODN. The radical "formed" from the minor group binder molecule is hereinafter referred to as the "minor groove binder moiety", and the covalent linkage (which may be a chain of up to approximately 15 atoms) that attaches the minor groove binder moiety to the oligonucleotide is called the "linking group". The preferred embodiments of the minor groove moieties in accordance with the present invention are described in detail after description of the oligonucleotide portion of the ODN-MGB conjugate compounds of the present invention.

Broadly speaking, the oligonucleotide portion of the ODN-MGB conjugates of the present invention comprise approximately 3 to 100 nucleotide units. The nucleotide units which can be incorporated into the ODNs in accordance with the present invention include the major heterocyclic bases naturally found in nucleic acids (uracil, cytosine, thymine, adenine and guanine) as well as naturally occurring and synthetic modifications and analogs of these bases such as hypoxanthine, 2-aminoadenine, 2-thiouracil, 2-thiothymine, 5-N$^4$ ethenocytosine, 4-aminopyrrazolo[3,4-d]pyrimidine and 6-amino-4-hydroxy-[3,4-d]pyrimidine. The respective structures of the 2-deoxyribosides of 5-N$^4$ ethenocytosine 4-aminopyrrazolo[3,4-d]pyrimidine and of 6-amino-4-hydroxy-[3,4-d]pyrimidine are shown below.

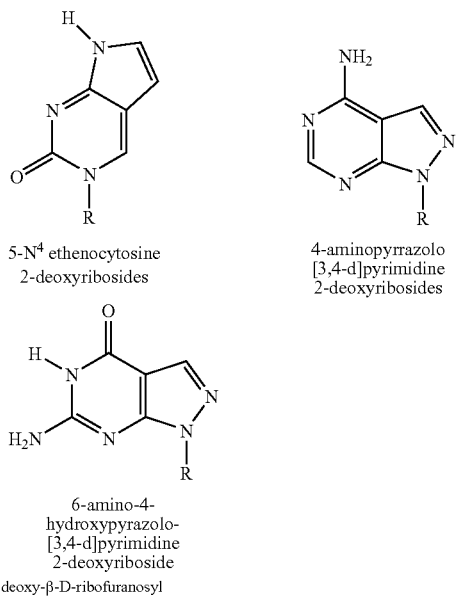

5-N$^4$ ethenocytosine
2-deoxyribosides 4-aminopyrrazolo
[3,4-d]pyrimidine
2-deoxyribosides 6-amino-4-
hydroxypyrazolo-
[3,4-d]pyrimidine
2-deoxyriboside R = 2-deoxy-β-D-ribofuranosyl In addition, the nucleotide units which are incorporated into the ODNs of the ODN-MGB conjugates of the present invention may have a cross-linking function (an alkylating agent) covalently bound to one or more of the bases, through a linking arm. Since the ODN-MGB conjugates having an attached cross-linking agent form an important class of preferred embodiments of the present invention these structures will be described in more detail below.

The "sugar" or glycoside portion of the ODN-MGBs of the present invention may comprise deoxyribose, ribose, 2-fluororibose, 2-O alkyl or alkenylribose where the alkyl group may have 1 to 6 carbons and the alkenyl group 2 to 6 carbons. In the naturally occurring nucleotides and in the herein described modifications and analogs the deoxyribose or ribose moiety forms a furanose ring, the glycosydic linkage is of the β configuration and the purine bases are attached to the sugar moiety via the 9-position, the pyrimidines via the 1-position and the pyrazolopyrimidines via the 1-position. Presently, oligodeoxyribonucleotides are preferred in accordance with the present invention, therefore the preferred sugar is 2-deoxyribose. The nucleotide units of the ODN's are interconnected by a "phosphate" backbone, as is well known in the art. The ODNs of the ODN-MGB conjugates of the present invention may include, in addition to the "natural" phosphodiester linkages, phosphorothiotes and methylphosphonates.

The ODNs of the ODN-MGB conjugates of the present invention may also have a relatively low molecular weight "tail moiety" attached to either at the 3'- or 5'-end. The "tail moiety" in this particular context is to be distinguished from the minor groove binding moiety, which is preferably also attached to the 3' or 5' ends, or to both. Thus, in this context the "tail moiety" if present at all, is attached to the end of the ODN which does not bear the minor groove binder moiety. By way of example, a tail molecule may be a phosphate, a phosphate ester, an alkyl group, and aminoalkyl group, or a lipophilic group.

With regard to the possible variations of the nucleotide units, the "phosphate backbone" and "tail" of the ODNs of the ODN-MGB conjugates of the present invention, the following should be kept in mind. The principal useful action of the ODN-MGB conjugates of the present invention lies in the ability of the ODN portion of the molecule to bind to a complementary sequence in single stranded DNA, RNA, double stranded DNA, and DNA-RNA hybrid, in a manner in which the minor groove binding moiety is incorporated in the newly formed "duplex" and thereby strengthens the bond, that is, increases the melting temperature (and association constant) of the newly formed duplex. Additionally, those preferred embodiments of the ODN-MGB conjugates of the present invention which include a cross-linking agent, also result in permanent covalent attachment of the ODN-MGB molecule to the complementary DNA or RNA strand, resulting in a permanently bound form. In light of the foregoing, those skilled in the art will readily understand that the primary structural limitation of the various component parts of the ODN portion of the ODB-MGB conjugate of the present invention lies only in the ability of the ODN portion to form a complementary strand to any specific target sequence, and that a large number of structural modifications, per se known in the art, are possible within these bounds. Moreover, synthetic methods for preparing the various heterocyclic bases, nucleosides, nucleotides and oligonucleotides which can form the ODN portion of the ODN-MGB conjugates of the present invention, are generally speaking well developed and known in the art. N$_4$,N$_4$-ethano-5-methyldeoxycytidine, its nucleoside, nucleotide and/or oligonucleotides incorporating this base can be made in accordance with the teachings of Webb, T. R.; Matteucci, M. D. Nucleic Acids Res., 1986, 14, 7661-7674, Webb, T. R.; Matteucci, M. D. J. Am. Chem. Soc., 1986, 108, 2764. 4-aminopyrazolo[3,4-d]pyrimidine, 6-amino-4-hydroxypyrazolo[3,4-d]pyrimidine, their nucleosides, nucleotides and oligonucleotides incorporating this base can be made in accordance with the teachings of Kazimierczuk et al. J. Am. Chem. Soc., 1984, 106, 6379-6382. Whereas oligonucleotide synthesis, in order to prepare an ODN of specific predetermined sequence so as to be complementary to a target sequence, can be conducted in accordance with the state of the art, a preferred method is described below. The preferred method incorporates the teaching of U.S. Pat. No. 5,419,966, the disclosure of which is expressly incorporated herein by reference.

The linking group is a moiety which covalently links the ODN portion of the conjugate to the minor groove binder moiety. Preferably, the linking group is such that the linkage occurs through a chain of no more than 15 atoms. Also preferably in accordance with the present invention the minor groove binder moiety is covalently attached to either the 3' or 5' end of the oligonucleotide. Nevertheless, attachment to a nucleotide in intermediate position, and particularly to the heterocyclic base of the nucleotide in intermediate position is also within the scope of the invention. Generally speaking, the linking group is derived from a bifunctional molecule so that one functionality such as an amine functionality is attached for example to the phosphate on the 5' end of the ODN, and the other functionality such as a carbonyl group (CO) is attached to an amino group of the minor groove binder moiety. Alternatively, the linking group may be derived from an amino alcohol so that the alcohol function is linked, for example, to the 3'-phosphate end of the ODN and the amino function is linked to a carbonyl group of the minor groove binder moiety. Still another alternative of a linking group includes an aminoalcohol (attached to the 3'-phosphate with an ester linkage) linked to an aminocarboxylic acid which in turn is linked in a peptide bond to the carbonyl group of the minor groove binder. Thus, preferred embodiments of the linking group have the formulas —HN(CH$_2$)$_m$CO, O(CH$_2$)$_m$CO and (CH$_2$)$_m$CH(OH)$_m$(CH$_2$)$_m$NHCO(CH$_2$)$_m$NH where the limitation on m is that the minor groove binder moiety should not be separated by more than approximately 15 atoms from the ODN. Preferred embodiments of linking groups are —O(CH$_2$)$_6$NH, —OCH$_2$CH(OH)CH$_2$NHCOCH$_2$CH$_2$NH and —HN(CH$_2$)$_5$CO. As it was noted above, the linking group could also be conceptualized as part of the minor groove binder moiety, which in that case would be considered directly attached to the ODN.

The basic limitation for the minor groove binder moiety has been set forth above, and is not definable by specific chemical structure. In addition to the molecular structure which causes minor groove binding, the minor groove binder moiety may also carry additional functions, as long as those functions do not interfere with minor groove binding ability. For example a reporter group, which makes the minor groove binder readily detectable by color, uv. spectrum or other readily discernible physical or chemical characteristic, may be covalently attached to the minor groove binder moiety. An example for such a reporter group is a diazobenzene function which in the example of a preferred embodiment is attached to a carbonyl function of the minor groove binder through a —HN(CH$_2$)$_m$COO(CH$_2$)$_m$S(CH$_2$)$_m$— bridge. Again, the reporter group or other like function carried by the minor groove binder can also be conceptualized as part of the minor groove binder moiety itself.

Preferred embodiments of the ODN-MGB conjugates are defined by the following chemical Formula 1. This definition includes the preferred embodiments of the minor groove binder moiety in accordance with the present invention, which may also include all or part of the linking group and other appendant groups such as a reporter group, as discussed above:

Formula 1

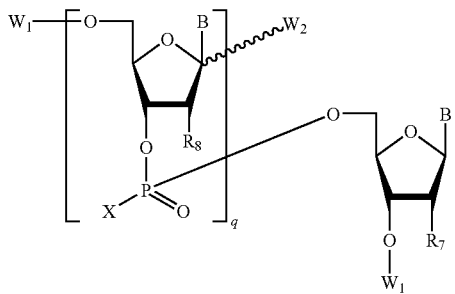

where x is O or S;

q is an integer between 3 to 100;

R$_8$ is H, OH, alkoxy having 1 to 6 carbons, O—C$_2$-C$_6$alkenyl, or F;

B is an aglycon selected from a group consisting of a heterocyclic base naturally found in nucleic acids and hypoxanthine, 2-aminoadenine, 2-thiouracil, 2-thiothymine, 5-N$^4$-ethenocytosine, 4-aminopyrrazolo[3,4-d]pyrimidine, 6-amino-4-hydroxy-[3,4-d]pyrimidine;

W$_1$ is H, PO(OH)$_2$ or a salt thereof, or a minor groove binder moiety attached to the 3' or 5' end of said oligonucleotide, the W$_1$ group including the linking group which covalently binds the minor groove binder moiety to the oligonucleotide through no more than 15 atoms;

W$_2$ is absent or is a minor groove binder moiety attached to one of the aglycons B, the W$_2$ group including the linking group which covalently binds the minor groove binder moiety to said aglycon, or W$_2$ is a cross-linking functionality including a linker arm which covalently binds the cross-linking functionality to said aglycon, wherein the minor groove binder moiety is a radical of a molecule having a molecular weight of approximately 150 to approximately 2000 Daltons that bind in a non-intercalataing manner into the minor groove of double stranded DNA, RNA or hybrids thereof with an association constant greater than approximately 10$^3$, with the proviso that at least one of said W$_1$ and W$_2$ groups is a minor groove binder moiety; and wherein further the minor groove binder moiety including the linking group has the formula selected from the group consisting of groups (a), (b), (c), (d) and (e):

where Y$_1$ represents a 5-membered ring having two double bonds and 0 to 3' heteroatoms selected from the group consisting of N, S and O, the NH and CO groups are attached respectively to two ring carbons which are separated by one ring atom from one another, the ring atom positioned between said two ring carbons is substituted only with H or is unsubstituted, each of the remaining ring atoms may be optionally substituted with 1; 2 or 3 R$_3$ groups;

where Y2 is a ring system consisting of a 6-membered aromatic ring condensed with a 5-membered ring having one double bond, the condensed ring system having 0 to 3 heteroatoms selected from the group consisting of N, S and O, each of the R$_6$N and CO groups is attached to a ring carbon which is in a different ring of the condensed ring system, and which is the second ring atom, respectively, from one common bridge head ring atom, the CO and NR$_6$ groups thereby positioning 2 non-bridgehead ring atoms between themselves on one side and 3 non-bridgehead ring atoms on the other side of the condensed ring system, the two non-bridgehead ring atoms on the one side being optionally substituted with an R$_7$ group, the three non-bridgehead ring atoms on the other side of the condensed ring system being optionally substituted with an R$_3$ group;

where Y$_3$ is a 6-membered aromatic ring having 0 to 3 N heteroatoms, and where each of the CO and NH groups is attached to a ring carbon, said ring carbons being in 1,4 position relative to one another, two ring atoms not occupied by the CO or NH groups on either one of the two sides of the 6-membered ring being optionally substituted with an R$_3$ group, the two ring atoms not occupied on the other side of the 6 membered ring being optionally substituted with an R$_7$ group;

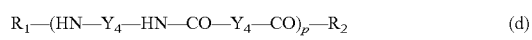

where Y$_4$ is a 6-membered aromatic ring having 0 to 3 N heteroatoms, and where each of the CO and NH groups is attached to a ring carbon, said ring carbons being in 1,4 position relative to one another in each ring, two ring atoms not occupied by the CO or NH groups on either one of the two sides of the 6-membered ring being optionally substituted with an R$_3$ group, the two ring atoms not occupied on the other side of the 6 membered ring being optionally substituted with an R$_7$ group;

where $Y_5$ is a ring system consisting of a 6 membered aromatic ring condensed with a 5-membered ring having one double bond, the condensed ring system having 0 to 3 heteroatoms selected from the group consisting of N, S and O, each of the $R_1$ and $R_2$ groups is attached to a ring carbon which is in a different ring of the condensed ring system, and which is the second ring atom, respectively, from one common bridgehead ring atom, the $R_1$ and $R_2$ groups thereby positioning 2 non-bridgehead ring atoms between themselves on one side and 3 non-bridgehead ring atoms on the other side of the condensed ring system, the two non-bridgehead ring atoms on the one side being optionally-substituted with an $R_7$ group, the three non-bridgehead ring atoms on the other side of the condensed ring system being optionally substituted with an $R_3$ group;

where $R_1$ and $R_2$ independently are H, F, Cl, Br, I, $NH_2$, $NHR_4$, $N(R_4)_2$, $N(R_4)_3^+$, OH, —O—, —S—, $OR_4$, SH, $SR_4$, $COR_4$, $CONHR_4$, $CON(R_4)_2$, $R_4$, $H_2N(CH_2)_mCO$, $CONH_2$, $CONHR_4$, $H_2N(CH_2)_mCOO(CH_2)_mS(CH_2)_mC_6H_4NNC_6H_4$, —$HN(CH_2)_mCO$, —CONH—, —$CONR_4$, $HN(CH_2)_mCOO$ $(CH_2)_mS(CH_2)_mC_6H_4NNC_6H_4$, and —$(CH_2)_mCH(OH)$ $(CH_2)_mNHCO(CH_2)_mNH$—, or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONH_4$, $CON(R_4)_2$ and $R_4$, or the $R_3$ groups may form a 3, 4, 5 or 6 membered ring condensed to the $Y_1$ ring;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_6$ is H, alkyl of 1 to 5 carbons, or $R_6$ and $R_7$ jointly form a 4,5, or 6 membered ring, optionally an —O—, —S—, —NH—, $NCH_3$—, or N-lower alkyl group being part of said ring;

$R_7$ is F, methyl or ethyl; —$CH_2$—, or —$CH_2CH_2$—;

m is an integer between 1 to 10;

n is an integer between 1 to 10, and p is an integer between 1 to 5.

Still more preferred embodiments of the ODN-MBG conjugates of the present invention are those where the minor groove binder moiety is defined as follows:

(1) the minor groove binding moiety is represented by formula (a) above and the five membered ring has the structure

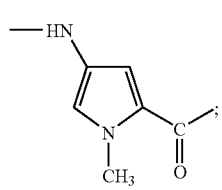

Formula 2

(2) the minor groove binding moiety is represented by formula (a) above wherein the five membered ring has the structure

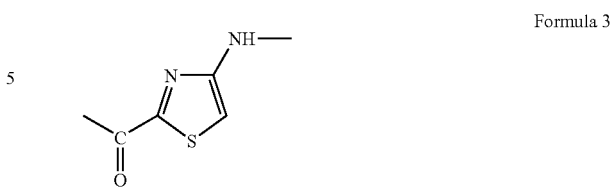

Formula 3 and (3) the minor groove binding moiety is represented by formula (b) and the condensed ring system has the structure

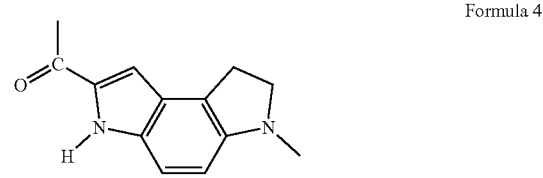

Formula 4

Embodiments Containing a Crosslinking Functionality

A class of preferred embodiments of the ODN-MGB conjugates of the present invention also include one or more cross-linking functionalities whereby after the ODN-MGB conjugate is bound to a complementary target sequence of DNA, RNA or fragment thereof, the crosslinking functionality irreversibly reacts with the target and forms a covalent bond therewith. Advantages of such covalent linking to a target sequence are in analytical, diagnostic use, as in hybridization probes, and in therapeutic (anti-sense and anti-gene) applications. The minor groove binder moiety which is also covalently bound to the ODN that complements the target sequence, enhances the initial non-covalent binding of the ODN-MGB conjugate to the target sequence and therefore facilitates the subsequent covalent bonding through the cross-linking function. The following considerations are pertinent as far as the cross-linking functionalities or agents incorporated into this class of ODN-MGB conjugates are concerned.

The cross-linking agents incorporated in the present invention are covalently bonded to a site on the ODN-MGB. Its length and steric orientation should be such that it can reach a suitable reaction site in the target DNA or RNA sequence after the ODN-MGB is hybridized with the target. By definition, the crosslinking functionality or agent has a reactive group which will react with a reactive group of the target DNA or RNA sequence. The cross-linking agent (or agents) may be covalently attached to one or more of the heterocyclic bases, to the sugar or modified sugar residues, or to the phosphate or modified phosphate functions of the ODN-MGB conjugates. The cross-linking agent may also be attached to the minor groove binder moiety as long as it does not interfere with its minor groove binding ability. Preferably the cross-linking agent or functionality is attached to one of the heterocyclic bases.

In simple terms the cross-linking agent itself may conceptually be divided into two groups or moieties, namely the reactive group, which is typically and preferably an electrophilic leaving group (L), and an "arms" (A) which attaches the leaving group L to the respective site on the ODN-MGB. The leaving group L may be chosen from, for example, such groups as chloro, bromo, iodo, $SO_2R'''$, or $S^+R'''R''''$, where each of R''' and R''' is independently $C_{1-6}$alkyl or aryl or R''' and R'''' together form a $C_{1-6}$alkylene bridge. Chloro, bromo and iodo are preferred. Within these groups haloacetyl groups such as —$COCH_2I$, and bifunctional "nitrogen mustards", such as —N—$[(CH_2)_2—Cl]_2$ are preferred. The leaving group will be altered by its leaving ability. Depending on the nature and reactivity of the particular leaving group, the group to be used is chosen in each case to give the desired specificity of the irreversibly binding probes.

Although as noted above the "arm" (or linker arm) A may conceptually be regarded as a single entity which covalently bonds the ODN-MGB to the leaving group L, and maintains the leaving group L at a desired distance and steric position relative to the ODN-MGB, in practice the "arm" A may be constructed in a synthetic scheme where a bifunctional molecule is covalently linked to the ODN-MGB, or to the ODN before the minor groove binder moiety is attached (for example by a phosphate ester bond to the 3' or 5' terminus, by a carbon-to-carbon bond to a heterocyclic base or by carbon to nitrogen bond to an amino substituted heterocyclic base) through its first functionality, and is also covalently linked through its second functionality (for example an amine) to a "hydrocarbyl bridge" (alkyl bridge, alkylaryl bridge or aryl bridge, or the like) which, in turn, carries the leaving group L.

A general formula of the cross linking function is thus -A-L, or -A-$L_2$ where L is the above defined leaving group and A is a moiety that is covalently linked to the ODN-MGB. The A "arm" moiety itself should be unreactive (other than through the leaving group L) under the conditions of hybridization of the ODN-MGB with the target sequence, and should maintain the leaving group L in a desired steric position and distance from the desired site of reactions such as an N-7 position of a guanosine residue in the target sequence. Generally speaking, the length of the A group should be equivalent to the length of a normal alkyl chain of approximately 2 to 20 carbons.

An exemplary more specific formula for a class of preferred embodiments of the cross-linking function is

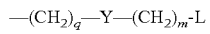

where L is the leaving group, defined above, each of m and q is independently 0 to 8, inclusive, and where Y is defined as a "functional linking group". For clarity of description this "functional linking group" is to be distinguished from the "linking group" that attaches the minor groove binder moiety to the ODN, although the functional linking groups described here for attaching the cross-linking agent can also be used for attaching a minor groove binder moiety to either end of the ODN, or to a nucleotide in intermediate position of the ODN. A "functional linking group" is a group that has two functionalities, for example —$NH_2$ and —OH, or —COOH and —OH, or —COOH and —$NH_2$, which are capable of linking the $(CH_2)_q$ and $(CH_2)$ bridges. An acetylenic terminus (HC≡C—) is also a suitable functionality for Y, because it can be coupled to certain heterocycles, as described below.

other exemplary and more specific formulas for a class of preferred embodiments of the cross-linking function are

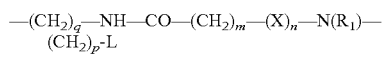

and

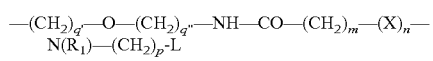

where q, m and L are defined as above in connection with the description of the cross-linking functions, q' is 3 to 7 inclusive, q'' is 1 to 7 inclusive, x is phenyl or simple substituted phenyl (such as chloro, bromo, lower alkyl or lower alkoxy substituted phenyl), n is 0 or 1, p is an integer from 1 to 6, and $R_1$ is H, lower alkyl or $(CH_2)_p$-L. Preferably p is 2. Those skilled in the art will recognize that the structure —N($R_1$)—$(CH_2)_2$-L describes a "nitrogen mustard", which is a class of potent alkylating agents. Particularly preferred are within this class of ODN-MGB conjugates those where the crosslinking agent includes the functionality N($R_1$)—$(CH_2)_2$-L where L is halogen, preferably chlorine; and even more preferred are those ODN-MGB conjugates where the cross-linking agent includes the grouping N—$[(CH_2)_2$-L$]_2$ (a "bifunctional" N-mustard).

A particularly preferred partial structure of the cross-linking agent includes the grouping

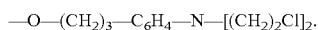

In a preferred embodiment the just-noted cross-linking group is attached to an n-hexylamine bearing tail at the 5' and 3' ends of the ODN in accordance with the following structure:

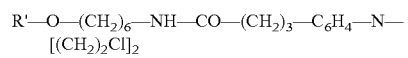

where R' signifies the terminal 5' or 3'-phosphate group of the ODN. The other terminal, or a nucleotide in an intermediate position bears the minor groove binder moiety.

In accordance with other preferred embodiments, the cross-linking functionality is covalently linked to the heterocyclic base, for example to the uracil moiety of a 2'-deoxyuridylic acid building block of the ODN-MGB conjugate. The linkage can occur through the intermediacy of an amino group, that is, the "armleaving group combination" (A-L) may be attached to a 5-amino-2'-deoxyuridylic acid building unit of the ODN. In still other preferred embodiments the "arm-leaving group combination" (A-L) is attached to the 5-position of the 2'-deoxyuridylic acid building unit of the ODN by a carbon-to-carbon bond. Generally speaking, 5-substituted-2'-deoxyuridines can be obtained by an adaptation of the general procedure of Robins et al. (*Can. J. Chem.*, 60:554 (1982); *J. Org. Chem.*, 48:1854 (1983)). In accordance with this adaptation, palladium-mediated coupling of a substituted 1-alkyne to 5-iodo-2'-deoxyuridine gives an acetylene-coupled product. The acetylenic dUrd analog is reduced, with Raney nickel for example, to give the saturated compound, which is then used for direct conversion to a reagent for use on an automated DNA synthesizer. Examples of reagents which can be coupled to 5-iodo-2'-deoxyuridine in accordance with this method are HC≡$CCH_2OCH_2CH_2N(CO)_2C_6H_4$ (phtalimidoethoxypropyne) and HC≡$CCH_2OCH_2CH_2NHCOCF_3$ (trifluoroacetamidoethoxypropyne).

In these examples the nucleosides which are obtained in this scheme are incorporated into the desired ODN; and the alkylating portion of the crosslinking agent is attached to the terminal amino group only after removal of the respective phtalic or trifluoroacetyl blocking groups, other examples of nucleotides where the crosslinking agent is attached to a heterocyclic base, are 2'-deoxy-4-aminopyrazolo[3,4-d]pyrimidine derivatives. These compounds can be made in accordance with the teaching of published PCT application WO: 90/03370 (published on Apr. 5, 1990).

Discussing still in general terms the structures of the modified ODNs of the present invention, it is noted that examination of double-stranded DNA by balland-stick models and high resolution computer graphics indicates that the 7-position of the purines and the 5-position of the pyrimidines lie in the major groove of the B-form duplex of double-stranded nucleic acids. These positions can be substituted with side chains of considerable bulk without interfering with the hybridization properties of the bases. These side arms may be introduced either by derivatization of dThd or dCyd, or by straightforward total synthesis of the heterocyclic base, followed by glycosylation. These modified nucleosides may be converted into the appropriate activated nucleotides for incorporation into oligonucleotides with an automated DNA synthesizer. With the pyrazolo[3,4-d]pyrimidines, which are analogs of adenine, the crosslinking arm is attached at the 3-position, which is equivalent to the 7-position of purine.

The crosslinking side chain (arm=A) should be of sufficient length to reach across the major groove from a purine 7- or 8-position, pyrimidine 5-position, pyrrolopyrimidine 5-position or pyrazolopyrimidine 3-position and reacting with the $\underline{N}$-7 of a purine (preferably guanine) located above (on the oligomer 3'side) the base pair containing the modified analog. The crosslinking side chain (arm=A) holds the functional group away from the base when the base is paired with another within the double-stranded complex. As noted above, broadly the arm A should be equivalent in length to a normal alkyl chain of 2 to 20 carbons. Preferably, the arms include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups such as oxy, thio, amino or chemically blocked derivatives thereof (e.g., trifluoroacetamido, phthalimido, CONR', NR'CO, and $SO_2NR'$, where R'=H or $C_{1-6}$alkyl). Such functionalities, including aliphatic or aromatic amines, exhibit nucleophilic properties and are capable of serving as a point of attachment to such groups as —$(CH_2)_m$-L, and —CO—$(CH_2)_m$—$(X)_n$—$N(R_1)$—$(CH_2)_p$-L which are described above as components of exemplary cross-linking functional groups.

After the nucleoside or nucleotide unit which carries the crosslinking functionality A-L, or a suitable precursor thereof, (such as the —$(CH_2)_q$—$NH_2$ or —$(CH_2)_q$—Y group, where Y terminates with a nucleophilic group such as $NH_2$) is prepared, further preparation of the modified oligonucleotides of the present invention can proceed in accordance with state of the art. Thus, to prepare oligonucleotides, protective groups are introduced onto the nucleosides or nucleotides and the compounds are activated for use in the synthesis of oligonucleotides. The conversion to protected, activated forms may follow the procedures as described for 2'-deoxynucleosides in detail in several reviews. See, Sonveaux, *Bioorganic Chemistry*, 14:274-325 (1986); Jones, in "Oligonucleotide Synthesis, a Practical Approach", M. J. Gait, Ed., IRL Press, p. 23-34 (1984).

The activated nucleotides are incorporated into oligonucleotides in a manner analogous to that for DNA and RNA nucleotides, in that the correct nucleotides will be sequentially linked to form a chain of nucleotides which is complementary to a sequence of nucleotides in target DNA or RNA. The nucleotides may be incorporated either enzymatically or via chemical synthesis. The nucleotides may be converted to their 5'-$\underline{O}$-dimethoxytrityl-3'-($\underline{N},\underline{N}$-diisopropyl)phosphoramidite cyanoethyl ester derivatives, and incorporated into synthetic oligonucleotides following the procedures in "Oligonucleotide Synthesis: A Practical Approach", supra. The $\underline{N}$-protecting groups are then removed, along with the other oligonucleotide blocking groups, by post-synthesis aminolysis, by procedures generally known in the art.

In a preferred embodiment, the activated nucleotides may be used directly on an automated DNA synthesizer according to the procedures and instructions of the particular synthesizer employed. The oligonucleotides may be prepared on the synthesizer using the standard commercial phosphoramidite or H-phosphonate chemistries.

A moiety containing the leaving group, such as a haloacyl group, or —CO—$(CH_2)_m$—$(X)_n$—$N(R_1)$—$(CH_2)_p$-L group (even more preferably a CO—$(CH_2)_3$—$C_6H_4$—N—$[CH_2CH_2Cl]_2$) may be added to the aminoalkyl or like tails (—$(CH_2)_q$—Y) following incorporation into oligonucleotides and removal of any blocking groups.

In the situations where the cross linking agent (A-L moiety) is attached to the 3' or 5' terminus of the oligonucleotide, for example by an alkylamine linkage of the formula -$(CH_2)_q$—Y (Y terminating in an amine), the oligonucleotide synthesis may be performed to first yield the oligonucleotide with said aminoalkyl tail, to which then an alkylating moiety, such as the above-noted haloacyl group or —CO—$(CH_2)_m$—$(X)_n N(R_1)$—$(CH_2)_p$-L is introduced.

An exemplary preferred embodiment of an ODN-MGB conjugate which has a cross-linking agent attached to one of the nucleotide bases is represented by the formula below:

5'-GGTTATTTTTGAAGATACGAATTTC$\underline{U}$CCAGAGACACAGCAGGATTTG

TCA-CDPI$_3$ where the underlined symbol "$\underline{U}$" (the 26th nucleotide unit in the 50 mer) represents a 5-(3-aminopropyl)-2'-deoxyuridine which has a chlorambucil residue attached to the amino group. The symbol "CDPI$_3$" represents a minor groove binder moiety as described below in connection with Reaction Scheme 1. The 5-(3-aminopropyl)-2'-deoxyuridine component is incorporated into the ODN by using 5'-O-trityl-5-trifluoroacetamidopropyl-2'-deoxyuridine 3'-(N,N-diisopropyl-cyanoethyl-phosphoramidite in accordance with the procedure of Gibson, K. J., & Benkovic, S. J. (1987) Nucleic Acids Res. 15, 6455. The chlorambucil residue and the minor groove binder moiety are reintroduced into the ODN as described in the experimental section below.

Synthesis of Minor Groove Binder Moieties and ODN-MGB Conjugates

Presently most preferred embodiments of the minor groove binder moieties of the present invention are "oligopeptides" derived from 1,2-dihydro-3$\underline{H}$-pyrrolo-[3,2-$\underline{e}$]indole-7-carboxylic acid (CDPI) and from 4-amino-$\underline{N}$-methyl-pyrrole-2-carboxylic acid. These are synthetic peptides which have repeating units of the structures shown respectively in Formula 2 and Formula 4 where the degree of polymerization (m) of the peptide is preferably 3 to 5, most preferably 5 for the peptide of Formula 2 and 3 for the peptide of Formula 4. Reaction Scheme 1 discloses a process for preparing a specific tripeptide abbreviated "CDPI$_3$" which thereafter can be coupled with or without minor modification, to ODNs, to form preferred embodiments of the ODN-MGB conjugates of the present invention.

Reaction Scheme 1
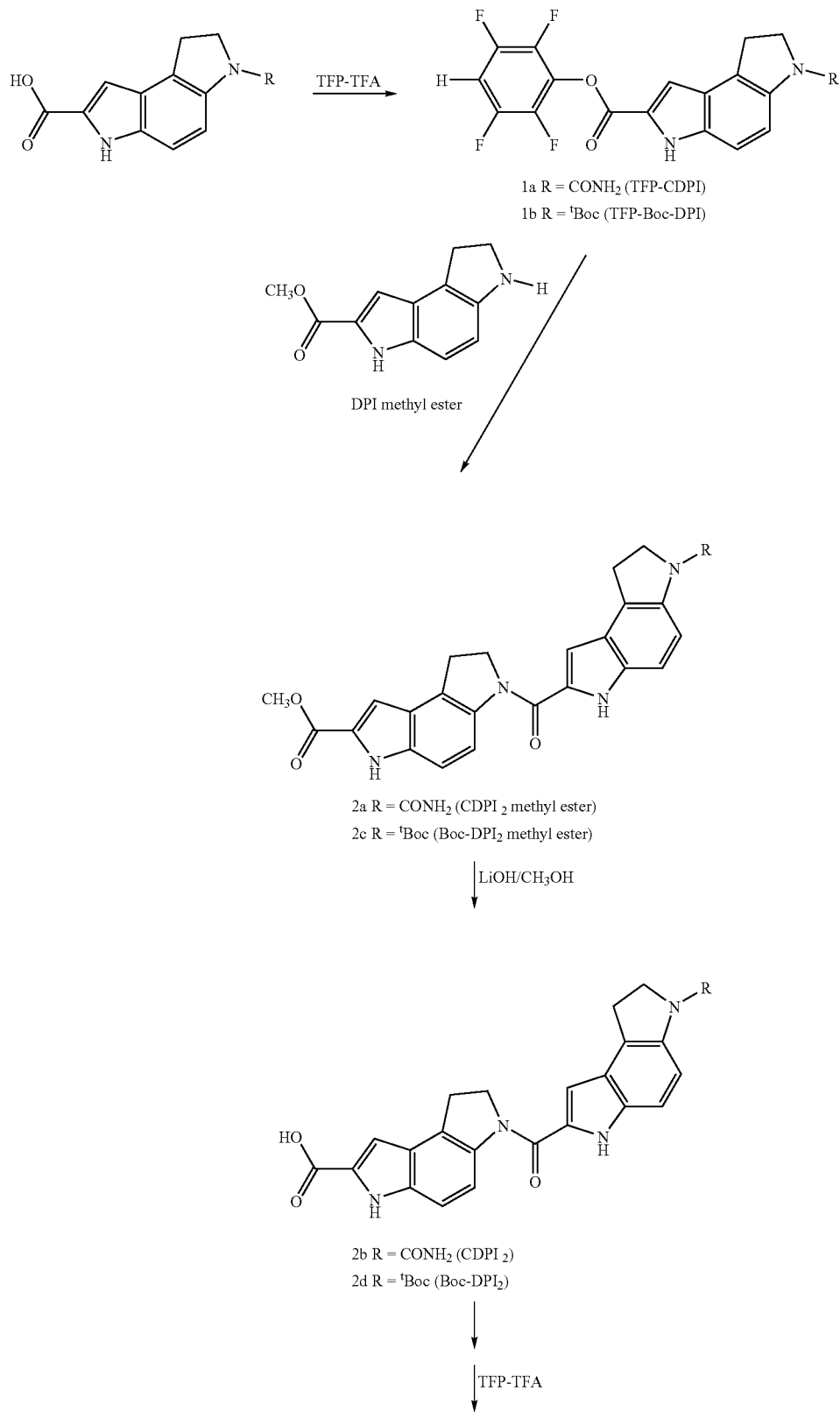

-continued
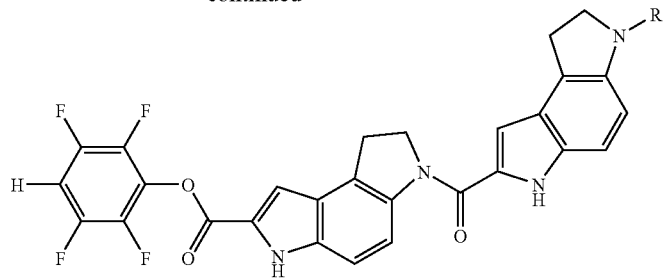
2e R = CONH₂ (TFP-CDPI₂)
2f R = ᵗBoc (TFP-Boc-DPI₂)
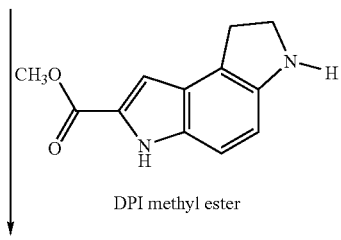
DPI methyl ester
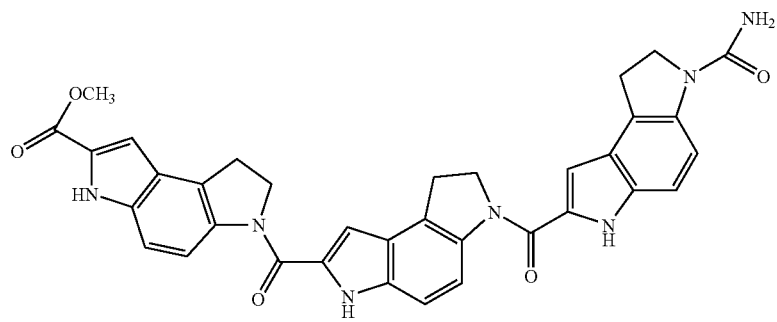
3a CDPI₃ methyl ester
| LiOH/CH₃OH
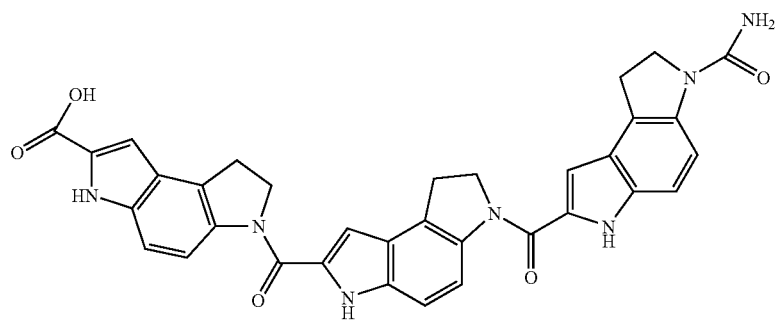
3b CDPI₃
| TFP-TFA -continued

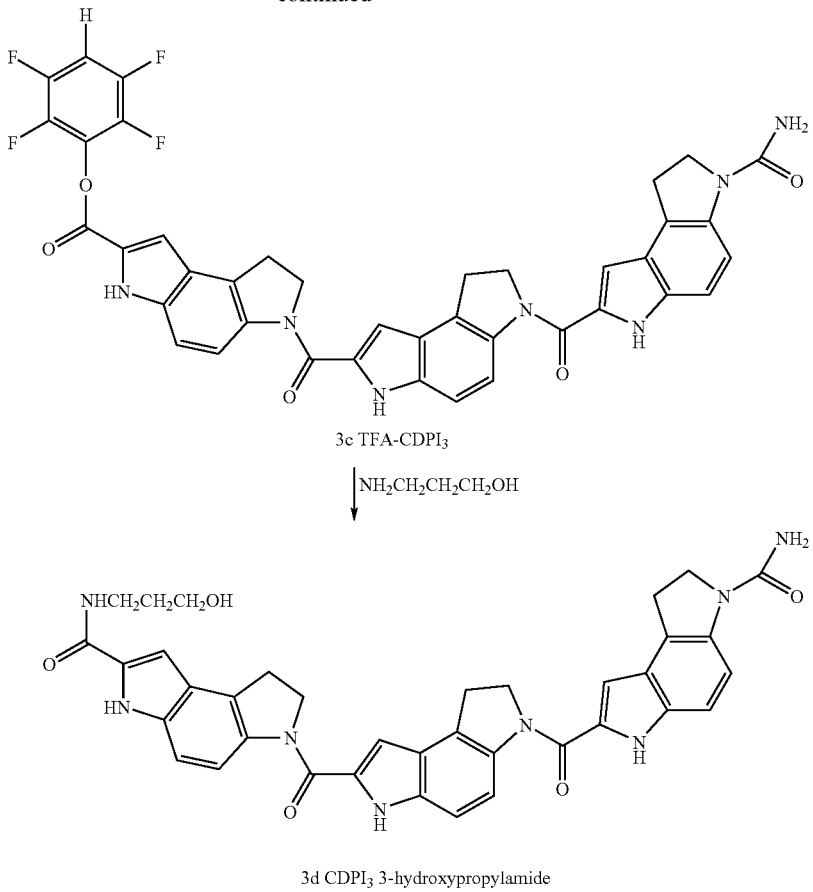

3c TFA-CDPI₃

3d CDPI₃ 3-hydroxypropylamide

Referring thus to Reaction Scheme 1, the starting material in this synthetic scheme is 3-carbamoyl-1,2-dihydro-3H-pyrrolo[3,2-e]indole-7-carboxylic acid or 3-t-butyloxycarbonyl-1,2-dihydro-3H-pyrrolo[3,2-e]indole-7-carboxylic acid which can be made in accordance with the chemical literature (D. L. Boger, R. S. Coleman, and B. J. Invergo. *J. Org. Chem.*, 1987, Vol. 52, 1521-1530). The starting compounds are converted into an active ester by treatment with the tetrafluorophenyl ester of trifluoroacetic acid (TFP-TFA). In compound 1a shown in the scheme the R group is $CONH_2$, in 1b R is t-butyloxycarbonyl ($^t$Boc). The t-butyloxycarbonyl ($^t$Boc) group is a well known protecting group for amino functions which can be removed by acid. The resulting activated esters 1a and 1b are reacted with methyl 1,2-dihydro-3H-pyrroloindole-7-carboxylate (also available in accordance with the chemical literature, see D. L. Boger, R. S. Coleman, and B. J. Invergo. *J. Org. Chem.*, 1987, Vol. 52, 1521-1530) to yield the "dimer" peptide compounds 2a and 2e. The methyl group of the carboxyl function is removed by treatment with base to yield the "dimer" peptides wherein the carboxylic acid group is free. This dimer is activated once more to form an active ester with tetrafluorophenol (2e when R=$CONH_2$', TFP-CDPI₂; and 2f when R=$^t$Boc, TFP-$^t$Boc-CDPI₂). After activation with TFP-TFA the active ester of the dimer can be used for forming the ODN-MGB conjugate as is described below in connection with the corresponding trimer. The activated ester of the dimer peptide can also be reacted with yet another molecule of methyl 1,2-dihydro-3H-pyrroloindole-7-carboxylate to form a "trimer peptide" that has its carboxylic acid function protected as a methyl ester, 3a (methyl 3-carbamoyl-11,2-dihydro-3H-pyrrolo[3,2-e]indole-7-carboxylate trimer). The methyl group is removed by treatment with base and the resulting "trimer peptide" 3b is converted again into an active tetrafluorophenyl ester 3c (2,3,5,6-tetrafluorophenyl 3-carbamoyl-1,2-dihydro-3H-pyrrolo[3,2-e]indole-7-carboxylate trimer, TFP-CDPI₃). The active tetrafluorophenyl ester 3c can be used to further lengthen the peptide chain by repeating the steps of reacting with methyl 1,2-dihydro-3H-pyrroloindole-7-carboxylate, saponifying the resulting methyl ester, and if desired, reacting with TFP-TFA again to make the active tetrafluorophenyl ester of the peptide incorporating 4-CDPI moeieties. As it will be readily understood, these steps can be repeated further until the desired number of CDPI Moieties are included in the peptide. In the herein described preferred embodiments the active tetrafluorophenyl ester of the tripeptide 3c (TFP-CDPI₃) is utilized for coupling to an ODN to make an ODN-MGB, or for synthesizing an ODN-MGB on a suitable modified controlled pore glass (CPG) solid support as is described below in connection with Reaction Schemes 4 and 5. Reaction Scheme 1 indicates as its last step the preparation of a hydroxylpropylamide derivative from the active tetrafluorophenyl ester of the tripeptide 3c (TFP-CDPI₃). The hydroxylpropylamide derivative of the tripeptide 3d (3-carbamoyl-1,2-dihydro-3H-pyrrolo[3,2-e]indole-7-carbox]-1-amido-3-propanol trimer, CDPI₃-3-hydroxylpropylamide) can be used for coupling with an ODN to obtain an ODN-MGB in accordance with the present invention. The tripeptide 3d however, was also used as a "free standing" minor groove binder molecule as a control in certain binding studies which are described below.

Reaction Scheme 2
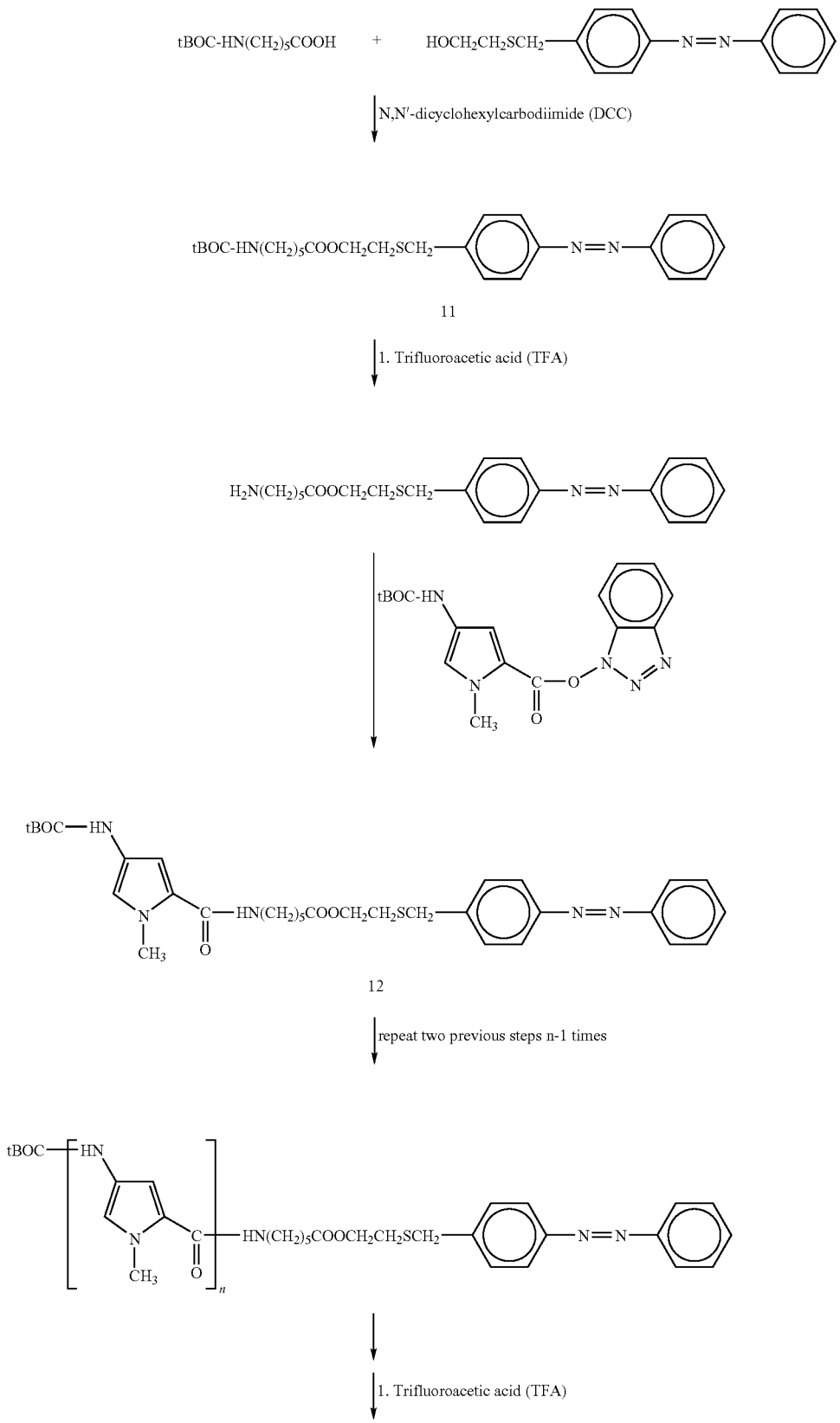

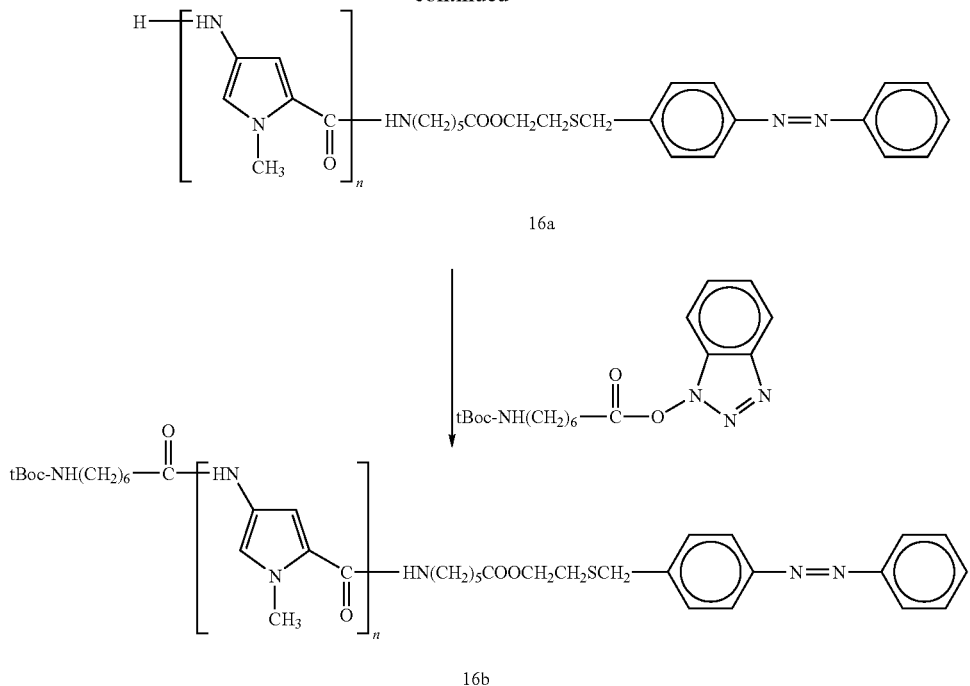

16a

16b

Referring now to Reaction Scheme 2 the synthesis of another preferred embodiment of the minor groove binder peptides is disclosed, where the "monomer" is the residue of 4-amino-N-methylpyrrol-2-carboxylic acid, and which embodiment also bears a reporter group/containing a diazobenzene moiety. Thus, in accordance with this scheme 6-[(tert-butyloxy)carboxamido]hexanoic acid is condensed in the presence of N,N-dicyclohexylcarbodiimide with 2-[4-(phenylazo)-benzylthio]-ethanol to form (2-[4-(phenylazo) benzylthio]ethyl 5-(tert-butyloxy) carboxamido]pentylcarboxylate, 11). The ′Boc protecting group is removed from compound 11 by treatment with trifluoroacetic acid (TFA) and the resulting compound having a free amino function is reacted with an activated ester of ′Boc protected 4-amino-N-methylpyrrol-2-carboxylic acid. The latter activated ester compound (1,2,3-benzotriazol-1-yl 1-methyl-4-(tert-butyloxy)carboxamido-pyrrole-2-carboxylate) is made from 1-methyl-4-[tertbutyloxy)carboxamido]pyrrole-2-carboxylic acid which is available pursuant to the literature procedure of L. Grehn, V. Ragnarsson, *J. Org. Chem.*, 1981, 46, 3492-3497. The resulting 2-[4-(phenylazo)benzylthio]ethyl 5-[1-mdthyl-4-(tert-butyloxy)carboxamido]pyrrole-2-carboxamido]pentylcarboxylate, 12) has one unit of the monomer "2-amino-N-methylpyrrol carboxylic acid" residue attached to the reporter group that carries the diazobenzene moiety. After removal of the ′Boc protecting group with trifluoroacetic acid and coupling with one or more molecules of 1,2,3-benzotriazol-1-yl 1-methyl-4-(tert-butyloxy)carboxamidopyrrole-2-carboxylate can be accomplished, until a peptide containing the desired number of monomer residues is obtained. Such a compound having n number of monomers and a free amino group is indicated in Reaction Scheme 2 as 16a. Compound 16a can be reacted with an activated ester (such as a 1,2,3-benzotriazol-1-yl activated ester) of ′Boc protected 6-aminohexanoic acid to provide the oligopeptide shown as compound 16b in Reaction Scheme 2. The ′Boc protecting group can be removed from the latter compound under acidic conditions, and the resulting derivative having a free amino function can be attached by conventional synthetic methods to either the 3'-phosphate or 5'-phosphate end of an ODN. Alternatively, the derivative having a free amino function can also be attached to the 3' or 5'-OH end of an oligonucleotide using a variety of bifunctional linking groups, as discussed above.

Reaction Scheme 3

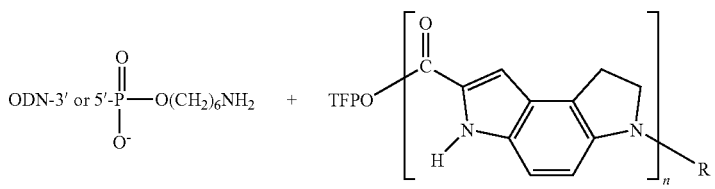

1a n = 1 R = CONH$_2$
1b n = 1 R = tBOC
2e n = 2 R = CONH$_2$
2f n = 2 R = tBOC
3c n = 3 R = CONH$_2$

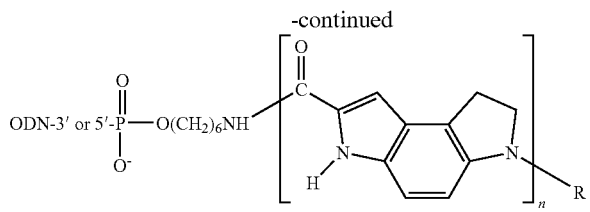

Referring now to Reaction Scheme 3a general method for coupling a 3'-amino tailed or 5'-aminotailed ODN with the tetrafluorophenyl (TFP) ester activated exemplary minor groove binding oligopeptides is illustrated. Although the scheme shows the use of the TFP activated exemplary minor groove binding compounds obtained in accordance with Reaction Scheme 1, it should be kept in mind that this general method is suitable for the coupling of other TFP activated minor groove binding compounds with ODNs, as well. The reference numeral 1a through 3c in Reaction Scheme 3 refer to the exemplary compounds obtained in accordance with Reaction Scheme 1.

The 3'- or 5'-amino tailed ODNs can be synthesized by conventional methods; for example an aminohexyl residue can be attached to either end of the ODN by using commercially available N-monomethoxytritylaminohexyl phosphoramidite. Alternatively, the amino tailed ODNs can be synthesized in accordance with the methods described in U.S. Pat. No. 5,419,966, the disclosure of which is expressly incorporated herein by reference. In accordance with the present scheme the amino tailed ODN is converted into a cetyltrimethylammonium salt to render it soluble in organic solvents, and the tetrafluorophenyl ester activated minor groove binder molecule is condensed therewith, preferably in DMSO as a solvent.

Reaction Scheme 4

CPG, bearing 5'-amino tailed ODN

| 1. TFP CDPI$_3$ (3c Scheme 1)
| 2. conc. NH$_3$

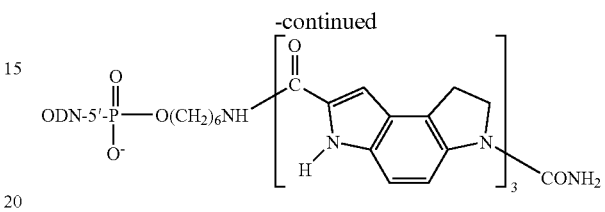

Reaction Scheme 4 discloses another method of coupling an active ester of a minor groove binder molecule to a 5'-amino tailed ODN. The example shown in the scheme is that of the TFP ester of the tripeptide derived from 3-carbomoyl-1,2-dihydro-3Hpyrrolo[3,2-e]indole-7-carboxylic acid residues (TFP-CDPI$_3$) but it should be understood that the generic principles disclosed in connection with this reaction scheme can be used with other minor groove binder molecules as well. In this method, the ODNs still attached to a CPG support, and has a free amino group on its "amino tail". This can be obtained by using N-monomethoxytritylazinohexyl phosphoramidite mentioned above. The monomethoxytrityl group is removed after the coupling of the phosphoramidite to give the desired CPG-bearing-"amino-tailed ODN". Alternatively, such a CPG can be obtained in accordance with the disclosure of U.S. Pat. No. 5,419,966, and references cited therein. By way of summary, the ODN is synthesized stepwise attached to the CPG, and having a tail having an amino group protected with a 9-fluorenylmethoxycarbonyl (Fmoc) group. After the desired sequence of nucleotides has been built up, the Fmoc group is removed from the amino group while the ODN is still attached to the CPG support. In accordance with Reaction Scheme 4 of the present invention this "CPG-bearing-amino-tailed-ODN" having the free amino group is condensed with the active ester (TFP-CDPI$_3$, 3c) or with a like activated form of a minor groove binder. The ODB-MGB conjugate is thereafter removed from the CPG support by conventional methods, most frequently by treatment with ammonia.

Reaction Scheme 5

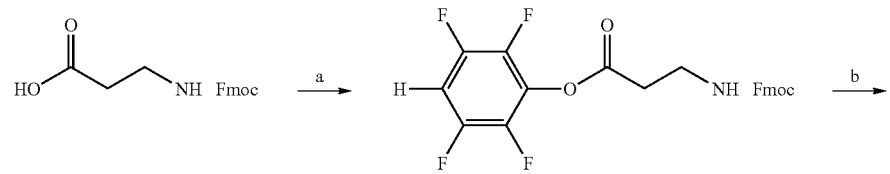

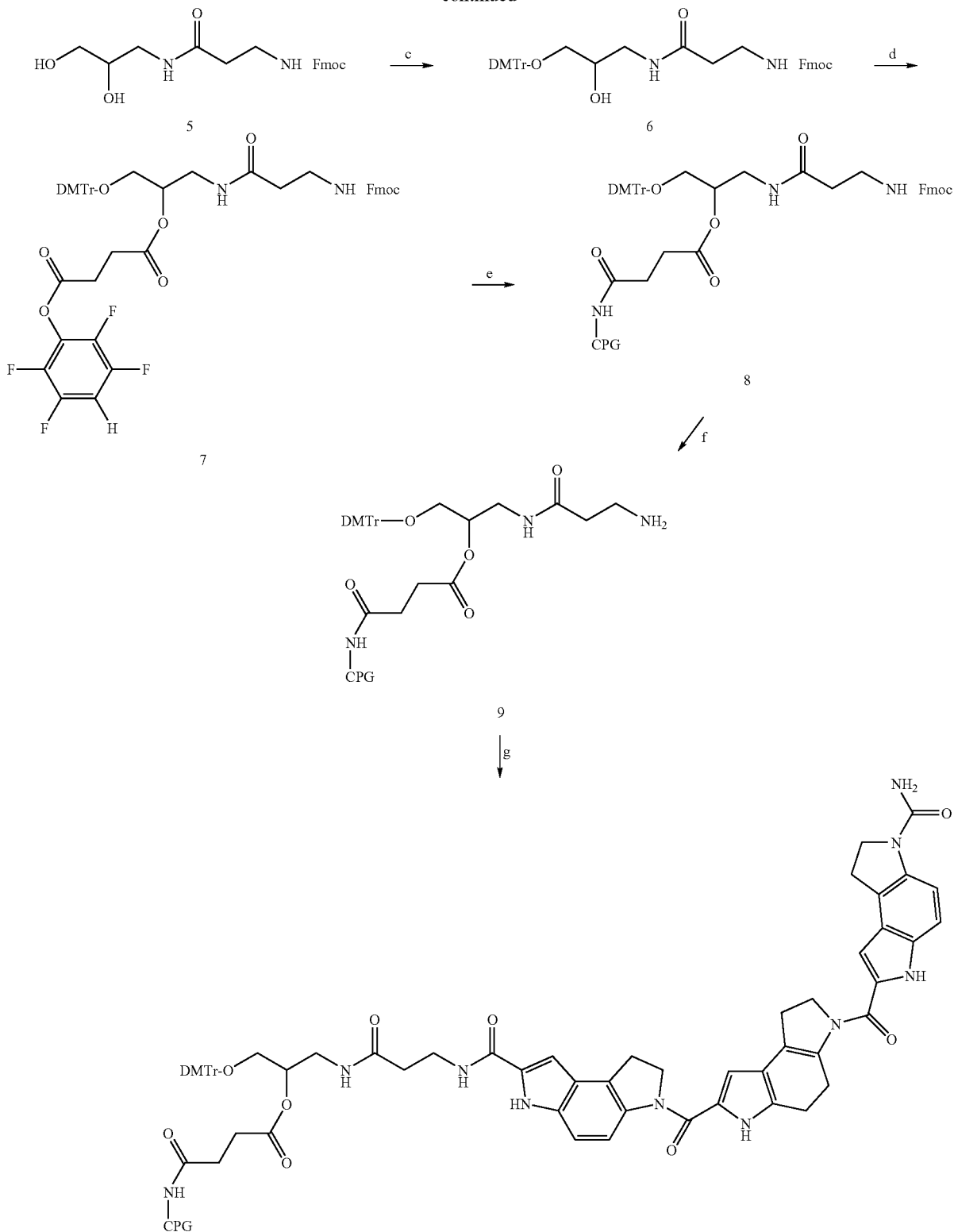
*Reagents: (a) TFP-TFA, Et$_3$N, CH$_2$Cl$_2$; (b) 3-amino-1,2-propanediol, CH$_2$Cl$_2$; (c) DMTrCl, pyridine; (d) succinic anhydride, N-methylimidazole, CH$_2$Cl$_2$, TFP-TFA; (e) Alkyl amine CPG, pyridine; (f) piperidine, DMF; (g) TFP-CDPI$_3$ (3c Scheme 1), DMF.

Reaction Scheme 5 discloses another preferred method for preparing, the ODN-MGBs of the present invention. More particularly, Reaction Scheme 5 discloses the preferred synthetic process for preparing ODN-MGBs by first attaching a linking molecule to a CPG support, thereafter attaching an activated form of minor groove binder to the linking molecule, and thereafter building the ODN of desired sequence step-by-step in an automatic ODN synthesizer using the just described modified CPG support. The ODN-MGB conjugate is removed from the CPG support only after the ODN moiety of desired sequence has been completed. The linking molecule in this case is a trifunctional molecule, with each function having different reactivity, which permit attachment to the CPG, reaction with the activated form of minor groove binder moiety and the building of the ODN portion, each using a different functionality of the linking molecule. A more general and detailed description of this synthetic method and of the trifunctional linking molecules which can be utilized in the method, but without any reference to minor groove binders, can be found in U.S. Pat. No. 5,419,966, the disclosure of which is expressly incorporated herein by reference. Reaction Scheme 5 illustrates this synthetic process with the example of β-alanilyl-3-amino-1,2-propanediol as the trifunctional linking molecule, and TFP-CDPI$_3$ (compound 3c) as the activated form of the minor groove binder.

Thus in accordance with Reaction Scheme 5, Fmoc protected β-alanine is reacted with tetrafluophenyl trifluoroacetate (TFP-TFA) to provide 2,3,5,6-tetrafluorophenyl 3-[N-(9-fluorenylmethoxycarbonyl)]aminopropionate (4). The active ester 4 is reacted with 3-amino-1,2-propanediol to provide 1-[3-[N-(9-fluorenylmethoxycarbonyl)amino]-1-oxopropyl]amino-(R,S)-2,3-propanediol (5). The primary hydroxyl group of 5 is thereafter protected with a dimethoxytrityl group to give 1-[3-[N-(9-fluorenylmethoxycarbonyl)amino]-1-oxopropyl]amino-(R,S)-2-[[bis(methoxyphenyl)phenylmethoxy]methyl]-2-ethanol (6). The secondary hydroxyl group of compound 6 is reacted with succinic anhydride and the carboxylic group in the resulting compound is thereafter converted into an active ester, 2,3,5,6-tetrafluorophenyl 1-[3-[N-(9fluorenylmethoxycarbonyl)amino]-1-oxopropyl]amino(R,S)-2-[[bis(methoxyphenyl)phenylmethoxy)methyl]-2-ethyl butanedioate (7). Compound 7 is then attached to a long chain aminoalkyl controlled pore glass support (LCAA-CPG, or alkylamine CPG) which is commercially available and is described in the above-cited U.S. Pat. No. 5,419,966. The resulting "modified CPGII is shown in Reaction Scheme 5 as Compound 8. The Fmoc protecting group is removed from 8 by treatment with mild base (piperidine in dimethylformamide) to yield the "modified CPG" 9 that has a free primary amine function as part of the linking molecule. In the next step the activated minor groove binder molecule, in this instance TFP-CDPI$_3$ (compound 3c) is reacted with the primary amine function of 9, to yield the modified CPG 10 that includes the minor groove binder moiety and still has the primary hydroxyl group of the linking group protected with a dimethoxytrityl group. Although this is not shown in Reaction Scheme 5, in the subsequent steps the dimethoxytrityl group is removed and the ODN synthesis is performed in an automatic synthesizer, by steps which are now considered conventional in the art.

When the synthesis is complete the ODN-MGB conjugate is removed from the CPG support by treatment with ammonia. The latter step cleaves the bond attaching the secondary hydroxyl group of the 3-amino-1,2-propanediol moiety to the CPG support.

Biological Testing and Discussion

The ODN-MGB conjugates bind to single stranded DNA. They also bind to double stranded DNA in the presence of a recombinase enzyme, and in some cases to single stranded RNA and DNA and RNA hybrids as well. The binding however occurs only if the ODN moiety is complementary, or substantially complementary in the Watson-Crick sense, to a target sequence in the target DNA or RNA. When this condition is met, the binding of the ODN-MGB to the target sequence is significantly stronger than binding of the same ODN would be without the minor groove binder. The foregoing is demonstrated by the tests described below, and provides utility for the ODN-MGB conjugates of the present invention as analytical and diagnostic hybridization probes for target DNA or RNA sequences, and in therapeutic antisense and anti-gene applications.

TABLE 1

$T_m$'s data of the (dAp)$_8$ + (dTp)$_8$ duplex carrying intercalators or oligo-(1-methyl-2-carboxy-4amino)pyrrole residues attchcd to 3'-end of the ODN.[a]

| COMPLEX | | $T_m$ | $\Delta T_m$[b] |
|---|---|---|---|
| (dAp)$_8$ + (dTp)$_8$ | | 21.1 | — |
| (dAp)$_8$ + (dTp)$_8$ + Distamycin A[c] | | 47.1 | 26.0 |
| (dAp)$_8$ + (dTp)$_8$-X$_m$ | m = 2 | 39.4 | 18.3 |
| | m = 3 | 51.7 | 30.6 |
| | m = 4 | 60.2 | 39.1 |
| | m = 5 | 65.4 | 44.3 |
| (dTp)$_8$ + (dAp)$_8$-X$_m$ | m = 2 | 29.1 | 8.0 |
| | m = 3 | 39.0 | 17.9 |
| | m = 4 | 42.7 | 21.6 |
| | m = 5 | 52.6 | 31.5 |
| (dAp)$_8$-Y + (dTp)$_8$ | | 30.5 | 9.4 |
| (dAp)$_8$-Y + (dTp)$_8$-Y[d] | | 42.9 | 21.8 |

[a]Reported parameters are averages of at least three experiments. Optical melts were conducted in 0.2 M NaCl, 0.3 mM EDTA, 0.01 M (±0.1° C.) Na$_2$HPO$_4$, pH 7.0 with [(dTp)$_8$•(dAp)$_8$] = 2.5•10$^{-5}$ M.
[b]The difference in $T_m$ between modified and unmodified duplexes.
[c]Concentration of distamycin A was 2.5•10$^{-5}$ M.
[d]Ethidium bromide (EtBr) was conjugated by its 8-NH$_2$-position to the 3'-terminal phosphate of the ODNs through a β-alanine linker by the method in ref 12.

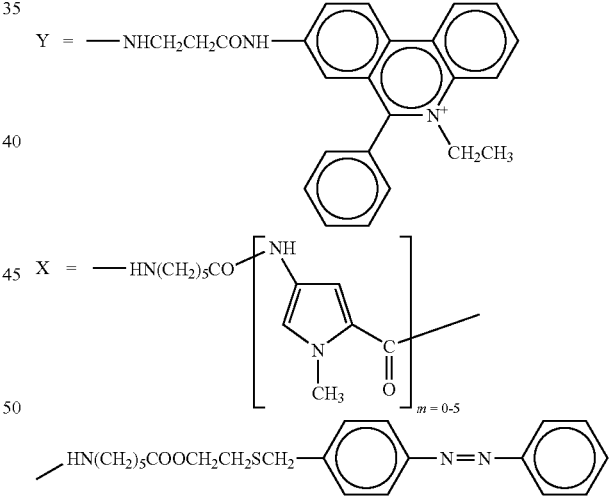

Table 1 illustrates the melting temperature of several complexes formed of complementary oligonucleotides which have the minor groove binder moiety derived from 4-amino-N-methylpyrrol-2-carboxylic acid residues. The minor groove binder moiety is specifically shown as the radical X by the formula below Table 1. It is noted that the radical X also includes a linking moiety which is derived from 6-aminohexanoic acid. The oligonucleotides utilized here are 8-mers of 21deoxyadenylic acid, and 8-mers of thymidylic acid. The minor groove binder X is attached to the ODNs at the 3'-phosphate end, the 5'-end of these ODNs have no phosphate. In this regard it is noted that the ODNs are abbreviated in these and the other tables in the manner customary in the art. The group Y symbolizes an ethidium bromide moiety attached to the 3'phosphate end through a "β-alanine" linking moiety. The Y group represents an intercalating group and acts as a control for comparison with the minor groove binding groups. The symbol a represents the number of 4-amino-N-methylpyrrol-2-carboxylic acid residues present in each ODN-MGB of the table.

As is known in the art, the melting temperature ($T_m$) of an oligonucleotide or polynucleotide duplex is defined as that temperature at which 50% of the respective oligonucleotide or polynucleotide is dissociated from its duplex, Watson Crick hydrogen bonded form. A higher melting temperature ($T_m$) means a more stable duplex. As is known further, the melting temperature of an oligonucleotide or polynucleotide is dependent on the concentration of the nucleotide in the solution in which the melting temperature is measured, with higher concentrations resulting in higher measured melting temperatures. The melting temperatures indicated in these tables were measured under conditions indicated in the table and in the experimental section. $\Delta T_m$ represents the change in melting temperature of the modified duplex relative to the melting temperature of the $(dAp)_8.(dTp)_8$ complex which has no minor groove binder moiety.

As it can be seen from Table 1, the covalently bound minor groove binder moiety significantly increases the stability (melting temperature $T_m$) of the complex, whether the group X (minor groove binder moiety) is attached to the $(dTp)_8$ or to the $(dAp)_8$ oligonucleotide. In this instance the greatest degree of stabilization (highest melting temperature) is achieved when the minor groove binder moiety is a 5-mer oligopeptide. In the comparative experiment when the intercalating group Y is attached to the $(dAp)_8$ oligomer, a comparatively much smaller degree of stabilization is attained. Even attaching the intercalating Y group to each of the two strands of oligomers in this experiment, raised the melting temperature less than the minor groove binder moiety having five 4-amino-N-methylpyrrol-2-carboxylic acid residues.

TABLE 2

$T_m$'s data of the duplexes formed by hexadeca-, octathymidylate and their oligo-(1-methyl-2-carboxy-4amino)pyrrole derivatives with polydeoxyriboadenylic acid in 0.2 M NaCl, 0.01 M na$_2$HPO$_4$, 0.1 mM EDTA (pH7.0). X is same as Table 1.

| Oligo Derivative | | $T_m$ °C. | $\Delta T_m$ °C. |
|---|---|---|---|
| $(dTp)_{16}$ | | 48.5 | — |
| $(dTp)_{16}$-NH(CH$_2$)$_5$COOH | | 49 | 0.5 |
| $(dTp)_{16}$-X | m = 1 | 49.3 | 0.8 |
| | m = 2 | 55.6 | 7.1 |
| | m = 3 | 61 | 12.5 |
| | m = 4 | 66 | 17.5 |
| | m = 5 | 68 | 19.5 |
| $(dTp)_8$ | | 28 | — |
| $(dTp)_8$-X | m = 1 | 28 | 0 |
| | m = 2 | 40 | 12 |
| | m = 3 | 52 | 24 |
| | m = 4 | 60 | 32 |
| | m = 5 | 66 | 38 |

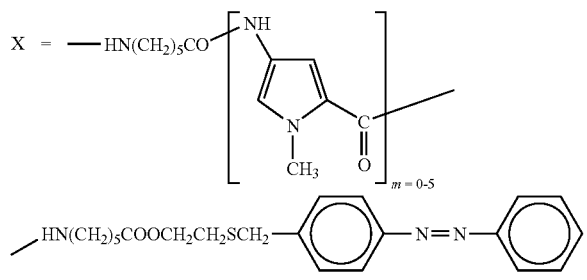

Table 2 discloses information in a manner similar to Table 1. In the tests reported in this table 16-mer ODNs of thymidylic acid having the minor groove binder moiety represented by X (X is the same as in Table 1) were complexed with polydeoxyriboadenylic acid. As a comparative control a 16 mer ODN of thymidylic acid $(dTp)_{16}$ connected at its 3'-phosphate end to 6-aminohexanoic acid was also tested. Additionally an 8-mer of thymidylic acid $(dTp)_8$ and its conjugates with the minor groove binders of varying peptide length were also tested. In these tests too, the minor groove binder attached to the ODN causes significant stabilization of the complex between the ODN-MGB and the complementary DNA strand. Greatest stabilization occurs when the number of 4-amino-N-methylpyrrol-2-carboxylic acid residues in the minor groove binder moiety is five. In contrast, the aminohexanoic acid tail on the 16-mer ODN results in virtually no stabilization of the complex.

TABLE 3

Melting temperatures (° C.) of duplexes formed by poly(dA) and poly(rA) with $(Tp)_8$ strands terminallylinked to CDPI$_{1-3}$ and BocDPI$_{1-2}$ ligands.[a]

| Octathymidylate derivative | | poly(dA) | | poly(rA) | |
|---|---|---|---|---|---|
| | | $T_m$ | $\Delta T_m$ | $T_m$ | $\Delta T_m$ |
| $(dTp)_7 dTp$-L1 | | 25 | — | 13 | — |
| $(dTp)_7 dTp$-L1-X | m = 1 | 34 | 9 | 18 | 5 |
| $(dTp)_7 dTp$-L1-X | m = 2 | 50 | 25 | —[b] | — |
| $(dTp)_7 dTp$-L1-X | m = 3 | 68(65) | 43(40) | 32(31) | 19(18) |
| $(dTp)_7 dTp$-L1-Y | m = 1 | 26 | 1 | 12 | −1 |
| $(dTp)_7 dTp$-L1-Y | m = 2 | 43 | 18 | 17 | 4 |
| L1-pdT(pdT)$_7$ | | 24 | — | 12 | — |
| X-L1-pdT(pdT)$_7$ | m = 1 | 31 | 7 | 14 | 2 |
| X-L1-pdT(pdT)$_7$ | m = 2 | 49 | 25 | —[b] | — |
| X-L1-pdT(pdT)$_7$ | m = 3 | 68 | 44 | 35 | 23 |
| Y-L1-pdT(pdT)$_7$ | m = 1 | 23 | −1 | 9 | −3 |
| Y-L1-pdT(pdT)$_7$ | m = 2 | 41 | 17 | 19 | 7 |

[a]The data in brackets were obtained for the derivative with linkder L2.
[b]No melting transition was observed.

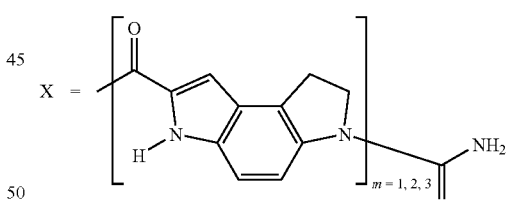

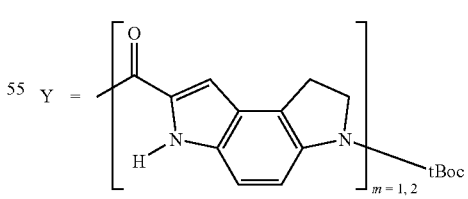

Table 3 discloses melting temperature ($T_m$) and change in melting temperature ($\Delta T_m$) data in tests where the oligonucleotide is an 8-mer of thymidylic acid having a minor groove binder moiety attached to it either at the 5'-phosphate or 3'-phosphate end, as indicated in the table. The minor groove binder moieties represented here by X and Y are "oligopeptides" based on the residue of 1,2-dihydro-3 Hpyrrolo[3,2-e]indole-7-carboxylic acid (CDPI or BocDPI) and their structures are shown in the table. These minor groove binding oligopeptides are attached to the ODN through a linking moiety "L1 or L2" the structures of which are also shown below the table. The ODN-MGB conjugates were incubated with a complementary ribo- or deoxyribo homopolymer. Thus for ODN-MGB conjugates comprising ODNs of thymidylic acid, poly A or poly-dA was used. The change in melting temperature ($\Delta T_m$) is indicated relative to the complex with the ODN which bears the corresponding linking group L1 or L2 in the corresponding end of the ODN, but bears no minor groove binding moiety. As it can be seen from Table 3, these ODN-MGB complexes again exhibit significant stabilization of the complex with the complementary deoxyribo homopolymer, with the greatest stabilization occurring in these tests when the minor groove binding moiety has 3 CDPI units. Surprisingly, stabilization of the complex occurs even when the ODN-MGB is incubated with a complementary ribohomopolymer. This is surprising because it had been generally observed in the prior art that free standing minor groove binding molecules do not bind to DNA-RNA hybrids.

Table 4 discloses results of a study of duplex formation between derivatives of two complementary octamers: CpApTpCpCpGpCpT and ApGpCpGpGpApTpG. Each octamer was modified, as shown in the table, so that hybridization of the corresponding oligodeoxyribonucleotides and of oligodeoxyribonucleotides having a phosphorothioate backbone were examined. The ODN also had the tripeptide based on the residues of 1,2-dihydro-3H-pyrrolo[3,2-e]indole-7-carboxylic acid (CDPI) (minor groove binder moiety X) attached either to the 3' or to the 5' end (as indicated) through a linking group of the structure L1 or L2. (X, L1 and L2 are the same as in Table 3.) As controls, the melting temperature of duplexes was also determined for duplexes where the ODNs bore only the linking groups. As it can be seen in the table, the duplexes are significantly stabilized by the presence of a minor groove binder moiety, and greater stabilization occurs when each strand of the duplex has a covalently bound minor groove binder.

TABLE 5

$T_m$'s data (° C.) of heterogeneous duplexes carrying 3'-oligo(pyrroloindole carboxamide) peptide residues.

| Complemenary | d(AGCGGATG)p | | d(AICILATI)p | |
|---|---|---|---|---|
| ODNs | 3'-L1— | 3'-L2—X | 3'-L1— | 3-L1—X |
| d(CATCCGCT)p 3'-L1— | 41 | 52 | 11 | — |
| 3'L2—X | 57 | 81 | 48 | 67 |

TABLE 4

$T_m$'s data (° C.) of heterogeneous duplexes phosphodiester and phosphorothioate backbones and oligo(pyrroloindole carboxainide) peptide residues attached to the different positions[a.]

| Derivative of CpApTpCpCpGpCpT | | Derivative of ApGpCpGpGpApTpG | | | | | | |
|---|---|---|---|---|---|---|---|---|
| | | DNA | | | | 3'-L2—X & 2'-DNA PS[c] | | |
| Type of Backbone | Type of terminal modification | 3'-L1— | 3'-L2—X | 5'-X—L1— | 5'-X—L1— none[b] | 5'-X—L1— | 3'-L2—X |
| DNA | 3'-LI— | 41 | 52 | 45 | 50 | 33 | 27 | 40 |
| | 3'-L2—X | 57 | 81 | 78 | 77 | 50 | 73 | 77 |
| | 5'-X—LI— | 58 | 79 | 76 | 76 | 49 | 70 | 75 |
| | 3'-L2—X 5'-XL1— | 60 | 72 | — | 65 | — | — | — |
| 2'-DNA PS[c] | none[b] | 32 | 43 | 32 | — | 24 | 16 | 28 |
| | 5'-X—L1 | 38 | 69 | 67 | — | 28 | 62 | 63 |
| | 3'-L2—X | 45 | 74 | 71 | — | 36 | 64 | 69 |

[a]Concentration of ODNs in the melting mixtures was $2 \times 10^{-6}$ M in 140 mM KCl, 10 mM $MgCl_2$, 20 mM HEPES-HCl (pH 7.2).
[b]The ODN has free 3'- and 5'-OH groups.
[c]PS is phosphorothioate linkage.

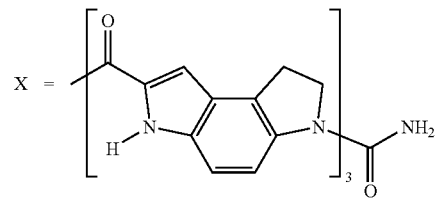

L1 = —O(CH$_2$)$_6$NH— L2 = —OCH$_2$CH(OH)CH$_2$NHCOCH$_2$CH$_2$NH—

TABLE 5-continued $T_m$'s data (° C.) of heterogeneous duplexes carrying
3'-oligo(pyrroloindole carboxamide) peptide residues.

| Complemenary | d(AGCGGATG)p | | d(AICILATI)p | |
|---|---|---|---|---|
| ODNs | 3'-L1— | 3'-L2—X | 3'-L1— | 3-L1—X |
| d(CATCCICT)p 3'-L1— | 31 | 48 | 0 | 41 |
| 3'L1—X | 54 | 79 | 48 | 63 |

$$X = \left[ \begin{array}{c} \text{O} \\ \text{pyrroloindole carboxamide structure} \end{array} \right]_3 \text{—NH}_2$$

L1 = —O(CH$_2$)$_6$NH—  L2 = —OCH$_2$CH(OH)CH$_2$NHCOCH$_2$CH$_2$NH—

Table 5 discloses melting temperature data obtained when complementary or "quasi complementary" ODN-MGB were incubated and examined for duplex formation. The minor groove binding moiety X and the linking groups L1 and L2 are shown in the table and are the same as in Tables 3 and 4. As anticipated, when guanine is replaced inosine (I) in the strands the binding of the duplexes is very weak ($T_m$ is approximately 0° C.) if there is no minor groove binding moiety present. However, when guanine is replaced by inosine in the oligonucleotides the presence of one covalently appended minor groove binder X stabilized the hybrid by almost 50° C. and the presence of two such minor groove binders in antiparallel orientation provided 63° C. of stabilization. When the same strands contained guanine, one minor groove binder increased,—) the $T_m$ by 15° C. while two increased it by nearly 45° C. To the knowledge of the present inventors a $T_m$ of 81° C. for an 8 mer is unprecedented in the prior art.

Primer Extension Experiment.

That sequence specificity in the Watson-Crick sense of the ODN portion of the ODN-MGB conjugate is required for complexing the ODN-MGB conjugate to a target sequence was demonstrated by a primer extension experiment. In this experiment, primer extension occurs with the enzyme T7 DNA polymerase that works from the 5' end of a template strand. A 16-mer ODN-MGB which was complementary in the Watson Crick sense to a target sequence on the template strand was incubated with a long single stranded DNA template and the T7 DNA polymerase enzyme. Blockage of the primer extension was noted at the site of binding with the ODN-MGB when the minor groove binding moiety was on the 5' end of the 16-mer ODN. The minor groove binder was the pyrroloindole tripeptide shown in this application in Table 5. When there was a single mismatch in the sequence specificity of the 16-mer to the target, primer extension was not blocked. Primer extension was also not blocked when the minor groove binder moiety was attached to the 3' end of the 16-mer. Primer extension was also not blocked when the sequence specific 16-mer and the free minor groove binder molecule (Compound 3d, not covalently attached to the ODN) was incubated with the template and the enzyme. These experiments show that sequence specificity of the ODN-MGB is important for complex formation, and that the minor groove binding moiety does not simply act as an "anchor" to non-specifically bind the appended ODN to another strand. The ability of ODN-MGB conjugates to inhibit primer extension indicates that these conjugates can be used diagnostically as polymerase chain reaction (PCR) clamping agents. (See Nucleic Acid Research (1993) 21: 5332-5336).

Slot-Blot Hybridization Assay

The ODN-MGB conjugates of the present invention are useful as hybridization probes. This is demonstrated by the description of the following experiment utilizing a $^{32}$P-labeled ODN-MGB conjugate as a diagnostic probe. When compared to the same ODN without a covalently linked minor groove binder (MGB) moiety, the conjugate hybridizes to its complement with greater strength, efficiency and specificity. The slot-blot hybridization assay is a widely used DNA probe diagnostic assay, and the attributes of these MGB-ODN conjugates improve the performance of the assay.

Specifically, in the herein described experiment a standard protocol was followed, as described in *Protocols for Nucleic Acid Blotting and Hybridization*, 1988, Amersham, United Kingdom. Labelled test ODN which hybridized to the immobilized plasmid was quantitated as counts per minute (cpm), and plotted vs temperature of hybridization. Four 16-mer probes complementary to M13mp19 DNA (a phage DNA) were evaluated. Two of these probes were totally complementary to a site in the phage DNA; one of these contained a 3'-conjugated CDPI$_3$ moiety while the other was unmodified. The second pair of probes were targeted to the same site in M13mp19 DNA but each contained a single mismatch (underlined in drawing FIG. 1). Here again, one ODN was 3'-conjugated to CDPI$_3$ while the other was unmodified.

The results of the slot hybridization study are shown in FIG. 1. Compared to an unmodified but otherwise identical 16-mer, the CDPI$_3$-containing probe formed a hybrid with a melting temperature ($T_m$) of 50° C. versus only 33° C. This higher melting temperature more than doubled the yield of perfectly matched hybrids. When a mismatch was introduced into either probe, stability of the respective hybrids dropped. The CDPI$_3$-modified probes exhibited good sequence discrimination between 37°-50° C. Furthermore, under the hybridization conditions used here there was no evidence for binding of the CDPI$_3$ moiety to preexisting double-stranded regions in the M13mp19. DNA target, indicating that totally non-specific binding of these conjugates is not present.

Sequence-Specific Alkylation of a Gene in Cultured Human Cells

The ODN-MGB conjugates of the present invention which also bear a covalently attached alkylating agent can be used as "anti-gene" agents, that is for the suppression of the expression of undesired (disease causing) genes, provided the ODN-MGB conjugate is complementary to a target sequence in the target gene. In such a case the NGB moiety improves the binding to the double stranded gene (in the presence of a recombinase enzyme) and the alkylating moiety results in permanent covalent binding of the ODN-MGB conjugate to the target sequence.

As a demonstrative experiment the above described 50-mer ODN which was 3' end-modified with a CDPI$_3$ group and internally modified with a nitrogen mustard group (chlorambucil) sequence-specifically crosslinked to the expected site in a targeted gene (HlA DQβ1 0302 allele) present in living human BSM cells (a human B-lymphocyte cell line). The ODN-MGB conjugate was added to a suspension of BSM cells at 1-50 μM final concentration. After 3.5 hr the genomic DNA was extracted and treated with hot pyrrolidine to convert any alkylation events into nicks. Next the targeted region of the 0302 allele was amplified by LM-PCR (ligation mediated-polymerase chain reaction), a technique which can be used to detect cleavage events at single-base resolution. Analysis of the products on a sequencing gel showed that the modified ODN had bound to and alkylated the targeted site. A similar ODN lacking the CDPI$_3$ group was considerably less effective in efficiency of alkylation of the target.

It is probable that in the experiment above the recognition and binding of the ODN-MGB conjugate to homologous double-stranded DNA took place with the assistance of nuclear recombinases. In like experiments and applications endogenous recombinase enzymes can catalyze the sequence specific targeting of double-stranded genomic DNA by ODN-CDPI$_3$ conjugates in other living cells. When these ODNs have an appended crosslinking agent, they can alkylate the targeted DNA. By stabilizing the D-loop formed in the presence of recombinase, the CDPI$_3$ promotes the crosslinkage reaction. The crosslinkage event is a powerful inhibitor of expression of the targeted gene. Thus crosslinking ODN-CDPI3 conjugates can be used as antigene agents.

SPECIFIC EMBODIMENTS

Experimental Section

General Experimental

All air and water sensitive reactions were carried out under a slight positive pressure of argon. Anhydrous solvents were obtained from Aldrich (Milwaukee, Wis.). Flash chromatography was performed on 230-400 mesh silica gel. Melting points were determined on a Mel-Temp melting point, apparatus in open capillary and are uncorrected. Elemental analysis was performed by Quantitative Technologies Inc. (Boundbrook, N.J.). UV-visible absorption spectra were recorded in the 200-400-nm range on a UV-2100 (Shimadzu) or a Lambda 2 (Perkin Elmer) spectrophotometers. $^1$H NMR spectra were run at 20° C. on a Bruker WP-200 or on a Varian XL-200 spectrophotometer; chemical shifts are reported in ppm downfield from Me$_4$Si.

2,3,5,6-Tetrafluorophenyl 3-carbamoyl-1,2-dihydro-3H-pyrrolor[3.2-e]indole-7-carboxylate (1a). 2,3,5,6-Tetrafluorophenyl trifluoroacetate (2.6 g, 10 mmol, H. B. Gamper, M. W. Reed, T. Cox, J. S. Virosco, A. D. Adams, A. A. Gall, J. K. Scholler and R. B. Meyer, Jr. *Nucleic Acids Res.*, 1993, Vol. 21, No. 1, 145-150) was added dropwise to a solution of 3-carbamoyl-1,2-dihydro-3H-pyrrolo[3,2-e]indole-7-carboxylic acid (1.4 g, 6.1 mmol, D. L. Boger, R. S. Coleman, and B. J. Invergo. *J. Org, Chem.*, 1987, Vol. 52, 1521-1530) and triethylamine (1.4 ml, 10 mmol) in 15 ml of anhydrous DMF. After 1 hr, the reaction mixture was concentrated under vacuum (0.2 mm). The residue was triturated with 2 ml of dry dichloromethane. Ethyl ether (50 ml) was added and the mixture was left at 0° C. overnight. The precipitate was collected by filtration on sintered glass funnel, washed first with 50% ether/CH$_2$cl$_2$ (10 ml), then with ether (50 ml) and dried in vacuo. The product was obtained as a yellow solid (1.8 gi 75%): $^1$H NMR (Me$_2$SO-d$_6$, 200 MHz, ppm) 12.32 (s, 1H, NH), 8.13 (d, 1H, J=9 Hz, C4-H), 8.01 (m, 1H, C$_6$F$_4$H), 7.41 (s, 1H, C8-H), 7.26 (d, 1H, J=9 Hz, C5-H), 6.17 (s, 2H, CONH$_2$), 3.99 (t, 2H, J=9 Hz, NCH$_2$CH$_2$), 3.30 (t, 2H, J=9 Hz, NCH$_2$CH$_2$). Anal. Calcd. for C$_{18}$H$_{11}$N$_3$O$_3$F$_4$×2H$_2$0: C, 50.3; H, 3.52; N, 9.7. Found; C, 50.81; H, 3.60; N, 9.95.

2,3,5,6-Tetrafluorphenyl 3-(tert-butyloxycarbonyl)-1,2-dihydro-3H-pyrrolo[3,2-e]indole-7-carboxylate (1b). 2,3,5,6-Tetrafluorophenyl trifluoroacetate (2.6 g, 10 mmol) was added dropwise to a solution of 3-(tertbutyloxycarbonyl)-1,2-dihydro-3H-pyrrolo[3,2-e]indole-7-carboxylic acid (1.0 gi 3.7 mmol, D. L. Boger, R. S. Coleman, and B. J. Invergo. *J. Org. Chem.*, 1987, Vol. 52, 1521-1530) and triethylamine (1.5 ml, 10 mmol) in 10 ml of anhydrous CH$_2$cl$_2$. After 4 hrs, CH$_2$cl$_2$ was removed by evaporation at reduced pressure. Flash chromatography (4×2O cm, hexane-ethyl acetate, 1:2) afforded 1b as a yellow crystalline solid (1.25 gr 75%): $^1$H NMR (Me$_2$SO-d$_6$, 200 MHz, ppm) 12.39 (d, 1H, J=1.4 Hz, NH), 8.02 (m, 1H, C$_6$F$_4$H), 7.9 (br s, 1H, C$_4$H)i, 7.45 (d, 1Hj, J=1.4 Hz, C8-H), 7.33 (d, 1H, J=9 Hz, C5-H), 4.02 (t, 2H, J=9 Hz, NCH$_2$CH$_2$), 3.26 (t, 2H, J=9 Hz, NCH$_2$CH$_2$ 2)" 1.51 (s, 9H, C(CH$_3$)$_3$). Anal. Calcd. for C$_{22}$H$_{18}$N$_2$O$_4$F$_4$: C, 58.67; HI, 4.03; N, 6.22. Found: C, 58.45; HI, 4eO9; N, 6*13a 3-carbamoyl1,2-dihydro-3H-pyrrolor3,2-elindole-7 carboxylate dimer methyl ester (2a). A solution of methyl 1,2-dihydro-3H-pyrroloindole-7-carboxylate (0.6 g, 1.5 mmol), 1a (0.45 g, 2.25 mmol) and triethylamine (0.2 ml, 1.4 mmol) in 10 ml of anhydrous DMF was incubated at RT for 24 hrs and then at 0° C. for 12 hrs. The resulting insoluble solid was collected by filtration, washed with DMF (10 ml) and ether (20 ml). Drying in vacuo afforded 2a (0.61 g, 91%) as a pale yellow solid: ($_1$H NMR (Me$_2$SO-d$_6$, 200 MHz, ppm) 12.00 (d, 1H, J=1.8 Hz, NH'), 11.54 (s, 1H, NH), 8.28 (d, 1H, J=9 Hz, C4'-H), 7.97 (d, 1H, J=9 Hz, C4-H), 7.33 (d, 1H, J=9 z, C5'-H), 7.22 (d, 1H, J=9 z, C5-H), 7.13 (d, 1H, J=1.4 Hz, C8'-H), 6.94 (d, 1H, J=1.1 Hz, C8-H), 6.01 (s, 2H, CONH$_2$), 4.62 (t, 2H, J=8 Hz, (NH$_2$CH$_2$)'), 3.98 (t, 2H, J=8 Hz, NCH$_2$CH$_2$), 3.88 (s, 3H, CH$_3$), 3.41 (t, 2H, J=8 Hz, (NCH$_2$CH$_2$)1), 3.29 (t, 2H, NCH$_2$CH$_2$, partially obscured by water). Anal. Calcd. for C$_{24}$H$_{21}$N$_5$O$_5$×1H$_2$O×1DMF: C, 58.69; HI, 5.84; N, 15.21. Found: C, 58.93; H, 5.76; N, 15.82.

3-(tert-Butyloxycarbonyl)-1.2-dihydro-3H-pyrrolo[3,2-e]indole-7-carboxylate dimer methyl ester (2c). A solution of methyl 1,2-dihydro-3H-pyrroloindole-7carboxylate (0.5 g, 2.5 mmol), 1b (1.0 g, 2.2 mmol) and triethylamine (0.1 ml, 0.7 mmol) in 10 ml of anhydrous DMF was incubated at RT for 10 hrs and at 0° for 12 hrs. The resulting insoluble solid was collected by filtration, washed with DMF (5 ml) and ether (40 ml). Drying in vacuo afforded 2c (0.81 g, 74%) as an off white solid: $^1$H NMR (Me$_2$SO-d$_6$, 200 MHz, ppm) 12.01 (s, 1H, NH'), 11.64 (s, 1H, NH), 8.28 (d, 1H, J=9 Hz, C4'-H), 7.8 (br s, 1H, C4-H), 7.32 (apparent t, 2H, C5'-H+C5-H), 7.13 (d, 1H, J=1.1 Hz, C8'-H), 6.98 (d, 1H, J=1.1 Hz, C8-H), 4.62 (t, 2H, J=S Hz, (NH$_2$CH$_2$)'),' 4.02 (t, 2H, J=S Hz, NCH$_2$CH$_2$), 3.88 (s, 3H, CH$_3$), 3.41 (t, 0.2H, - Hz, (NCH$_2$CH$_2$)1), 3.25 (t, 2H, NCH$_2$CH$_2$), 1.52 (so 9H, C(CH$_3$)). Anal. Calcd. for C$_{29}$H$_{29}$N$_4$O$_5$: C, 67.19; H, 5.64; N, 11.19. Found: 66.72, H, 5.69; N, 11.31.

2,3,5,6-Tetrafluorophhenyl 3-carbamoyl-1,2-dihyo-Ryrrolor3o2-elindole-7-carboxylate dimer (2e). 2,3,5,6-Tetrafluorophenyl trifluoroacetate (2.6 g, 10 mmol) was added dropwise to a suspension of 2b (1.2 g, 2.8 mmol, D. L. Boger, R. S. Coleman, and B. J. Invergo. *J. Org. Chem.*, 1987, Vol. 52, 1521-1530) in 15 ml of anhydrous DMF. Triethylamine (1.4 ml, 10 mmol) was added and the mixture was stirred for 3 hrs. The mixture was concentrated in vacuo (0.2 mm) using rotary evaporator. The residue was triturated with 20 ml of dry dichloromethane. The product obtained was filtered, washed with dichloromethane (10 ml), ether (20 ml), and dried in vacuo to give 2e as a yellow solid (1.5 g, 93%): ($^1$H NMR (Ne$_2$SO-d$_6$, 200 MHz, ppm) 12.51 (do 1H, J=1.8 Hz, NH'), 11.58 (s, 1H. NH), 8.39 (d, 1H, J=8.9 Hz, C4'H), 8.04 (m, 1H, C$_6$F$_4$H)t 7.98 (do 1H, J=S.S Hz, C4-H), 7.58 (s, 1H, C8'), 7.42 (d, 1h, J=9 Hz, C5'-H), 7.22 (d, 1H, J=9 Hz, C5-H), 6.98 (s, 1H, CB—), 6.11 (s, 2H, CONH$_2$), 4.66 (t, 2H, J=7.8 Hz, (NCH$_2$CH$_2$)1), 3.94 (t, 2H, J=9.1 Hz, NCH$_2$CH$_2$), 3.47 (t, 2H, J=8 Hz, (NCH$_2$CH$_2$)'), 3.29 (t, 2H, J=9.1 Hz, NCH$_2$CH$_2$). Anal. Cacld. for C$_{29}$H$_{19}$N$_5$O$_4$F$_4$×1.5H2O: C, 57.62; H, 3.67; N, 11.59. Found: C, 57.18; H, 3.31; N, 11.54.

2,3,5,6-Tetrafluoroiphenyl 3-(tert-butyloxycarbonyllls2-dihydro-3H-Ryrrolor3o2-elindole-7-carboxylate dimer (2f). 2,3,5,6-Tetrafluorophenyl trifluoroacetate (0.75 g, 2.9 mmol) was added dropwise to a suspension of 2d (0.25 g, 0.5 mmol, D. L. Boger, R. S. Coleman, and B. J. Invergo. *J. Org. Chem.*, 1987, Vol. 52, 1521-1530) and triethylamine (0.5 ml, 3.5 mmol) in a mixture of anhydrous $CH_2Cl_2$ (8 ml) and DMF (2 ml). The mixture was stirred for 20 hrs. The resulting clear solution was concentrated in vacuo aid was added dropwise to 40 ml of 1M sodium acetate (pH 7.5). The precipitate was centrifuged, washed with water (2×40 ml), with 10% MeOH in ether (2×40 ml), with ether (40 ml), and with hexane (40 ml). Finally it was dried in vacuo to give 2f as a pale yellow solid (0.29 g, 91%): ($^1$H NMR ($Me_2SO$-$d_6$, 200 MHz, ppm) 12.51 (s, 1H, NH'), 11.66 (s, 1H, NH), 8.37 (d, 1H, J=8.8 Hz, C4'-H), 8.03 (m, 1H, $C_6F_4H$), 7.8 (br s, 1H, C4-H), 7.58 (s, 1H, C8'-H), 7.40 (d, 1H, J=9.1 Hz, C5'-H), 7.27 (d, 1H, J=8.6 Hz, C5-H), 7.1 (s, 1H, C8-H), 4.65 (t, 2H, J=8 Hz, ($NCH_2CH_2Y$), 4.02 (t, 2H, J=9 Hz, $NCH_2CH_2$), 3.46 (t, 2H, J=8 Hz, $NCH_2CH_2$)'), 3.25 (t, 2H, J=8.9 Hz, $NCH_2CH_2$), 1.51 (s, 9H, $C(CH_3)_3$). Anal. Calcd. for $C_{33}H_{26}N_4O_5F_4 \times 0.5H_2O$: C, 61.59; H, 4.23; N, 8.71. Found: C, 61.73; H, 4.12; N, 8.61.

3-carbamoyl-1,2-dihydro-3H-pyrrolo[3,2-e]indole-7-carboxylate trimer methyl ester (3a). A solution of methyl 1,2-dihydro-3H-pyrroloindole-7-carboxylate (1.0 g, 5 mmol), 2e (1.2 g, 2.1 mmol) and triethylamine (0.1 ml, mmol) in 15 ml of anhydrous DMF was incubated at RT for 24 hrs and at 0° C. for 12 hrs. The resulting insoluble solid was collected by filtration, washed with DMF (10 ml), $CH_2Cl_2$ (20 ml) and ether (20 ml). Drying in vacuo afforded 3a (1.1 g, 83%) as a pale yellow solid: ($^1$H NMR ($Me_2SO$-$d_6$, 200 MHz, ppm) 12.02 (s, 1H, NH"), 11.75 (s, 1H, NH'), 11.56 (s, 1H, NH), 8.28 (apparent t, 2H, J=8.3 Hz, C4-H"+C4'-H), 7.98 (d, 1H, J=9.4 Hz, C4-H), 7.98 (d, 1H, J=9 Hz, C4-H), 7.39-7.33 (2 d, 2H, C5"-H+C5'-H), 7.23 (d, 1H, J=8.7 Hz, C5-H), 7.14 (d, 1H, J=1.6 Hz, C8"-H), 7.10 (d, 1H, J=1 Hz, C8'-H), 6.97 (s, 1H, C8-H), 6.11 (s, 2H, $CONH_2$), 4.65 (t, 4H, ($NCH_2CH_2$)"+($NCH_2CH_2$)'), 3.98 (t, 2H, J=8.7 Hz, $NCH_2CH_2$), 3.88 (s, 3H, $CH_3$), 3.48-3.25 (m, 6H, ($NCH_2CH_2$)"+($NCH_2CH_2$)'+$NCH_2CH_2$ partially obscured with $H_2O$). Anal. Calcd. for $C_{35}H_{29}N_7O_5 \times 4.5H_2O$: C, 59.32; H, 5.0; N, 13.03. Found: C, 58.9; N, 5.06; N, 13.77.

2,3,5,6-Tetrafluorophenyl 3-carbamoyl-1,2-dihydro-3H-pyrrolo[3,2-e]indole-7-carboxylate trimer (3c). 2,3,5,6-Tetrafluorophenyltrifluoroacetate (2.*6 g; 10 mmol) was added dropwise to a suspension of 3b (1.1 g, 1.8 mmol) in 15 ml of anhydrous DMF and triethylamine (1.1 ml, 10 mmol). The mixture was stirred for 3 hrs. The mixture was concentrated in vacuo (0.2 mm). The residue was triturated with a mixture of dry dichloromethane (20 ml) and methanol (2 ml). The resulting product was collected by filtration, washed with dichloromethane (20 ml), ether (20 ml), and dried in vacuo to give 1.3 g (95%) of a yellow-green solid: ($^1$H NMR ($Me_2SO$-$d_6$, 200 MHz, ppm) 12.54 (d, 1H, J=1 Hz, NH"), 11.79 (s, 1H, NH'), 11.56 (s, 1H, NH), 8.41 (d, 1H, J=9.3 Hz, C4-H"), 8.27 (d, 1H, J=9.4 Hz, C4'-H), 8.03 (m, 1H, $C_6F_4H$), 7.98 (d, 1H, J=9 Hz, C4-H), 7.56 (s, 1H, C8"-H), 7.45-7.35 (m, 2H, C5"-H+C5'-H), 7.23 (d, 1H, J=9.2 Hz, C5-H), 7.13 (s, 1H, C8'-H), 6.97 (s, 1H, C8-H), 6.11 (s, 2H, $CONH_2$), 4.65 (m, 4H, ($NCH_2CH_2$)"+($NCH_2CH_2$)'), 3.98 (t, 2H, J=8.7 Hz, $NCH_2CH_2$), 3.45 (m, 4H, ($NCH_2CH_2$)"+($NCH_2CH_2$)'), 3.25 (t, 2H, J=8.7 Hz, $NCH_2CH_2$). Anal. Calcd. for $C_{40}H_{27}N_7O_5F_4 \times 2H_2O$: C, 61.59; H, 4.23; N, 8.71. Found: C, 61.73; H, 4.12; N, 8.61.

[3-carbamoyl-1,2-dihydro-3H-pyrrolo[3,2-e]indole-7-carbox]-1-amido-3-propanol trimer (3d). A solution of 3-amino-1-propanol (70 μl, 1.4 mmol), 3c (75 mg, 0.1 mmol) and triethylamine (0.1 ml, mmol) in 2.5 ml of anhydrous DMF was stirred at RT for 10 hrs. The resulting insoluble solid was collected by filtration, washed with DMF (2 ml), $CH_2Cl_2$ (10 ml) and ether (20 ml). Drying in vacuo afforded 3d (55 mg, 89%) as a pale yellow solid: ($^1$H NMR ($Me_2SO$-$d_6$, 200 MHz, ppm) 11.76 (s, 1H, NH"), 11.65 (s, 1H, NH'), 11.57 (s, 1H, NH), 8.47 (m, 1H, C4-H), 8.24 (m, 1H, C4-H), 7.99 (d, 1H, J=8.4 Hz, C4-H), 7.40-7.32 (2d, 2H, C8"-H+C5'-H), 7.23 (d, 1H, J=8.9 Hz, C5-H), 7.12 (s, 1H, C8"-H), 7.10 (s, 1H, C8'-H), 6.99 (s, 1H, C8H), 6.12 (s, 3H, $CONH_2$+NHCO), 4.66 (t, 4H, ($NCH_2CH_2$)"+($NCH_2CH_2$)'), 3.98 (t, 2H, J=8.7 Hz, $NCH_2CH_2$), 3.51-3.25 (m, 10H, $NCH_2CH_2$)"+$NCH_2CH_2$)'+$NCH_2CH_2$+$CH_2$ OH partially obscured with $H_2O$), 1.70 (p, 2H, J=6.6 Hz, $CH_2CH_2CH_2$).

2,3,5,6-Tetrafluorophenyl 3-[N-(9-fluorenylmethoxycarbonyl)]aminopropionate (4). 2,3,5,6-Tetrafluorophenyl trifluoroacetate (1.7 g, 6.5 mmol) was added dropwise to a solution of FMOC-alanine (2.0 g, 6.4 mmol) and triethylamine (1.0 ml, 7 mmol) in 20 ml of anhydrous $CH_2Cl_2$. After 1 hr., $CH_2Cl_2$ was removed by evaporation at reduced pressure using rotary evaporator, redissolved in 30 ml ethylacetate/hexane (1:1). Flash chromatography (4×20 cm, hexane/ethyl acetate, 3:1) afforded rude 4 as a white solid. It was recrystallized from hexane/ethyl acetate to give 4 as a white crystalline solid (2.3 g, 78%): $^1$H NMR ($CDCl_3$, 200 MHz, ppm) 7.73 (d, 2H, J=7.1 Hz, aromatic protons), 7.75 (d, 2H, J=7.7 Hz, aromatic protons), 7.24-7.42 (m, 4H, aromatic protons), 7.01 (m, 1H, $C_6F_4H$), 5.21 (br s, 1H, —CONH—), 4.38 (d, 2H, J=7.1 Hz, —$CH_2OCO$—), 4.20 (m, 1H, benzyl proton), 3.58 (m, -2H, NCH 2), 2.93 (t, 2H, J=5.4 Hz, —$CH_2CO$—). Anal. Calcd. for $C_{24}H_{17}NO_4F_4$: C, 62.75; H, 3.73; N, 3.05. Found: C, 62.52; H, 3.59; N, 3.01.

1-[3-[N-(9-Fluorenylmethoxycarbonyl)amino]-1-oxopropyl]amino-(R,S)-2,3-propanediol (5). A solution of 4 (2.0 g, 4.35 mmol) in 20 ml of anhydrous $CH_2Cl_2$ was added to a stirred solution of 3-amino-1,2-propanediol (0.6, mmol) in 10 ml MeOH. After 10 min, acetic acid (3 ml) was added and the mixture was evaporated to dryness. The residue was triturated with 100 ml of water. The obtained solid was filtered off, washed with water and dried by co-evaporation with toluene (2×50 ml) at reduced pressure. Washing with 50 ml of ethyl acetate followed by drying in vacuo overnight yielded 5 as a white crystalline solid (1.65 g, 99%): $^1$H NMR ($CDCl_3$+MeOD-$d4$, 200 MHz, ppm, $Me_4Si$) 7.77 (d, 2H, J=7.7 Hz, aromatic protons), 7.61 (d, 2H, J=7.3 Hz, aromatic protons), 7.45-7.29 (m, 4H, aromatic protons), 4.35 (d, 2H, J=7.1 Hz, —$CH_2OCO$—), 4.22 (m, 1H, benzyl proton), 3.72 (m, 1H, —CH— from $NHCH_2CHOHCH_2OH$), 3.52-3.27 (m, 6H, $OCONHCH_2$+$CH_2CHOHCH_2OH$), 2.44 (t, 2H, J=6.6 Hz, —$CH_2CO$—); Anal. Calcd. for $C_{21}H_{24}N_2O_5$: C, 5.61; H, 6.29; N, 7.29%. Found: C, 65.43; H, 6.28; N, 7.21.

1-[3-[N-(9-Fluorenylmethoxycarbonyl)amino]-1-oxopropyl]amino-(R,S)-2-[[bis(methoxyphenyl)phenylmethoxy]methyl]-2-ethanol (6). To a stirred solution of 5 (1.6 g, 4.2 mmol) in 30 ml of anhydrous pyridine was added DMTrCl (1.6 g, 4.7 mmol). After stirring for 3 hrs. under argon, the mixture was evaporated to dryness. Residual pyridine was removed by co-evaporation with toluene. The residue was dissolved in 100 ml of $CH_2Cl_2$, washed with 2×100 ml water, dried over sodium sulfate, and evaporated to dryness. The residue was purified by flash chromatography (4×20 cm, silica) using ethyl acetate as an eluent. The fractions containing pure product were combined and evaporated to dryness to yield 1.9 g (66%) of 6 as a colorless foam: $^1$H NMR ($CDCl_3$, 200 MHz, ppm, $Me_4Si$) 7.72 (d, 2H, J=7.2 Hz, aromatic protons), 7.56 (d, 2H, J=7 Hz, aromatic protons), 7.40-7.20 (m, 13H, aromatic protons), 6.80 (d, 4H, J=9 Hz, DMTr protons), 5.76 (br s, 1H, NH), 5.42 (br s, 1H, NH), 4.35 (d, 2H, J=6.6 Hz, —CH$_2$OCO—), 4.17 (m, 1H, benzyl proton), 3.83 (m, 1H, —CH— from NHCH$_2$C$\underline{H}$OHCH$_2$OH), 3.75 (s, 6H, OCH$_3$), 3.60-3.30 (m, 4H, OCONHC$\underline{H}_2$+C$\underline{H}_2$CHOHCH$_2$OH), 3.13 (d, 2H, J=5.4 Hz, CH$_2$ODMTr), 2.30 (t, 2H, J=5.4 Hz, —CH$_2$CO—); Anal. Calcd. for C$_{42}$H$_{42}$N$_2$O$_7$: C, 73.45; H, 6.16; N, 4.08. Found: C, 65.43; H, 6.28; N, 7.21.

2,3,5,6-Tetrafluorophenyl 1-[3-[N-(9-fluorenylmethoxycarbonyl)amino]-1-oxopropyl]amino(R,S)-2-[[bis(methoxyphenyl)phenylmethoxy]methyl]-2-ethyl butanedioate (7). To a solution of 6 (1.2 g, 1.75 mmol), triethylamine (0.2 g, 2 mmol), 1-methylimidazole (20 μl) in 10 ml of anhydrous CH$_2$Cl$_2$ was added 0.2 g (2 mmol) of succinic anhydride. This solution was stirred for 20 hrs. Triethylamine (60 μl) was added to the solution followed by 0.6 g (2.2 mmol) of 2,3,5, 6-tetrafluorophenyl trifluoroacetate. After 1 hr., CH$_2$Cl$_2$ was removed by evaporation at reduced pressure using a rotary evaporator, and the residue was dissolved in 15 ml ethylacetate/hexane (1:2). Flash chromatography (4×20 cm, hexane/ethyl acetate, 2:1) afforded 1b as a pale yellow foam (1.2 g, 73%): $^1$H NMR (CDCl$_3$, 300 MHz, ppm, Me$_4$Si) 7.71 (d, 2H, J=7.2 Hz, aromatic protons), 7.54 (d, 2H, J=7, aromatic protons), 7.40-7.20 (m, 13H, aromatic protons), 7.00 (m, 1H, C$_6$F$_4$H), 6.78 (d, 4H, J=7 Hz, DMTr protons), 5.71 (br s, 1H, NH), 5.42 (br s, 1H, NH), 5.15 (m, 1H, —CH— from NHCH$_2$C$\underline{H}$OHCH$_2$OH), 4.31 (d, 2H, J=6.2 Hz, —CH$_2$OCO—), 4.16 (d, 5.5 Hz, 1H, benzyl proton), 3.74 (s, 6H, OCH$_3$), 3.60-3.30 (m, 4H, OCONHC$\underline{H}_2$+C$\underline{H}_2$CHOHCH$_2$OH), 3.20 (br s, 2H, CH$_2$ODMTr), 2.98 (br s, 2H, COCH$_2$CH$_2$CO), 2.72 (br s, 2H, COCH$_2$CH$_2$CO), 2.20 (br s, 2H. —CH$_2$CO—); Anal, Calcd. for C$_{42}$H$_{42}$N$_2$O$_7$: C, 66.80; H, 4.96; N, 3.00. Found: C, 66.18; H, 4.98; N, 2.6.

Preparation of CPG derivative 8. A mixture of 5.0 g of long chain aminoalkyl controlled pore glass (LCAACPG), 0.5 ml of 1-methylimidazole, and 0.45 g (0.5 mmol) of 7 in 20 ml of anhydrous pyridine was swirled in 100 ml flask (orbital mixer, 150 rpm). After 3 hrs, the CPG was filtered on a sintered glass funnel and washed with 100 ml portions of DMF, acetone, and diethyl ether. The CPG was dried in vacuo and treated with a mixture of pyridine (20 ml), acetic anhydride (2 ml), and 1-methylimidazole (2 ml). After swirling for 30 min, the CPG was washed with pyridine, methanol, and diethyl ether, then dried in vacuo. The product (8) was analyzed for dimethoxytdtyl (DMTr) content according to the literature method (T. Atkinson and M. Smith. in M. Gait (ed.), *Oligonucleotide Synthesis, A Practical Approach*. IRL Press, 1984, Oxford, UK, pp. 35-81) and found to have a loading of 28 μmol/g.

Preparation of CPG derivative 9. The CPG derivative 8 (3.0 g) was treated twice with 20 ml of 20% piperidine in dry DMF for 5 min each time. The CPG was washed with 100 ml portions of DMF, methanol, and diethyl ether, then dried in vacuo.

Preparation of CPG derivative 10. A mixture of 2.5 g of 9, 7.5 ml of triethylamine, and 0.38 g (0.5 mmol) of -3c in -7.5 ml of anhydrous DMSO was swirled in 50 ml flask (orbital mixer, 150 funnel rpm). After 2 days, the CPG was filtered on a sintered glass funnel and washed with 100 ml portions of DMSO, acetone, and diethyl ether. The CPG was dried in vacuo and treated with a mixture of pyridine (10 ml), acetic anhydride (1 ml), and 1-methylimidazole (1 ml). After swirling for 30 min, the CPG was washed with DMSO, pyridine, methanol, and diethyl ether, then dried in vacuo.

2-[4-(Phenylazo)benzylthio]ethyl 5-[(tert-butyloxy)carboxamido]pentylcarboxylate (11). 6-[(Tert-butyloxy)carboxamido]hexanoic acid (4.16 g, 18 mmol) was dried by co-evaporation with dry DMF (70° C.). The residue was redissolved in dry DMF (25 ml) and 2-[4-(phenylazo)-benzylthio]-ethanol (4.08 g, 15 mmol), $\underline{N},\underline{N}$-dicyclohexyl carbodiimide (3.71 g, 18 mmol), 4-dimethylaminopyridine (1.83 g, 15 mmol) were added at 0° C. After stirring at 0° C. for 2 h and 20° C. for 12 h, the reaction mixture was evaporated to dryness by coevaporation with butyl acetate, and additional ethyl acetate (150 mL) was added. This solution was extracted with 0.7 M HCl (1×30 mL), 5% NaHCO$_3$ and H$_2$O (2×50 mL). The organic layer was dried over Na$_2$SO$_4$ and concentrated with rotary evaporator. Washing with 20 mL of ether and filtration afforded compound 11 (6.91 g, 89%). $^1$H NMR (CDCl$_3$, 200 MHz, ppm): 7.91 (m, 4H), 7.52 (m, 5H), 4.48 (t, 2H), 4.34 (s, 2H), 3.20 (t, 2H), 3.08 (m, 2H), 2.35 (t, 2H), 1.64-1.2 (m, 7H), 1.41 (s, 9H).

1,2,3-benzotriazol-1-yl 1-methyl-4-(tertbutyloxy)carboxamido-pyrrole-2-carboxylate. $\underline{N},\underline{N}'$-Dicyclohexylcarbodiimide (1.1 g, 5.3 mmol) was added to a solution of 1-methyl-4-[tert-butyloxy)carboxamido]pyrrole-2-carboxylic acid[4] (1.2 g, 5.2 mmol) and 1-hydroxybenzotriazol (0.63 g, 4.7 mmol). After stirring for 1 hr, the mixture was filtered through the sintered glass filter to separate precipitated $\underline{N},\underline{N}'$-dicyclohexylcarbodiimide. The filtrate was evaporated to dryness, redissolved in a mixture of CHCl$_3$ and pentane (1:1), and loaded onto a silica gel column. The fractions containing pure product were combined and evaporated to dryness to give 1.45 g (80%) of the desired product as a white solid: mp=138-138.5° C.; $^1$H NMR (CDCl$_3$, 200 MHz) 8.04 (d, 1H), 7.49-7.40 (m, 4H), 7.09 (d, 1H), 3.87 (s, 3H), 1.50 (s, 9H).

2-[4-(Phenylazo)benzylthio]ethyl 5-[1-methyl-4-(tertbutyloxy)carboxamido]pyrrole-2-carboxamido]pentylcarboxylate (12). Trifluoroacetic acid (5 mL) was added at 0° C. to 11 (0.73 g, 1.5 mmol). After stirring at 0° C. for 20 min the reaction mixture was evaporated to dryness by co-evaporation with CHCl$_3$. The residue was dissolved in dry CH$_2$Cl$_2$ (15 mL) and 1,2,3-benzotriazol-1-yl 1-methyl-4-(tert-butyloxy)carboxamido-pyrrole-2-carboxylate (0.59 g, 1.65 mmol), dry triethylamine (0.23 g, 2.3 mmol) were added. After stirring at ambient temperature for 15 min, CHCl$_3$ was added (100 mL). The reaction mixture was extracted with 5% NaHCO$_3$ (2×20 mL), H$_2$O (2×20 mL). The organic layer was dried over Na$_2$SO$_4$ and concentrated on a rotary evaporator. Chromatography on silica gel (100 g) with CHCl$_3$ afforded 0.88 g (91.8%) 12. $^1$H NMR (CDCl$_3$, 200 MHz, ppm): 7.88 (m, 4H), 7.46 (m, 5H), 6.74 (s, 1H), 6.38 (s, 1H), 6.26 (s, 1H), 5.87 (t, 1H), 4.18 (t, 2H, J=6 Hz), 3.82 (s, 3H), 3.79 (s, 2H), 3.3 (m, 2H), 2.63 (t, 2H, J=6 Hz), 2.30 (t, 2H, J=6 Hz), 1.64-1.2 m, 6H), 1.46 (s, 9H).

2-[4-(Phenylazo)benzylthio]ethyl 5-[1-methyl-4-[1 methyl-4-(tert-butyloxy)carboxamidopyrrole-2-carboxamido]pyrrole-2-carboxamido]pentylcarboxylate. (13). A solution of 12 (2.43 g, 4 mmol) in dry CH$_2$Cl$_2$ (8 mL) was treated with trifluoroacetic acid (4 mL) at 0° C. The resulting solution was left at ambient temperature in stopped flask for 1 hr and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$0 (1×20 mL), were dried over Na$_2$SO$_4$ and evaporated. The residue was dissolved in CH$_2$Cl$_2$ (10 mL) and 1,2,3-benzotriazol-1-yl 1-methyl-4-(tert-butyloxy)carboxamidopyrrole-2-carboxylate (1.43 g, 4 mmol) and dry triethylamine (0.8 g, 8 mmol) were added. After stirring at ambient temperature for 30 min, CHCl$_3$ (100 mL) was added. The reaction mixture was extracted with 5% NaHCO$_3$ (2×20 mL), H$_2$0 (2×20 mL). The organic layer and concentrated on a rotary was dried over Na$_2$SO$_4$ and concentrated on a rotary evaporator. Chromatography on silica gel (100 g) with CHCl$_3$ afforded 1.95 g (66.8%) of 13. $^1$H NMR (CDCl$_3$, 200 MHz, ppm): 7.87 (m, 4H), 7.46 (m, 5H), 7.04 (d, 1H, J=1.5 Hz), 6.77 (br s, 1H), 6.52 (br s, 1H), 6.50 (d, 1H, J=1.5 Hz), 6.31 (br s, 1H), 5.95 (t, 1H), 4.19 (t, 2H, J=6 Hz), 3.85 (s, 6H), 3.78 (s, 2H), 3.32 (m, 2H), 2.64 (t, 2H, J=6 Hz), 2.31 (t, 2H, J=6 Hz), 1.64-1.2 (m, 6H) 1.48 (s, 9H).

2-[4-(Phenylazo)benzylthio]ethyl 5-[1-methyl-4-[1-methyl-4-[1-methyl-4-(tert-butyloxy)carboxamidopyrrole-2-carboxamido]pyrrole-2-carboxamido]pyrrole-2-carboxamido]pentylcarboxylate (14). A solution of 13 (1.90 g, 2.6 mmol) in dry CH$_2$Cl$_2$ (6 mL) was treated with trifluoroacetic acid (3 mL) at 0° C. The resulting solution was left at ambient temperature in stopped flask for 1 hr and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$O (1×20 mL), were dried oveNa$_2$SO$_4$ and evaporated. The residue was dissolved in CH$_2$Cl$_2$ (2.5 mL) and 1,2,3-benzotriazol-1-yl 1-methyl-4-(tert-butyloxy)carboxamidopyrrole-2-carboxylate (1.4 g, 3.9 mmol), dry triethylamine (0.8 g, 8 mmol) were added. After stirring at ambient temperature for 1 h, CHCl$_3$ (100 mL) was added. The reaction mixture was extracted with 5% NaHCO$_3$ (2×20 mL), H$_2$O (2×20 mL). The organic layer was dried over Na$_2$SO$_4$ and concentrated on a rotary evaporator. Chromatography on silica gel (100 g) with 0-1.5% methanol in CHCl$_3$ afforded 1.56 g (70.5%) of 14. $^1$H NMR (CDCl$_3$, 200 MHz, ppm): 7.87 (m, 4H), 7.68 (br s, 1H), 7.60 (br s, 1H), 7.46 (m, 5H), 7.08 (br s, 2H), 6.78 (br s, 1H), 6.56 (d, 1H, J=1.5 Hz), 6.60 (br s, 1H), 6.55 (d, 1H, J=1.5 Hz), 6.03 (t, 1H), 4.18 (t, 2H, J=6 Hz), 3.86 (m, 9H), 3.78 (s, 2H), 3.32 (m, 2H), 2.63 (t, 2H, J=6 Hz), 2.30 (t, 2H, J=6 Hz), 1.64-1.2 (m, 6H), 1.48 (s, 9H).

2-[4-(Phenylazo)benzylthio]ethyl-5-[1-methyl-4-[(1-methyl-4-[1-methyl-4-[1-methyl-4-(tert-butyloxy)carboxamidopyrrole-2-carboxamido]pyrrole-2-carboxamido]pyrrole-2-carboxamido]pyrrole-2-carboxamido]pentylcarboxylate (15). A solution of 14 (0.32 g, 0.32 mmol) in dry CH$_2$Cl$_2$ (5 mL) was treated with trifluoroacetic acid (2.5 mL) at 0° C. The resulting solution was left at ambient temperature in stopped flask for 1 h and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$O (1×20 mL), were dried over Na$_2$SO$_4$ and evaporated. The residue was dissolved in CH$_2$Cl$_2$ (1 mL) and 1,2,3-benzotriazol-1-yl 1-methyl-4-(tert-butyloxy)carboxamidopyrrole-2-carboxylate (0.11 g, 0.32 mmol), dry triethylamine (0.06 g, 0.03 mmol) were added. After stirring at ambient temperature for 1.5 h. CHCl$_3$ (100 mL) was added. The suspension was filtered and the filtrate was extracted with 5% NaHCO$_3$ (2×20 mL), H$_2$O (2×20 mL). The organic layer was dried over Na$_2$SO$_4$ and evaporated to dryness. The yield of 15 was 0.25 g (80%). $^1$H NMR (CDCl$_3$, 200 MHz, ppm): 8.17 (br s, 1H), 7.98 (br s), 7.96 (br s), 1H 7.85 (m, 4H), 7.44 (m, 5H), 7.09 (br s, 2H), 7.02 (s, 1H), 6.78 (br s, 1H), 6.74 (br, 1H), 6.66 (s, 1H), 6.58 (s, 3H), 6.29 (t, 1H), 4.18 (t, 2H, J=6 Hz), 3.78 (m, 14H), 3.28 (m, 2H), 2.60 (t, 2H, J=6 Hz), 2.26 (t, 2H, J=6 Hz), 1.64-1.2 (m, 6H), 1.48 (s, 9H).

2-[4-(Phenylazo)benzylthio]ethyl 5-[1-methyl-4-[1-methyl-4-[1-methyl-4-[1-methyl-4-(tertbutyloxy)carboxamidopyrrole-2-carboxamido]pyrrole-2-carboxamido]pyrrole-2-carboxamido]pyrrole-2-carboxamido]pyrrole-2-carboxamido]pentylcarboxylate (16). A solution of 15 (0.65 g, 0.67 mmol) in dry CH$_2$Cl$_2$ (10 mL) was treated with trifluoroacetic acid (5 mL) at 0° C. The resulting yellowish solution was left at ambient temperature in stopped flask for 1 h and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$O (1×20 mL), were dried over Na$_2$SO$_4$ and evaporated. The residue was dissolved in DMF (1 mL) and 1,2,3-benzotriazol-1-yl 1-methyl-4-(tertbutyloxy)carboxamidopyrrole-2-carboxylate (0.24 g, 0.67 mmol), dry triethylamine (0.13 g, 0.67 mmol) were added. After stirring at ambient temperature for 3 h, the reaction mixture was evaporated to dryness by coevaporation with butyl acetate. The residue was dissolved in 3 mL 2.5% DMF in CHCl$_3$. Chromatography on silica gel (100 g) with 0-2.5% methanol in CHCl$_3$ (2.5% DMF) afforded 0.67 g (45%) of 16.

2,3,5,6-Tetrafluorophenyl-4'-[bis(2-chloroethyl)amino] phenylbutyrate (Chlorambucil 2,3,5,6-tetrafluorophenyl ester)

To a solution of 0.25 g (0.82 mmol) of chlorambucil (supplied by Fluka A. G.), 0.3 g (1.1 mmol) of 2,3,5,6-tetrafluorophenyl trifluoroacetate in 5 ml of dry-dichloromethane was added 0.2 Ml of dry triethylamine. The mixture was stirred Under argon at room temperature for 0.5 h and evaporated. The residual oil was purified by column chromatography on silica gel with hexane-chloroform (2:1) as the eluting solvent to give the ester as an oil: 0.28 g (75%); TLC on silica gel (CHCl$_3$) R$_f$ 0.6; IR (in CHCl$_3$) 3010; 1780, 1613, 1521, 1485 cm$^{-1}$.

Introduction of Chlorambucil Residue into the Primary Amino Groups of Oligonucleotides.

Preparation of the cetyltrimethylammonium salt of oligonucleotides: a 100 μL of aqueous solution of oligonucleotide (50-500 ug), generally triethylammonium salt, was injected to a column packed with Dowex 50wx8 in- the, cetyltrimethylammonium form and prewashed with 50% alcohol in water. The column was eluted by 50% aqueous ethanol (0.1 mL/min). Oligonucleotide containing fraction was dried on a Speedvac over 2 hours and used in following reactions.

Ethanol solution (50 uL) of cetyltrimethylammonium salt of an oligonucleotide (50-100 μg) was mixed with of 0.08 M solution of 2,3,5,6-tetrafluorophenyl-4'-[bis(2-chloroethyl) amino]phenylbutyrate (tetrafluorophenyl ester of chlorambucil) in acetonitrile (50 μL) and 3 μL of diisopropylethylamine. After shaking for three hours at room temperature, the product was precipitated by 2% LiClO$_4$ in acetone (1.5 mL). The product was reprecipitated from water (60 uL) by 2% LiClO$_4$ in acetone three times. Finally, chlorambucil derivative of oligonucleotide was purified by Reverse Phase Chromatography with approximately 50-80% yield. The fraction containing a product was concentrated by approximately butanol. Isolated chlorambucil derivative of oligonucleotide was precipitated in acetone solution of LiClO$_4$, washed by acetone and dried under vacuum of oil pump. All manipulation of reactive oligonucleotide was performed as quickly as possible, with the product in ice-cold solution, starting from the chromatographic fraction collected.

Oligonucleotide Synthesis

All oligonucleotides were prepared from 1 μmol of the appropriate CPG support on an ABM 394 using protocol supplied by manufacturer. Standard reagents for the β-cyanoethylphosphoramidite coupling chemistry were purchased from Glen Research. 5'-aminohexyl modifications were introduced using an N-MMT-hexanolamine phosphoramidite linker (Glen Research). 3'-aminohexyl modifications were introduced using the CPG prepared as previously described, C. R. Petrie, M. W. Reed, A. D. Adans, and R. B. Meyer, Jr. *Bioconjugate Chemistry,* 1992, 3, 85-87.

Preparation of Conjugates (Reaction Scheme 3).

To a solution of cetyltrimethylammonium salt of an aminohexyl modified oligonucleotide (30-50 nmol, Jost, J.-P., Jiricny, J., and Saluz, H, (1989) Quantitative precipitation of short oligonucleotides with low concentrations of cetyltrimethylammonium bromide. *Nucleic Acids Res.* 17, 2143) and 1.5 µl of N,N-diisopropylethylamine in 40 µl of dry DMSO was added 40 µl of 4 mM solution of the TFP ester (1a, 1b, 2e, 2f or 3c). The reaction mixture was kept for 12 hrs at RT. The oligonucleotide related material was precipitated by addition of 1.5 ml of 2% $LiCl_4$ in acetone. The pellet was washed with acetone, and dried in vacuo. The pellet was redissolved in 60 µl of 50% DMF in $H_2O$ and precipitated again as described above using 2% solution of $LiClO_4$ in acetone. This procedure was repeated twice. The residue was purified by HPLC (4.6×250 mm, C-18, Dynamax-300A, Rainin) using a gradient of acetonitrile from 20 to 75% in the presence of 50 mM $LiClO_4$. The fraction containing pure product was dried in vacuo using speedvac. The residue was dissolved in 60-80 µl of $H_2O$ and precipitated with 1.5 ml of 2% $LiClO_4$ in acetone. After washing with acetone (2×1.5 ml) and drying in vacuo, the pellet was dissolved in 100 µl of $H_2O$. The yield of final product was 20-50%.

A modified procedure of Godovikova et al. (T. S. Godovikova, V. F. Zarytova, T. V. Maltzeva, L. M. Khalimskaya. *Bioorgan. Khim.,* 1989, 15, 1246-1259) was used for the preparation of the oligonucleotide conjugates bearing 4-amino-N-methylpyrrol-2-carboxylic acid residues. A solution of cetyltrimethylammonium salt of 3'-phosphate-containing oligonucleotide (50-100 nmol), triphenylphospine (10 mg), 2,2'-dipyridyldisulfide (10 mg), N,N-dimethylaminopyridine (10 mg), and one of the analogues selected from compounds 11 through 16 in 100 µl of dry DMF was incubated for 20 min at RT. The oligonucleotide related material was precipitated by addition of 1.5 ml of 2% $LiclO_4$ in acetone. The pellet was washed with acetone, and dried in vacuo. The residue was purified by HPLC using gradient of acetonitrile from 20 to 75% in presence of 50 mM $LiClO_4$. The fraction containing pure product was dried in vacuo using speedvac. The residue was dissolved in 60-80 µl of $H_2O$ and precipitated with 1.5 ml of 2% $LiClO_4$ in acetone. After washing with acetone (2×1.5 ml) and drying in vacuo, the pellet was dissolved in 100 µl of $H_2O$. The yield of final product was 30-50%.

Preparation of Conjugates (Reaction Scheme 4).

CPG containing 5'-aminohexyl derivatized oligonucleotide obtained in a synthesis on 1 µmol scale was treated with 2% dichloroacetic acid in $CH_2Cl_2$ to remove the 9-fluorenylmethoxycarbonyl (Fmoc) protecting group from the amino group followed by washing with acetonitrile, and drying by flushing with argon. The CPG was transferred into 1.5 ml plastic tube and 100 ul of 50 mM solution of TFP ester in anhydrous DMSO was added. The tube was shaken for 24 hrs, then washed with 3×1.5 ml DMSO, 2×1.5 ml acetone, and dried in vacuo. The CPG was treated with concentrated ammonia to deprotect oligonucleotide using standard conditions. The resulting reaction mixture was separated using reverse phase HPLC as described above. Typical yield was about 50%.

Thermal Denaturation Studies.

Optical melting curves of oligonucleotide complexes bearing 4-amino-N-methylpyrrol-2-carboxylic acid residues were obtained in 200 mM NaCl, 10 mM $Na_2HPO_4$, 0.1 mM EDTA (pH 7.0) on the UV detector of a Milichrom liquid chromatograph in a thermoregulated cell specially designed for this purpose. The data were collected and processed on a personal computer as described by S. G. Lokhov et al. (S. G. Lokhov, M. A. Podyminogin, D. S. Sergeev, V. M. Silnikov, I. V. Kutyavin, G. V. Shishkin, V. F. Zarytova. *Bioconjugate Chem.* 1992, 3, 414).

The oligonucleotide complexes carrying 1,2-dihydro-3 H-pyrrolo[3,2-e]indole-7-carboxylic acid (CDPI) residues were melted in 140 mM KCl, 10 mM $MgCl_2$, 20 mM HEPES-HCL (pH 7.2) on a Lambda 2 (Perkin Elmer) spectrophotometer with a PTP-6 automatic multicell temperature programmer. The melting temperatures of complexes (Tm) were determined from the derivative maxima.

Primer Extension Reactions

Primer extension reactions were performed as previously described by Lee, et al, (1994) *Biochemistry* 33: 6024-6030. The final concentrations of template, primer and blocking ODMs were $5 \times 10^{-10}$ M, $4 \times 10^{-8}$ M and $10^{-9}$ M, respectively. Primer extension was carried out for 15 min at 45° C. and the products were analyzed by denaturing gel electrophoresis as described in the reference.

In the absence of any blocking ODN, the primer extension reaction generated a high molecular weight product which ran as an unresolved band in the sequencing gel. Weak bands corresponding to pause sites or to spontaneous termination events were reproducibly observed in all reaction mixtures. Unmodified 16-mer and 32-mer ODNS, fully complementary to the target, failed to block primer extension. Also without activity were complementary 8-mer and 16-mer ODNS, each of which was 3'-linked to a $CDPI_3$ group. Only a fully complementary 16-mer ODN with a 5'-conjugated $CDPI_3$ group arrested primer extension by T7 DNA polymerase. A complementary 8-mer ODN with the same 5' modification generated only a trace amount of blocked product. Control ODNs confirmed that inhibition of primer extension required both a complementary ODN and a covalently linked MGB. Two singly-mismatched 16-mer ODNS, each with a 5'-linked $CDPI_3$ peptide, were much less inhibitory than the perfectly matched ODN-MGB conjugates. Addition of unmodified 16-mer ODN together with an equimolar amount of free $CDPI_3$ had no effect on primer extension, emphasizing the importance of the conjugation of the NGB to the ODN. When a 5' acridine moiety was conjugated to the fully complementary 16-mer ODN instead of the MGB, a loss of inhibitory activity was seen.

Cell Culture Crosslinking Experiment

The ODN-MGB conjugate was complementary to nucleotides 815-864 of the template strand of the DQβ1 allele. *Proc. Natl. Acad. Sci. USA* (1983) 80: 7313-7317. The human BSM B-cells used here are homozygous for this allele and express it constitutively. Prior to adding the ODN, the BSM cells were grown in a 25 ml flask to a density of $4.5 \times 10^6$ cells per ml of media.

For each treatment the cells from a 2 ml aliquot of culture were pelleted and resuspended in 200 ul of serum free media which contained 0, 1, 10 or 50 µM 50-mer chlorambucil-linked ODN (either with or without a 3' conjugated $CDPI_3$ group). Each sample was incubated for 3.5 hours at 37° C. with 5% $CO_2$ in a 48-well microtiter plate. The cells were then transferred to Eppendorf 0.5 ml centrifuge tubes, pelleted 5 min at 2,000 rpm, washed twice with 500 µl phosphate buffered saline (PBS) and deproteinized with Proteinase K/SDS overnight at 370° C. After phenol/chloroform extraction and Rnase A digestion the DNA was treated with 1M pyrrolidine at 90° C. for 30 min. Pyrrolidine was removed by ethanol precipitation, and the ligation-mediated polymerase chain reaction (PCR) reaction was performed as described by Lee et al., supra. Amplified DNA was analyzed on a sequencing gel to visualize any sequence specific nicking that might have resulted from alkylation of the target by the chlorambucil-containing ODNS. Results showed cleavage at the nucleotide on the target adjacent to the crosslinker on the ODN, and that the CDPI$_3$-containing 50-mer was 10-fold more efficient than the same ODN without the MGB in sequence specifically alkylating the 0302 allele.

Complete media was prepared from the following components (the serum free media lacked HI-FCS): 500 ml RPMI 1640 with L-Glutamine (2 mM) (Gibco BRL Cat. No. 11875-036)

50 ml of HI-FCS (Gibco BRL Cat. No. 26140, heat inactivated 30 min at 55° C.) 5 ml of 100× Penn/Strep (Gibco BRL Cat. No. 15070-022) 5 ml of 200 mM L-Glutamine (Gibco BRL Cat. No. 25030-024)

5 ml of 100× Sodium Pyruvate (11 mg/ml; made from Gibco BRL Cat. No. 11840-030)

5 ml of 1 M HEPES, pH 7.3 (Gibco BRL Cat. No. 15630023)

Improved Hybridization and Discriminatory Properties of MGB-Oligonucleotide Conjugates In many types of hybridization assay, base-pairing interactions between a probe oligonucleotide and a fully- or partially-complementary target sequence are detected, either directly (by measuring hybridized probe) or indirectly (by measuring some event that depends on probe hybridization). Modifications which improve hybridization kinetics (i.e., speed up the hybridization process), change the equilibrium of the hybridization reaction to favor product (i.e., increase the fraction of probe in hybrid), and/or lead to the formation of more stable hybrids, will allow more rapid, efficient and accurate hybridization assays, thereby increasing efficiency of hybridization and facilitating the use of hybridization techniques in new areas such as diagnostics and forensics. Furthermore, it is often advantageous to be able to distinguish between a perfect hybrid (or perfect match), in which every probe nucleotide is base-paired to a complementary nucleotide in the target, and an imperfect hybrid or mismatch, in which one or more probe nucleotides are not complementary to the target. For example, a hybrid between an oligonucleotide and a target nucleic sequence wherein one base in the oligonucleotide is non-complementary to the target sequence is termed a single-nucleotide mismatch. Single-nucleotide mismatch discrimination (i.e., the ability to distinguish between a perfect match and a single-nucleotide mismatch) is extremely useful in the detection of mutations for diagnostic purposes, and in the determination of allelic single-nucleotide polymorphisms in diagnostic, therapeutic, and forensic applications. Heretofore, such single-nucleotide mismatch discrimination has been difficult to achieve, especially under conditions of high stringency.

The present invention provides, among other things, modified oligonucleotides for use as probes and primers. The oligonucleotides are modified by the covalent attachment of a minor groove binding moiety (MGB). The structure and preparation of exemplary MGBs are provided herein. A MGB-oligonucleotide conjugate having a defined sequence that is complementary to a target sequence in a second polynucleotide will form a duplex having greater hybrid strength, compared to oligonucleotide probes and primers of the prior art. A MGB-oligonucleotide conjugate whose sequence will result in a hybrid having a single-nucleotide mismatch with that of a target sequence in a second polynucleotide will form a duplex that is more easily discriminated from a perfectly-matched duplex, compared to oligonucleotide probes and primers of the prior art.

Increased Hybrid Stability

The strength of hybridization, or hybrid stability, between two nucleic acids, can be determined by subjecting a nucleic acid duplex to steadily increasing temperature or to a steadily increasing concentration of a denaturing agent. Ultraviolet absorbance (a measure of base-pairing) is determined as a function of temperature or concentration of denaturing agent. Absorbance increases as base pairs become unpaired and base stacking interactions are lost, and absorbance reaches a plateau when the duplex has been completely denatured. Several measures of hybridization strength can be obtained from this type of analysis. The melting temperature ($T_m$) is commonly defined as the temperature (or concentration) at which half of the base-pairs in the duplex become unpaired. The temperature at which the change in absorbance with respect to temperature (or with respect to the concentration or intensity of denaturing agent) is at a maximum (i.e., the temperature at which dA/dT is at a maximum) is known as the $T_{max}$ for that particular nucleic acid duplex.

Increased hybridization strength between MGB-oligonucleotide conjugates and their target sequences has several advantageous consequences. For example, short oligonucleotides, less than about 21 nucleotides in length, are generally not suitable for use in amplification techniques such as PCR, because such techniques are conducted at elevated temperatures (usually over 70° C.) that are above the $T_m$ of short oligonucleotides. However, conjugation of a MGB to such a short oligonucleotide results in an increase in hybrid stability sufficient for the MGB-oligonucleotide conjugate to achieve specific, stable hybridization at elevated temperatures, such as are used in PCR and other amplification techniques.

Another advantage of the increased hybrid stability conferred on oligonucleotides by MGB conjugation is that it is now possible to obtain hybridization to a target using an oligonucleotide containing one or more complementary sequence mismatches with the target sequence. This will make it possible to use a single defined sequence oligonucleotide as a primer or probe for a target that exhibits genetic heterogeneity. To provide just one example, MGB-oligonucleotide conjugates are useful in assays which utilize oligonucleotides for the detection of HIV. Since the HIV genome undergoes frequent mutational events, some of which lead to resistance to anti-viral therapeutics, it is possible that a mutation present in a region of the viral genome complementary to an oligonucleotide probe or primer will result in the mutant becoming undetectable in an oligonucleotide-based assay. However, MGB-oligonucleotide conjugates, by virtue of their increased hybrid stability, allow an oligonucleotide with one or more nucleotide mismatches to recognize a specific target sequence, thereby functioning as an effective probe and/or primer in systems characterized by a tendency toward frequent mutation of the target sequence. In addition, multiple subtypes of a virus, distinguished by changes in one or a few nucleotides in the target region, can be detected with a MGB-oligonucleotide conjugate having a single sequence.

Although a MGB-conjugated oligonucleotide is stabilized in its duplex relative to a non-conjugated oligonucleotide, the conjugated oligo maintains its sequence specificity, under appropriate conditions of stringency, such that mismatches can be discriminated (i.e., the stability of a duplex formed by a perfectly-matched oligonucleotide is higher than that of a mismatched duplex when the oligonucleotide is conjugated to a MGB, even though the $T_m$ of both duplexes is increased by MGB conjugation). That is to say, if a perfectly-matched oligonucleotide and an oligonucleotide differing by one nucleotide were compared (in terms of the strength of hybrids formed with a specific target sequence), the $T_m$ of hybrids formed by both oligonucleotides would increase, but the $T_m$ of the hybrid formed by the perfectly-matched oligonucleotide would increase by a greater extent. This effect is particularly pronounced with shorter oligonucleotides, preferably those shorter than 21 nucleotides in length and, most preferably, those shorter than 11 nucleotides in length. The result is that, even though mismatched probes form more stable hybrids when conjugated to a MGB, it is possible to distinguish a perfect match from a single-nucleotide mismatch using a MGB-oligonucleotide conjugate. In fact, the difference in $T_m$ between a perfect match and a single-nucleotide mismatch is heightened when MGB-oligonucleotide conjugates are used as probes and/or primers (see infra).

As described herein, the present inventors have discovered that covalent attachment of a MGB to an oligonucleotide dramatically increases the stability of hybrids formed by that oligonucleotide, as measured, for example, by an increase in $T_m$ of the hybrid. Increased hybrid stability for short oligonucleotides, as provided by the invention, provides short oligonucleotides useful as primers in various procedures involving primer extension, such as PCR, provided the appended MGB does not block the 3'-end of the oligonucleotide in a way that inhibits extension. It is shown herein (see, Example 1, infra) that MGB-oligonucleotide conjugates are indeed capable of being extended from their 3'-end by a polymerase. Thus, very short oligonucleotides (less than about 21-mers), which of themselves would form fairly unstable hybrids, are able, when conjugated to a MGB, to form hybrids with their target sequence that are stable enough to serve as primers in amplification reactions such as PCR.

There are several advantages to the use of short oligonucleotides as primers in amplification processes such as PCR. These advantages have not previously been available in procedures which are normally conducted at high temperatures using thermophilic enzymes. For example, shorter oligonucleotides are easier and less expensive to produce. Additionally, more rapid hybridization kinetics may be obtained with short oligonucleotides. Furthermore, homology searches conducted using PCR or related priming and/or amplification techniques can be based on very short regions of homology, on the order of 2-3 codons. Within this size range, single-nucleotide mismatch discrimination is maintained by MGB-oligonucleotide conjugates (see infra), making possible very sensitive searches over very limited regions of homology.

Enhanced Mismatch Discrimination

It is becoming increasingly important to be able to distinguish two sequences which differ from each other by a single nucleotide. Single-nucleotide polymorphisms form the molecular basis of many diseases, can determine an individual's response to a particular therapeutic, and are useful from a forensic viewpoint. The ability to discriminate between two polynucleotides which differ by a single nucleotide is an important and valuable property of MGB-oligonucleotide conjugates. Conjugates between a MGB and a short (<21-mer) oligonucleotide retain the sequence specificity and discriminatory properties of short oligonucleotides while, at the same time, being capable of forming hybrids having stability characteristics of longer oligonucleotides. Without wishing to be bound by any particular theory, a possible explanation for the combination of these desirable properties in a MGB-oligonucleotide conjugate is as follows. Since each base-pair contributes to the stability of a hybrid; the shorter the hybrid, the greater the relative contribution of each individual base pair to the stability of a probe-target hybrid. Hence, the shorter the probe, the greater the difference in stability between a probe forming a perfect match with its target and a probe having a single base mismatch. Thus, all other things being equal, the shorter the oligonucleotide, the greater its ability to discriminate between a perfect match and a single nucleotide mismatch. However, a short oligonucleotide (even one that forms a perfect match with its target) is not able to form a stable hybrid at the elevated temperatures normally used in amplification techniques such as PCR. Thus, the potential discriminatory power of short oligonucleotides cannot be exploited in PCR and related amplification methods.

One of the effects of conjugating a MGB to a short oligonucleotide is to increase the stability (and hence the $T_m$) of a hybrid involving the short oligonucleotide to a degree that is compatible with use of the oligonucleotide at the elevated temperatures necessary for amplification reactions involving thermostable polymerizing enzymes. At the same time, the discriminatory properties (i.e. the heightened difference in $T_m$ between a perfect hybrid and a single base mismatch) characteristic of short oligonucleotides are retained by the MGB-oligonucleotide conjugate under these conditions. See Examples 2, 3 and 6, infra.

Additional Advantages

Since kinetics of hybridization are inversely proportional to the length of an oligonucleotide, another useful property of the MGB-oligonucleotide conjugates is that they are capable of annealing to their target more rapidly than are longer oligonucleotides. An additional factor leading to more rapid hybridization kinetics of MGB-oligonucleotide conjugates is that the MGB is likely to serve as a nucleation site for hybridization. Furthermore, the additional free energy of binding imparted by the MGB most likely lowers the off-rate of binding between the oligonucleotide and its target. As a result, hybridization assays employing MGB-oligonucleotide conjugates can be conducted more rapidly than assays employing longer unconjugated oligonucleotides that form hybrids of comparable stability. Hence, an additional advantage provided by the novel compositions of the invention is that it is now feasible to perform hybridization analyses in situations in which time is limited. To provide but one example, one could use the methods and compositions of the invention in a surgical procedure, to investigate the molecular properties of excised tissue. Combining several advantageous properties of MGB-oligonucleotide conjugates, one would be able to test for molecular properties characteristic of the transformed state (for example, single-base mutations in oncogenes or tumor suppressor genes) in cells from a portion of resected tissue, during surgery, to guide the extent of resection. A description of the use of the methods and compositions of the invention in various techniques of mutation detection is provided herein.

Exemplary Applications

The methods and compositions of the present invention can be used with a variety of techniques, both currently in use and to be developed, in which hybridization of an oligonucleotide to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; techniques in which hybridization of an oligonucleotide to a target nucleic acid is followed by hydrolysis of the oligonucleotide to release an attached label; and techniques in which two or more oligonucleotides are hybridized to a target nucleic acid and interactions between the multiple oligonucleotides are measured. Conditions for hybridization of oligonucleotides, and factors which influence the degree and specificity of hybridization, such as temperature, ionic strength and solvent composition, are well-known to those of skill in the art. See, for example, Sambrook et al., supra; Ausubel, et al., supra; M. A. Innis et al (eds.) PCR Protocols, Academic Press, San Diego, 1990; B. D. Hames et al. (eds.) Nucleic Acid Hybridisation: A Practical Approach, IRL Press, Oxford, 1985; and van Ness et al. (1991) *Nucleic Acids Res.* 19:5143-5151.

Hybridization Probes

In one aspect of the present invention, one or more MGB-oligonucleotide conjugates can be used as probe(s) to identify a target nucleic acid by assaying hybridization between the probe(s) and the target nucleic acid. A probe may be labeled with any detectable label, or it may have the capacity to become labeled either before or after hybridization, such as by containing a reactive group capable of association with a label or by being capable of hybridizing to a secondary labeled probe, either before or after hybridization to the target. Conditions for hybridization of nucleic acid probes are well-known to those of skill in the art. See, for example, Sambrook et al., supra; Ausubel et al., supra; Innis et al., supra; Hames et al. supra; and van Ness et al., supra.

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe or interaction between surface-bound and probe-conjugated ligands) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; etc. See, for example, Falkow et al., U.S. Pat. No. 4,358,535; Urdea et al., U.S. Pat. Nos. 4,868,105 and 5,124,246; Freifelder, *Physical Biochemistry*, Second Edition, W. H. Freeman & Co., San Francisco, 1982; Sambrook, et al., supra; Ausubel et al, supra; Hames et al., supra; and other related references. The duplex-stabilizing capability of MGB-oligonucleotide conjugates makes hybridization possible under more stringent conditions, wherein potentially occluding secondary structure in the target nucleic acid can be minimized.

Amplification Primers

Amplification procedures are those in which many copies of a target nucleic acid sequence are generated, usually in an exponential fashion, by sequential polymerization and/or ligation reactions. Many amplification reactions, such as PCR, utilize reiterative primer-dependent polymerization reactions. A primer is a nucleic acid that is capable of hybridizing to a second, template nucleic acid and that, once hybridized, is capable of being extended by a polymerizing enzyme (in the presence of nucleotide substrates), using the second nucleic acid as a template. Polymerizing enzymes include, but are not limited to, DNA and RNA polymerases and reverse transcriptases; etc. Conditions favorable for polymerization by different polymerizing enzymes are well-known to those of skill in the art. See, for example, Sambrook et al., supra; Ausubel, et al., supra; Innis et al., supra. Generally, in order to be extendible by a polymerizing enzyme, a primer must have an unblocked 3'-end, preferably a free 3' hydroxyl group. The product of an amplification reaction is an extended primer, wherein the primer has been extended by a polymerizing enzyme.

Thus, in one embodiment of the invention, the methods and compositions disclosed and claimed herein are useful in improved amplification reactions such as PCR. See, e.g., U.S. Pat. Nos. 4,683,202; 4,683,195 and 4,800,159; Mullis and Faloona, supra; and Saiki et al., supra. The polymerization step of PCR is most often catalyzed by a thermostable polymerizing enzyme, such as a DNA polymerase isolated from a thermophilic bacterium, because of the elevated temperatures required for the denaturation step of PCR. As discussed supra, one of the problems heretofore associated with the practice of PCR is the requirement for relatively long oligonucleotide primers, having sufficient hybrid stability to serve as primers at the elevated temperatures under which PCR is conducted. MGB-oligonucleotide conjugates are useful as primers in amplification reactions such as PCR, since conjugation of a MGB to an oligonucleotide increases hybrid stability, thereby significantly extending the lower limit of useful primer length. In addition, MGB-oligonucleotide conjugates are useful in specialized PCR protocols wherein reduced primer length is desirable. These include, but are not limited to, differential display, in which optimal primer length is below 10 nucleotides, random amplification of polymorphism in DNA (RAPD) techniques, and amplification length polymorphism analyses. Liang et al, supra; Williams et al., supra.

The improvements provided by the present invention are applicable to any type of assay or procedure in which PCR or a related amplification technique is used, including, but not limited to, hydrolyzable probe assays, priming with allele-specific oligonucleotides (ASOs), fragment length polymorphism analysis, single nucleotide polymorphism (SNP) analysis and microsatellite analysis, for example. These and other techniques are useful in gene mapping, in the identification and screening of disease-related genes, and in pharmacogenetics, to name just a few applications.

Assays Utilizing Labeled Probes; Including Hydrolyzable Probe Assays

Additional uses for MGB-oligonucleotide conjugates are found in assays in which a labeled probe is hybridized to a target and/or an extension product of a target, and a change in the physical state of the label is effected as a consequence of hybridization. A probe is a nucleic acid molecule that is capable of hybridizing to a target sequence in a second nucleic acid molecule. By way of example, one assay of this type, the hydrolyzable probe assay, takes advantage of the fact that many polymerizing enzymes, such as DNA polymerases, possess intrinsic 5'-3' exonucleolytic activities. Accordingly, if a probe is hybridized to a sequence that can serve as a template for polymerization (for instance, if a probe is hybridized to a region of DNA located between two amplification primers, during the course of an amplification reaction), a polymerizing enzyme that has initiated polymerization at an upstream amplification primer is capable of exonucleolytically digesting the probe. Any label attached to such a probe will be released, if the probe is hybridized to its target and if amplification is occurring across the region to which the probe is hybridized. Released label is separated from labeled probe and detected by methods well-known to those of skill in the art, depending on the nature of the label. For example, radioactively labeled fragments can be separated by thin-layer chromatography and detected by autoradiography; while fluorescently-labeled fragments can be detected by irradiation at the appropriate excitation wavelengths with observation at the appropriate emission wavelengths. See, e.g., U.S. Pat. No. 5,210,015.

In a variation of this technique, a probe contains both a fluorescent label and a quenching agent, which quenches the fluorescence emission of the fluorescent label. In this case, the fluorescent label is not detectable until its spatial relationship to the quenching agent has been altered, for example by exonucleolytic release of the fluorescent label from the probe. Thus, prior to hybridization to its target sequence, the dual fluorophore/quencher labeled probe does not emit fluorescence. Subsequent to hybridization of the fluorophore/quencher-labeled probe to its target, it becomes a substrate for the exonucleolytic activity of a polymerizing enzyme which has initiated polymerization at an upstream primer. Exonucleolytic degradation of the probe releases the fluorescent label from the probe, and hence from the vicinity of the quenching agent, allowing detection of a fluorescent signal upon irradiation at the appropriate excitation wavelengths. This method has the advantage that released label does not have to be separated from intact probe. Multiplex approaches utilize multiple probes, each of which is complementary to a different target sequence and carries a distinguishable label, allowing the assay of several target sequences simultaneously.

The use of MGB-oligonucleotide conjugates in this and related methods allows greater speed, sensitivity and discriminatory power to be applied to these assays. In particular, the enhanced ability of MGB-oligonucleotide conjugates to allow discrimination between a perfect hybrid and a hybrid containing a single-base mismatch will facilitate the use of hydrolyzable probe assays in the identification of single-nucleotide polymorphisms and the like. Examples 2 and 3, infra, provide several examples of the utility of MGB-oligonucleotide conjugates in this type of assay. It will be clear to those of skill in the art that compositions and methods, such as those of the invention, that are capable of discriminating single-nucleotide mismatches will also be capable of discriminating between sequences that have multiple mismatches with respect to one another.

Fluorescence Energy Transfer

In further embodiments of the invention, MGB-oligonucleotide conjugates can be used in various techniques which involve multiple fluorescently-labeled probes. In some of these assays, fluorescence and/or changes in properties of a fluorescent label are used to monitor hybridization. For example, fluorescence resonance energy transfer (FRET) has been used as an indicator of oligonucleotide hybridization. In one embodiment of this technique, two probes are used, each containing a different fluorescent label. One of the labels is a fluorescence donor, and the other is a fluorescence acceptor, wherein the emission wavelengths of the fluorescence donor overlap the absorption wavelengths of the fluorescence acceptor. The sequences of the probes are selected so that they hybridize to adjacent regions of a target nucleic acid, thereby bringing the fluorescence donor and the fluorescence acceptor into close proximity, if target is present. In the presence of target nucleic acid, irradiation at wavelengths corresponding to the absorption wavelengths of the fluorescence donor will result in emission from the fluorescence acceptor. These types of assays have the advantage that they are homogeneous assays, providing a positive signal without the necessity of removing unreacted probe. For further details and additional examples, see, for example, European Patent Publication 070685; and Cardullo, et al. (1988) *Proc. Natl. Acad. Sci. USA* 85: 8790-8794. Additional embodiments of the present invention will be found in these and related techniques in which interactions between two different oligonucleotides that are hybridized to the same target nucleic acid are measured. The selection of appropriate fluorescence donor/fluorescence acceptor pairs will be apparent to one of skill in the art, based on the principle that, for a given pair, the emission wavelengths of the fluorescence donor will overlap the absorption wavelengths of the fluorescence acceptor. The enhanced ability of MGB-oligonucleotide conjugates to distinguish perfect hybrids from hybrids containing a single base mismatch facilitates the use of FRET-based techniques in the identification of single-nucleotide polymorphisms and the like.

Use of MGB-Oligonucleotide Conjugates in Assays Involving Fluorescence Quenching In a further embodiment of the invention, MGB-oligonucleotide conjugates are useful in assays which utilize the principles of fluorescence quenching. In one version of this type of assay, the principles of fluorescence quenching are combined with those of hydrolyzable probes, as discussed supra. In this case, an oligonucleotide probe contains a fluorescent label at one end (usually the 5'-end) and a quenching agent at the opposite end (usually the 3'-end). Exemplary fluorescent labels include, but are not limited to, fluoresceins, cyanines, rhodamines and phycoerythrins. Exemplary quenching agents include, but are not limited to, rhodamines, including tetramethylrhodamine (TAMRA), and compound capable of absorbing UV or visible light. The preferred labels are fluorescein and its derivatives and preferred quenching agents are rhodamine derivatives, particularly TAMRA. When the probe is free in solution or hybridized to its target, irradiation of the fluorophore at the appropriate excitation wavelengths fails to cause fluorescent emission, due to the proximity of the quenching agent to the fluorophore on the oligonucleotide. However, if probe, that has hybridized to its target, is subjected to exonucleolytic hydrolysis by a polymerizing enzyme that has initiated polymerization at an upstream primer, the fluorophore will be released from the oligonucleotide. Subsequent to its release from the oligonucleotide, the fluorophore will be capable of fluorescing upon excitation at the appropriate wavelengths, since it has been released from the vicinity of the quencher. MGB-oligonucleotide conjugates, by enhancing the ability to distinguish perfect hybrids from hybrids containing a single base mismatch, facilitate the use of oligonucleotides containing fluorophore/quencher combinations in the identification of single-nucleotide polymorphisms and the like. Exemplary oligonucleotides for use in this aspect of the invention contain a conjugated fluorophore, a conjugated quencher and a conjugated MGB. This type of assay is becoming increasingly important, especially in clinical applications, because it is a homogeneous assay (i.e., no product separation steps are required for analysis) in which the results can be monitored in real time. See, for example, Wittwer et al. (1997) *BioTechniques* 22:130-138. Rapid, fluorescence-based molecular assays find use in, for example, real-time surgical and therapeutic applications, as well.

Additional assays involving the principles of fluorescence quenching will be apparent to those skilled in the art, as will the advantages of using MGB-oligonucleotide conjugates in such assays. It will also be clear to those of skill in the art that fluorescently-labeled MGB-oligonucleotide conjugates provide improvements in speed, sensitivity, specificity and discriminatory power in the practice of all types of hybridization assays.

PCR Clamping

As described herein, the ability of a MGB-oligonucleotide conjugate (in which the MGB is conjugated to the 5'-end of the oligonucleotide) to block elongation from an upstream primer demonstrates that MGB-oligonucleotide conjugates find use and provide improvements in techniques such as PCR clamping. See, for example, Giovannangeli et al. (1993) *Proc. Natl. Acad. Sci. USA* 90:10013-10017. Additional modifications of MGB-oligonucleotide conjugates as described Infra, such as inclusion of phosphorothioate or other modified internucleotide linkages at the 5'-end of the oligonucleotide, will further increase the usefulness of the compositions of the invention in techniques such as PCR clamping.

Assays Involving Oligonucleotide Ligation

MGB-oligonucleotide conjugates are useful in assays in which two or more oligonucleotides, complementary to adjacent sites on a target nucleic acid, are hybridized to adjacent sites on the target nucleic acid and ligated to one another. See, for example, European Patent Publication 320,308; European Patent Publication 336,731; and U.S. Pat. No. 4,883,750. Conditions for ligation are well-known to those of skill in the art. See, for example, Sambrook et al., supra; Ausubel, et al., supra; Innis et al., supra. Ligated nucleic acids can be identified, for example, by an increase in size of the product compared to the starting oligonucleotides. The ability to use shorter oligonucleotides in these types of ligation assay enables smaller, more precise regions of sequence to be probed, which is especially useful in assays based on short regions of homology. Also, as in the case with hybridization assays, use of MGB-oligonucleotide conjugates in ligation assays involving ligation of oligonucleotides allows more efficient discrimination between perfect hybrids and single-base mismatches, which is especially important in oligonucleotide ligation assays. Furthermore, ligation assays often have very narrow temperature optima. The ability of MGB conjugation to raise the $T_m$ of an oligonucleotide allows the temperature optima of ligation assays to be expanded.

cDNA Synthesis

The high binding affinity of MGB-oligonucleotide conjugates enables hybridization of shorter oligonucleotides under more stringent conditions. This is important in the synthesis of cDNA from a mRNA template. cDNA synthesis, as commonly practiced, utilizes a reverse transcriptase enzyme to copy a mRNA template into cDNA. The primer for reverse transcription is normally oligodeoxythymidylate, which is complementary to the polyadenylate tail found at the 3' end of most mRNA molecules. Because hybridization between oligodeoxythymidylate and polyadenylate is relatively weak, cDNA synthesis reactions must usually be conducted under conditions of low stringency. However, under such conditions, mRNA molecules are known to readily adopt intramolecular secondary structures, which act as blocks to elongation by reverse transcriptase, leading to production of short, partial cDNA molecules. The increased hybridization strength of MGB-oligonucleotide conjugates allows cDNA synthesis to proceed under more stringent conditions, wherein secondary structure in the mRNA template is minimized, leading to the synthesis of longer cDNA products. Hence, a MGB-oligonucleotide conjugate is used as a primer for cDNA synthesis and is extended by a polymerizing enzyme in the synthesis of a cDNA molecule. As an example, oligodeoxythymidylate conjugated to a MGB is used as a primer for cDNA synthesis. MGB-oligonucleotide conjugates in which the oligonucleotide sequence is complementary to an internal region of a mRNA template, can also be used for cDNA synthesis. Similarly, MGB-oligonucleotide conjugates ban be used in procedures such as cDNA indexing, described supra. Accordingly, use of the methods and compositions of the invention allows longer cDNA molecules to be obtained, compared to those obtained by the practices of the prior art.

Nucleic Acid Sequencing Systems

In one embodiment of the invention, a collection of all possible n-mer oligonucleotides (where n is an integer less than about 10) are used in a hydrolyzable probe assay to determine a nucleotide sequence. Each oligonucleotide is uniquely labeled and analysis of released label indicates which of the oligonucleotides has hybridized to the target sequence. Alignment of the sequences of the oligonucleotides which have hybridized provides the nucleotide sequence.

MGB-oligonucleotide conjugates are also useful in primer-dependent methods of DNA sequencing, such as the chain-termination method and its derivatives, originally described by Sanger et al., supra. Use of MGB-oligonucleotide conjugates in chain-termination sequencing allows the use of shorter primers at higher stringency, and enables a greater degree of mismatch discrimination during sequencing. Examples include, but are not limited to, a search for genes sharing a short region of homology (on the order of a few amino acids) and sequencing in a region in which very little existing sequence information is available. MGB-oligonucleotide conjugates are useful in such short primer sequencing techniques.

Oligonucleotide Arrays

In another embodiment of the present invention, MGB-oligonucleotide conjugates are also useful in procedures which utilize arrays of oligonucleotides, such as sequencing by hybridization and array-based analysis of gene expression. In these procedures, an ordered array of oligonucleotides of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. See, for example, U.S. Pat. Nos. 5,492,806; 5,525,464; 5,556,752; and PCT Publications WO 92/10588 and WO 96/17957. Materials for construction of arrays include, but are not limited to, nitrocellulose, glass, silicon wafers, optical fibers and other materials suitable for construction of arrays such as are known to those of skill in the art.

A major problem with current array-based sequencing and analysis methods is that, since the different oligonucleotides in an array will have different base compositions, each will have a different $T_m$. Hence, it is difficult to determine the stringency conditions that will provide maximum sensitivity, while retaining the ability to distinguish single-base mismatches, which is a particularly important consideration for most, if not all, applications of array technology. Use of MGB-oligonucleotide conjugates in array-based sequencing and analysis techniques provides a solution to this problem, because conjugation of a MGB to an oligonucleotide makes its $T_m$ relatively independent of base composition. Thus, for a population of MGB-oligonucleotide conjugates of a given length, the $T_m$ for a perfect hybrid falls within a relatively narrow temperature range regardless of sequence. At the same time, the $T_m$ for a single nucleotide mismatch is well below the $T_m$ of the perfect match. See Examples 5 and 6, Tables 11 and 12, supra, where data are presented to show that, while differences in $T_m$ related to base composition are minimized for MGB-oligonucleotide conjugates, the conjugates nevertheless retain their discriminatory ability. Thus, arrays designed such that all oligonucleotides are the same length and are present as their MGB conjugates exhibit minimal variation in $T_m$ among the different oligonucleotides in the array, enabling more uniform hybridization conditions for the entire array. A further advantage to the use of MGB-oligonucleotide conjugates in these techniques is that it provides greater sensitivity, by allowing the use of shorter oligonucleotides, at higher temperatures (and hence higher stringency), while retaining single-nucleotide resolution.

An additional application of the present invention to array technology is in the examination of patterns of gene expression in a particular cell or tissue. In this case, oligonucleotides or polynucleotides corresponding to different genes are arrayed on a surface, and a nucleic acid sample from a particular cell or tissue type, for example, is incubated with the array under hybridization conditions. Detection of the sites on the array at which hybridization occurs allows one to determine which oligonucleotides have hybridized, and hence which genes are active in the particular cell or tissue from which the sample was derived.

Array methods can also be used for identification of mutations, where wild-type and mutant sequences are placed in an ordered array on a surface. Hybridization of a polynucleotide sample to the array under stringent conditions, and determination of which oligonucleotides in the array hybridize to the polynucleotide, allows determination of whether the polynucleotide possesses the wild-type or the mutant sequence. The increased discriminatory abilities of MGB-oligonucleotide conjugates are especially useful in this application of array technology.

Structural Considerations

Oligonucleotide, polynucleotide and nucleic acid are used interchangeably to refer to single- or double-stranded polymers of DNA or RNA (or both) including polymers containing modified or non-naturally-occurring nucleotides, or to any other type of polymer capable of stable base-pairing to DNA or RNA including, but not limited to, peptide nucleic acids (Nielsen et al. (1991) *Science* 254:1497-1500; and Demidov et al. (1995) *Proc. Natl. Acad. Sci. USA* 92:2637-2641), bicyclo DNA oligomers (Bolli et al. (1996) *Nucleic Acids Res.* 24:4660-4667) and related structures. One or more MGB moieties and/or one or more labels, quenching agents, etc. can be attached at the 5' end, the 3' end or in an internal portion of the oligonucleotide. Preferred MGB moieties include multimers of 1,2-dihydro-(3H)-pyrrolo[3,2-e]indole-7-carboxylate and multimers of N-methylpyrrole-4-carbox-2-amide. Particularly preferred are the trimer of 1,2-dihydro-(3H)-pyrrolo[3,2-e]indole-7-carboxylate (CDPI$_3$) and the pentamer of N-methylpyrrole-4-carbox-2-amide (MPC$_5$).

Modified nucleotides including pyrazolopyrimidines (PCT WO 90/14353; and co-owned U.S. patent application, Attorney Docket No. 34469-20005.00, filed even date herewith), 7-deazapurines and their derivatives are preferred; additional modified nucleotides are known to those of skill in the art. Oligonucleotides can be obtained from nature or, more preferably, chemically synthesized using techniques that are well-known in the art. See, for example, Caruthers, U.S. Pat. No. 4,458,066. Enzymatic synthesis and/or modification of oligonucleotides is also encompassed by the present invention. Preferred in the present invention are DNA oligonucleotides that are single-stranded and have a length of 100 nucleotides or less, more preferably 50 nucleotides or less, still more preferably 30 nucleotides or less and most preferably 20 nucleotides or less.

MGB-oligonucleotide conjugates can comprise one or more modified bases, in addition to the naturally-occurring bases adenine, cytosine, guanine, thymine and uracil. Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. All tautomeric forms of naturally-occurring bases, modified bases and base analogues are useful in the MGB-oligonucleotide conjugates of the invention.

Similarly, modified sugars or sugar analogues can be present in one or more of the nucleotide subunits of a MGB-oligonucleotide conjugate. Sugar modifications include, but are not limited to, attachment of substituents to the 2', 3' and/or 4' carbon atom of the sugar, different epimeric forms of the sugar, differences in the α- or β-configuration of the glycosidic bond, anomeric changes, etc. Sugar moieties include, but are not limited to, pentose, deoxypentose, hexose, deoxyhexose, ribose, deoxyribose, glucose, arabinose, pentofuranose, xylose, lyxose, and cyclopentyl.

Modified internucleotide linkages can also be present in MGB-oligonucleotide conjugates. Such modified linkages include, but are not-limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate and the like. Various modifications of bases, sugars and/or internucleotide linkages, that are compatible with their use in oligonucleotides serving as probes and/or primers, will be apparent to those of skill in the art.

Modified bases for use in the present invention also include, but are not limited to, pyrazolo[3,4-d]pyrimidine analogues of adenine and guanine, as disclosed in co-owned PCT Publication WO 90/14353. Preferred base analogues of this type include the guanine analogue 6-amino-1H-pyrazolo[3,4-d]pyrimidin-4(5H)-one (ppG) and the adenine analogue 4-amino-1H-pyrazolo[3,4-d]pyrimidine (ppA). Also of use is the xanthine analogue 1H-pyrazolo[3,4-d]pyrimidin-4(5H)-6(7H)-dione (ppX). These base analogues, when present in an oligonucleotide, strengthen hybridization and improve mismatch discrimination. See co-owned, copending U.S. patent application Ser. No. 09/054,832, filed even date herewith. Example 3, infra, shows the beneficial effect of including a pyrazolo[3,4-d]pyrimidine base analogue in a MGB-oligonucleotide conjugate used in a hydrolyzable probe assay (FIGS. 5 and 6). Modified bases for use in the present invention can also include those for use in selective binding complementary oligonucleotides, as disclosed in co-owned PCT Publication WO97/12896. Particularly preferred are those which modify the minor groove, such as 2-amino adenine and 2-thiothymine.

MGB-oligonucleotide conjugates can contain other pendant moieties, in addition to the MGB. Examples include, but are not limited to, detectable labels (see elsewhere in the present specification); crosslinking agents such as those disclosed in U.S. Pat. No. 5,659,022 and PCT Publications WO 90/14353, WO93/03736, WO94/17092, and WO96/40711; tail moieties such as those disclosed in U.S. Pat. Nos. 5,419, 966 and 5,512,667; peptide linkers such as those disclosed in U.S. Pat. No. 5,574,142; sterols and other lipohilic groups such as those disclosed in U.S. Pat. No. 5,646,126; intercalating agents, reporter groups, electrophilic groups and chelating agents, such as are known to those of skill in the art, and other pendant moieties known to those of skill in the art.

The MGB can be attached at either or both ends of the oligonucleotide. In addition or alternatively, one or more MGBs can be attached in the interior of the oligonucleotide, depending on the length of the oligonucleotide. In general, conjugation of a MGB to either end of an oligonucleotide would provide the greatest degree of hybrid stability, since melting of an oligonucleotide duplex begins at the termini. Nonetheless, if both ends of a duplex formed by an oligonucleotide are relatively stable, for example, due to a high G+C content, attachment of a MGB in the interior of an oligonucleotide (for instance, near an A+T-rich sequence)

could also enhance stability. The intended use of the MGB-oligonucleotide conjugate may also place limitations on the location of the conjugated MGB. For instance, if an oligonucleotide is designed to be used as a primer, the 3'-hydroxy group must be free and capable of being elongated by a polymerizing enzyme. Alternatively, an assay that requires an oligonucleotide possessing a labeled 5'-end would require internal or 3'-end attachment of a MGB.

The location of a MGB within a MGB-oligonucleotide conjugate might also affect the discriminatory properties of such a conjugate. An unpaired region within a duplex will result in changes in the shape of the minor groove in the vicinity of the mispaired base(s). Since MGBs fit best within the minor groove of a perfectly-matched DNA duplex, mismatches resulting in shape changes in the minor groove would reduce binding strength of a MGB to a region containing a mismatch. Hence, the ability of a MGB to stabilize such a hybrid would be decreased, thereby increasing the ability of a MGB-oligonucleotide conjugate to discriminate a mismatch from a perfectly-matched duplex. On the other hand, if a mismatch lies outside of the region complementary to a MGB-oligonucleotide conjugate, discriminatory ability for unconjugated and MGB-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of MGB-oligonucleotides conjugates in this context lies in the fact that much shorter oligonucleotides compared to those used in the prior art (i.e., 20-mers or shorter), having greater discriminatory powers, can be used, due to the pronounced stabilizing effect of MGB conjugation.

It has also been discovered that substitution of inosine for guanosine in a MGB-oligonucleotide conjugate can enhance hybrid stability. Without wishing to be bound by any particular theory, it is likely that inosine substitution makes the local shape of the minor groove more favorable for interaction with a MGB, thereby increasing the strength of the MGB-minor groove interaction. This contribution to duplex stability offsets the weaker base-pairing of the I:C base pair compared to the G:C base pair. Example 4 provides data showing increased $T_m$s for hybrids in which one of the strands is an inosine-containing oligonucleotide.

It will be apparent to those of skill in the art that additional minor groove binding moieties, related to those disclosed herein, will function similarly to facilitate hybridization and primer function of oligonucleotides.

Labels

MGB-oligonucleotide conjugates can be labeled with any label known in the art of nucleic acid chemistry. Detectable labels or tags suitable for use with nucleic acid probes are well-known to those of skill in the art and include, but are not limited to, radioactive isotopes, chromophores, fluorophores, chemiluminescent and electrochemiluminescent agents, magnetic labels, immunologic labels, ligands and enzymatic labels. Suitable labels further include mass labels and those used in deconvolution of combinatorial chemistry libraries, for example, tags that can be recognized by high performance liquid chromatography (HPLC), gas chromatography, mass spectrometry, etc.

Methods for probe labeling are well-known to those of skill in the art and include, for example, chemical and enzymatic methods. By way of example, methods for incorporation of reactive chemical groups into oligonucleotides, at specific sites, are well-known to those of skill in the art. Oligonucleotides containing a reactive chemical group, located at a specific site, can be combined with a label attached to a complementary reactive group (e.g., an oligonucleotide containing a nucleophilic reactive group can be reacted with a label attached to an electrophilic reactive group) to couple a label to a probe by chemical techniques. Exemplary labels and methods for attachment of a label to an oligonucleotide are described, for example, in U.S. Pat. No. 5,210,015; Kessler (ed.),*Nonradioactive Labeling and Detection of Biomolecules*, Springer-Verlag, Berlin, 1992; Kricka (ed.) *Nonisotopic DNA Probe Techniques*, Academic Press, San Diego, 1992; Howard (ed.) *Methods in Nonradioactive Detection*, Appleton & Lange, Norwalk, 1993. Non-specific chemical labeling of an oligonucleotide can be achieved by combining the oligonucleotide with a chemical that reacts, for example, with a particular functional group of a nucleotide base, and simultaneously or subsequently reacting the oligonucleotide with a label. See, for example, Draper et al. (1980) *Biochemistry* 19:1774-1781. Enzymatic incorporation of label into an oligonucleotide can be achieved by conducting enzymatic modification or polymerization of an oligonucleotide using labeled precursors, or by enzymatically adding label to an already-existing oligonucleotide. See, for example, U.S. Pat. No. 5,449,767. Examples of modifying enzymes include, but are not limited to, DNA polymerases, reverse transcriptases, RNA polymerases, etc. Examples of enzymes which are able to add label to an already-existing oligonucleotide include, but are not limited to, kinases, terminal transferases, ligases, glycosylases, etc.

In certain embodiments of the present invention, MGB-oligonucleotide conjugates comprising fluorescent labels (fluorophores) and/or fluorescence quenching agents are used. In a preferred embodiment, a MGB-oligonucleotide conjugate contains both a fluorophore and a quenching agent. Fluorescent labels include, but are not limited to, fluoresceins, rhodamines, cyanines, phycoerythrins, and other fluorophores as are known to those of skill in the art. Quenching agents are those substances capable of absorbing energy emitted by a fluorophore so as to reduce the amount of fluorescence emitted (i.e., quench the emission of the fluorescent label). Different fluorophores are quenched by different quenching agents. In general, the spectral properties of a particular fluorophore/quenching agent pair are such that one or more absorption wavelengths of the quencher overlaps one or more of the emission wavelengths of the fluorophore. A preferred fluorophore/quencher pair is fluorescein/tetramethylrhodamine; additional fluorophore/quencher pair can be selected by those of skill in the art by comparison of emission and excitation wavelengths according to the properties set forth above.

For use in an amplification assay which involves elevated temperatures, such as PCR, or other procedures utilizing thermostable enzymes, the label will be stable at elevated temperatures. For assays involving polymerization, the label will be such that it does not interfere with the activity of the polymerizing enzyme. Label can be present at the 5' and/or 3' end of the oligonucleotide, and/or may also be present internally. The label can be attached to any of the base, sugar or phosphate moieties of the oligonucleotide, or to any linking group that is itself attached to one of these moieties.

EXAMPLES

Example 1

MGB-oligonucleotide Conjugates as PCR Primers

In this example, we show that a modification which greatly improves hybrid stability of a short oligonucleotide also allows the oligonucleotide to serve as a PCR primer. CDPI$_3$; the trimer of 1,2-dihydro-(3H)-pyrrolo[3,2-e]indole-7-carboxylate, or CDPI; is a synthetic non-reactive derivative of a subunit of the antitumor antibiotic CC-1065 (Hurley et al. (1984) *Science* 226:843-844). This oligopeptide is a DNA minor groove binder (MGB), with a very high affinity for the minor groove of A-T-rich double-stranded DNA. It has previously been reported that, when compared to unmodified oligonucleotides of the same length, CDPI$_3$-oligonucleotide conjugates form unusually stable and specific hybrids with complementary single-stranded DNA (Lukhtanov et al (1995) *Bioconjugate Chem.* 6:418-426; Afonina et al. (1996) *Proc. Nail. Acad. Sci. USA* 93:3199-3204). This example demonstrates that conjugates of short oligonucleotides with CDPI$_3$ make effective primers for PCR, thus improving the yield and accuracy of priming with short primers. Oligonucleotides as short as 8-mers and G-C-rich 6-mers are able to specifically prime the amplification reaction when conjugated to a MGB. Thus, conjugation of a MGB to an oligonucleotide under the conditions described herein does not interfere with the ability of the oligonucleotide 3'-end to be extended by a polymerizing enzyme.

Oligonucleotides and Oligonucleotide Conjugates

Oligonucleotides used in this study were complementary to various regions of the M13mp19 genome. Oligonucleotide synthesis was performed on an Applied Biosystems Model 394 DNA synthesizer using the 1 μmol coupling program supplied by the manufacturer. CDPI$_3$ was postsynthetically conjugated to the 5'-end of ODNs as described (Lukhtanov et al., supra). ODNs were purified by HPLC on a reverse-phase column eluted by an acetonitrile gradient (usually 0-45%) in 100 mM triethylamine acetate (pH 7.5) buffer. Purity of unmodified ODNs was evaluated by electrophoresis on an 8% polyacrylamide-8 M urea gel with subsequent visualization by silver staining (Daiichi). Purity of the oligonucleotide-CDPI$_3$ conjugates was verified by analytical HPLC as described above. All oligonucleotide preparations were >95% pure.

The preparation of CDPI$_3$ is described supra in Reaction scheme 1 and accompanying text, and formation of the MGB-oligonucleotide conjugate was accomplished by reaction of the 2,3,5,6-tetrafluorophenyl ester of CDPI$_3$ with an oligonucleotide with a 5'-aminohexyl phosphate ester (see Reaction Scheme 3, supra). FIG. 2 depicts the CDPI$_3$ molecule and the structures of the linkers through which it is attached to the 5' or 3' ends of an oligonucleotide. The sequences of the oligonucleotides used in this example are shown in Table 6.

Thermal Denaturation Studies

Hybrids formed between MGB-oligonucleotide conjugates or unmodified oligonucleotides and their complements were melted at a rate of 0.5° C./min in 140 mM KCl, 10 mM MgCl$_2$ and 20 mM HEPES-HCl (pH 7.2) on a Lambda 2S (Perkin Elmer) spectrophotometer with a PTP-6 automatic multicell temperature programmer. Each oligonucleotide (2 μM) was mixed with sufficient complementary oligonucleotide to give a 1:1 ratio. Prior to melting, samples were denatured at 100° C. and then cooled to the starting temperature over a 10 min period. The melting temperatures ($T_m$) of the hybrids were determined from the derivative maxima and collected in Table 6. In the "sequence" column of Table 6, MGB refers to the presence of CDPI$_3$ conjugated through a hexylamine linker esterified to the 5'-phosphate group of the oligonucleotide (see FIG. 2).

TABLE 6

Properties of oligonucleotides (ODNs) used in this study

| ODN | $T_m$(° C.) | Length (ntds) | % GC | Sequence | Location on M13mp19 genome | SEQ ID NO. |
|---|---|---|---|---|---|---|
| 1 | 45 | 16 | 37.5 | 5'-ATAAAACAGAGGTGAG-3' | complementary to 4937-4922 | 1 |
| 2 | 39 | 12 | 33.3 | 5'-ATAAAACAGAGG-3' | complementary to 4937-4926 | 2 |
| 2-C | 56 | 12 | 33.3 | 5'-MGB-ATAAAACAGAGG-3' | complementary to 4937-4926 | 2 |
| 3 | 24 | 10 | 20 | 5'-ATAAAACAGA-3' | complementary to 4937-4928 | 3 |
| 3-C | 46 | 10 | 20 | 5'-MGB-ATAAAACAGA-3' | complementary to 4937-4928 | 3 |
| 4 | 50 | 16 | 43.8 | 5'-TAATAACGTTCGGGCA-3' | 4630-4645 | 4 |
| 4-C | 66 | 16 | 43.8 | 5'-MGB-TAATAACGTTCGGGCA-3' | 4630-4645 | 4 |
| 5 | 16 | 6 | 33.3 | 5'-ATAACG-3' | 4632-4637 | 5 |
| 5-C | 36 | 6 | 33.3 | 5'-MGB-ATAACG-3' | 4632-4637 | 5 |
| 6-C | 57 | 12 | 33.3 | 5'-MGB-TAATAACGTTCG-3' | 4630-4641 | 6 |
| 7-C | 49 | 10 | 20 | 5'-MGB-TAATAACGTT-3' | 4630-4639 | 7 |
| 8 | 25 | 8 | 62.5 | 5'-CGGGCAAA-3' | 4640-4647 | 8 |
| 8-C | 33 | 8 | 62.5 | 5'-MGB-CGGGCAAA-3' | 4640-4647 | 8 |
| 9 | 47 | 16 | 43.8 | 5'-CGGGCAAAGGATTTAA-3' | 4640-4655 | 9 |
| 9-C | 53 | 16 | 43.8 | 5'-MGB-CGGGCAAAGGATTTAA-3' | 4640-4655 | 9 |
| 10 | <17 | 6 | 50 | 5'-GGCAAA-3' | 4642-4647 | 10 |
| 10-C | <17 | 6 | 50 | 5'-MGB-GGCAAA-3' | 4642-4647 | 10 |

TABLE 6-continued

Properties of oligonucleotides (ODNs) used in this study

| ODN | $T_m$ (° C.) | Length (ntds) | % GC | Sequence | Location on M13mp19 genome | SEQ ID NO. |
|---|---|---|---|---|---|---|
| 11 | 23 | 8 | 62.5 | 5'-CGGCTCTA-3' | 4720-4727 | 11 |
| 11-C | 37 | 8 | 62.5 | 5'-MGB-CGGCTCTA-3' | 4720-4727 | 11 |
| 12 | 43 | 16 | 37.5 | 5'-CGGCTCTAATCTATTA-3' | 4720-4735 | 12 |
| 12-C | 52 | 16 | 37.5 | 5'-MGB-CGGCTCTAATCTATTA-3' | 4720-4735 | 12 |
| 13 | 34 | 16 | 18.75 | 5'-TATTTTAGATAACCTT-3' | 4756-4771 | 13 |
| 13-C | 56 | 16 | 18.75 | 5'-MGB-TATTTTAGATAACCTT-3' | 4756-4771 | 13 |

PCR Reactions

All PCR reactions were performed on a Perkin-Elmer Cetus DNA Thermocycler and included: PCR buffer (Promega) with no magnesium, 1.6 mM MgCl$_2$, 50 µM dNTP, 50 nM each primer, 0.2 µg M13mp19 DNA and 1-2 Units Taq DNA polymerase (Promega). Final volume for each reaction was 50 µl. The standard PCR profile was as follows: 3 min at 94° C., 30 cycles of 1 min at 94° C., 1.5 min at annealing temperature and 30 s at 72° C., finally followed by 5 min at 72° C. and a 4° C. soak. For the 8-mers and 6-mers, PCR was performed in the touch-down manner (Don, R. H. et al. (1991) *Nucleic Acids Res.* 19: 4008) with a starting annealing temperature of 55° C. for 8-mer primers and 50° C. for 6-mers. Each subsequent cycle had an annealing temperature 1° C. lower until 41° C. (for 8-mers) or 37° C. (for 6-mers) was reached, with the final 15 cycles annealed at these final temperatures. Touch-down PCR has been shown to maximize the yield of product when using short primers (Don, R. H. et al., supra). Amplifications with 16-mer, 12-mer and 10-mer primers were analyzed by electrophoresis of 10 µl of the reaction mixture on a 2% agarose gel and detection of the bands by ethidium bromide staining. Amplifications with 8-mer and 6-mer primers were analyzed by electrophoresis of 5 µl of reaction mixture on an 8% polyacrylamide sequencing gel and detection of the bands by silver staining (Daiichi).

Results

Hybrid Stability

Table 6 presents the melting temperatures ($T_m$s) of duplexes formed by the MGB-ODN conjugates with complementary ODNs, showing the effect of a terminally-conjugated CDPI$_3$ group on duplex stability for duplexes of different lengths and G-C compositions. For the 16-mer duplexes, the largest increase in $T_m$ attributable to a tethered MGB (22° C.), was obtained when that group was flanked by a run of seven A-T base pairs (compare oligonucleotides 13-C and 13). A-T-rich sequences of this length form minor grooves which act as good binding sites for the CDPI$_3$ tripeptide. Of all the hybrids examined, the 16-mer duplex formed by oligonucleotide 4-C gave the highest absolute $T_m$ (66° C.). This unusually high $T_m$ reflects an otherwise G-C-rich duplex which contains six A-T base pairs adjacent to the tethered CDPI$_3$ group. Conversely, a 16-mer duplex with a O—C-rich sequence flanking the MGB conjugation site (12-C) was only 9° C. more stable than the unmodified duplex (12). The CDPI$_3$ group in this duplex binds in a less favorable G-C-rich minor groove.

The $T_m$s reported for the shorter primers in Table 6 follow the same trends as for the 16-mers. The primers with the A-T-rich regions adjacent to the MGB at the 5'-end had higher $T_m$s than those with G-C-rich regions, and they showed a greater increase in $T_m$ compared to their non-conjugated counterparts. The 10-mers 3-C and 7-C, for instance, had $T_m$ values of 46-49° C., well within a range adequate for specific PCR priming.

Priming Ability

The ODNs and MGB-ODN conjugates were tested as PCR primers using M13mp19 single-stranded DNA as the amplification substrate. Typically, unmodified and CDPI$_3$-conjugated versions of the same oligonucleotide were compared. These were tested in parallel, as reverse primers, using a PCR profile in which only the annealing temperature was varied. A lower than usual concentration of primers (<0.1 µM) was employed when using the MGB-oligonucleotide conjugates. This minimized any spurious interaction of these conjugates with A-T-rich sequences due to the anchor effect of the CDPI$_3$ group (Afonina, I. et al., supra). To confirm the specificity of primer binding, the primers were designed such that every amplified product it this study contained a DdeI restriction site. In addition to measuring the size of the amplification product (FIGS. 3 and 4), aliquots of selected PCR reaction mixtures were treated with DdeI and analyzed in a 2% agarose gel. In all cases the expected restriction fragments were obtained.

FIGS. 3A and 3B demonstrate the improved priming performance of 16-mer MGB-ODN conjugates in comparison with unmodified primers. Conditions of amplification were the same with the exception of annealing temperature, which was 45° C. for FIGS. 3A and 68° C. for FIG. 3B. While all of these 16-mer oligonucleotides primed at the lower temperature (FIG. 3A, see legend for predicted product sizes), only those with a 5'-CDPI$_3$ group primed at the higher temperature (FIG. 3B, see legend for predicted product sizes).

FIG. 3C confirms the advantages of conjugation of CDPI$_3$ to short primers 10 or 12 nucleotides long. Both conjugated primers efficiently amplified the expected sequence (see FIG. 3C legend for predicted product sizes). The same primers without a tethered MGB did not generate product detectable by ethidium bromide staining when amplified under the same conditions.

FIG. 4 demonstrates that specific priming is possible even for primers as short as an 8-mer (FIG. 4A) and a 6-mer (FIG. 4B). A 10-mer forward primer was used in these reactions. The low levels of product necessitated the use of touch-down PCR (Don, et al., supra) and detection of bands by silver staining. In each case a band of expected size (see legends to FIGS. 4A and 4B for predicted product sizes) was observed only when the reverse primer was conjugated to a CDPI$_3$ group.

Without wishing to be bound by any particular theory, it appears that the increase in stability of a hybrid comprising a MGB-oligonucleotide conjugate compared to one containing a non-conjugated oligonucleotide is likely to be due to the binding of the tethered MGB in the duplex region. The binding region of the MGB probably spans up to 6 base pairs. Importantly, the 3'-terminus of the MGB-conjugated oligonucleotide is still recognized by the polymerizing enzyme, as primer extension seems to depend only on hybrid stability and is not inhibited by the presence of the MGB.

Example 2

Use of MGB-oligonucleotide Conjugates in a Hydrolyzable Probe Assay

In this example, we show that conjugation of MGBs to short oligonucleotides results in improved hybrid stability and improved discrimination between a perfect hybrid and a single-base mismatch, when MGB-short oligonucleotide conjugates are used in a hydrolyzable probe assay. The procedure described by Wittwer et al. (1997a) *BioTechniques* 22:130-138, was used. In this method, MGB-oligonucleotide conjugates, additionally comprising a fluorophore and a quenching agent, were used as probes in a hydrolyzable probe assay. This type of probe is designed to be complementary to a predicted amplification product, and emits very little or no fluorescence, due to the proximity of the fluorophore to the quenching agent. Formation of a hybrid between the probe and the amplification product produces a structure that is a substrate for exonucleolytic hydrolysis of the probe by a polymerase possessing duplex-specific exonuclease activity, if the polymerase has initiated polymerization at an upstream primer. The exonuclease action will release the fluorophore from the hybridized oligonucleotide and hence from the proximity of the quenching agent, resulting in an increase in fluorescence. Thus, in this assay, increase in fluorescence is dependent upon duplex formation between the fluorophore/quencher-labeled MGB-oligonucleotide conjugate probe and the desired amplification product. See U.S. Pat. No. 5,210,015; Livak et al. (1995) *PCR Meth. App.* 4:357-362; and Heid et al. (1996) *Genome Res.* 6:986-994 for further details.

Synthesis of MGB-oligonucleotide Conjugates Containing Fluorophore(s) and Quencher(s)

CDPI$_3$-CPG Supports (Scheme 6)

4-[(2-Phenyl)-1,3-dioxolan-4-yl]-1-butanol (17). To a solution of 1,2,6-trihydroxyhexane (10.0 g, 74.6 mmol) and benzaldehyde dimethylacetal (15.0 g, 98.7 mmol) in dry DMF (10 mL) was added Amberlyst 15 (5.0 g). The mixture was stirred at 100° C. for 5 min, then cooled and filtered. The filtrate was concentrated and residue obtained was re-dissolved in ethyl acetate. After being washed with water and brine, the solution was dried over Na$_2$SO$_4$. The crude product obtained after evaporation of the solvent was chromatographed on silica eluting with ethyl acetate. Concentration of the proper fractions afforded 11.0 g (66%) of the title product (a mixture of diastereomers) as a colorless oil: $^1$H NMR (CDCl$_3$, 300 MHz, ppm) 7.48 (m, 2H), 7.39 (m, 3H), 5.92 (s, 0.4H), 5.80 (s, 0.6H), 4.3-4.1 (m, 2H), 3.64 (m, 3H), 1.8-1.4 (m, 6H).

2-Phenyl-4-(4-phtalimidobut-1-yl)-1,3-dioxolane (18). A solution of diethyl azodicarboxylate (8.6 g, 49.4 mmol) in 40 mL of THF was slowly added to a cold (ice bath) solution of 17 (10.0 g, 45.0 mmol), triphenylphosphine (13.0 g, 49.5 mmol) and phthalimide (7.3 g, 49.7 mmol) in 60 mL of THF. After being kept at ambient temperature overnight, the solution was concentrated and the residue was triturated with ether (~150 mL) to precipitate triphenylphosphine oxide which was then removed by filtration. The filtrate was concentrated to give an oily residue which was chromatographed on silica eluting with 33% ethyl acetate in hexane. Concentration of the pure product fractions followed by drying under vacuum afforded 14.6 g (92%) of the desired product as a semi-solid (a mixture of diastereomers): $^1$H NMR (CDCl$_3$, 300 MHz, ppm) 7.85 (m, 2H), 7.71 (m, 2H), 7.46 (m, 2H), 7.36 (m, 3H), 5.90 (s, 0.4H), 5.78 (s, 0.6H), 4.3-4.0 (m, 2H), 3.68 (m, 3H), 1.9-1.3 (m, 6H).

6-[N-(9-Fluorenylmethoxycarbonyl)amino]-(R,S)-1,2-hexanediol (19). A suspension of 18 (13.5 g, 38.5 mmol) in 50 mL of ethanol was treated with 1.9 mL (39.1 mmol) of hydrazine monohydrate and heated at reflux for 3 h. The mixture was cooled and acidified with 1M HCl to pH 3. The precipitate formed was filtered off, the filtrate was extracted with ether and concentrated to give a semi-solid. It was suspended in 2-propanol to separate insoluble inorganic salts. After filtration, the solution was concentrated in vacuo to afford 5.0 g of a syrup containing mostly the desired product contaminated with 2-propanol. This material was used in the next reaction without additional purification.

To a solution of the above crude aminodiol in a mixture of methanol (25 mL) and CH$_2$Cl$_2$ (10 mL) was added triethylamine (7 mL) followed by 9-fluorenylmethyl N-succinimidyl carbonate (8.0 g, 23.7 mmol). After being stirred for 1 h, the reaction mixture was treated with acetic acid (5 mL) to neutralize excess triethylamine, and concentrated. Trituration of the residue with water gave a white solid which was washed with water and ether. Drying in vacuo afforded 5.5 g (40%) of analytically pure product: $^1$H NMR (DMSO-d6, 300 MHz, ppm) 7.88 (d, 2H), 7.68 (d, 2H), 7.41 (t, 2H), 7.33 (it 2H), 4.45 (t, 1H), 4.37 (d, 1H), 4.28 (d, 2H), 4.21 (m, 1H), 3.35 (m, 1H), 3.24 (m, 2H), 2.96 (m, 2H), 1.39 (m, 4H), 1.21 (m, 2H).

6-[N-(9-Fluorenylmethoxycarbonyl)amino]-2-O-(4,4'-dimethoxytriphenylmethyl)-(R,S)-1,2-hexanediol (20). To a solution of 19 (2.0 g, 5.6 mmol) in 20 mL of dry pyridine was added N,N-dimethylaminopyridine (0.1 g) and 4,4'-dimethoxytrityl chloride (4.0 g, 11.8 mmol). After being stirred for 2 h, the solution was concentrated and the resultant oily residue was re-dissolved in ethyl acetate. The solution was washed with water, brine and dried over Na$_2$SO$_4$. Evaporation of the solvent gave crude product which was chromatographed on silica eluting with 50% ethyl acetate in hexane. The title product was obtained as a pale yellow amorphous solid (2.8 g, 79%) after evaporation of the solvent: (CDCl$_3$, 300 MHz, ppm) 7.77 (d, 2H), 7.59 (d, 2H), 7.5-7.1 (m, 17H), 6.84 (t, 4H), 4.80 (t, 1H), 4.40 (d, 2H), 4.22 (t, 1H), 3.80 (s, 6H), 3.2-3.0 (m, 4H), 1.6-1.1 (m, 6H).

2,3,5,6-Tetrafluorophenyl-6-[N-(9-fluorenylmethoxycarbonyl)amino]-2-(4,4'-dimethoxytriphenylmethoxy)-hex-1-yl butanedioate (21). To a solution of 20 (1.0 g, 1.6 mmol) in 5 mL of dry pyridine was added succinic anhydride (1.0 g, 10 mmol) followed by 1-methylimidazole (0.02 mL). The reaction mixture was stirred for 8 h at 55° C. and treated with water (1 mL). Concentration under vacuum gave an oil which was partitioned between CHCl$_3$ and cold 10% citric acid. The organic phase was washed with water and dried over Na$_2$SO$_4$. Evaporation of the solvent afforded crude acid as an amorphous solid (0.99 g), this material was taken to the next step without further purification.

To a solution of the above acid in 5 mL of dry CH$_2$Cl$_2$ was added triethylamine (0.25 mL) followed by 0.25 mL (1.4 mmol) 2,3,5,6-tetrafluorophenyl trifluoroacetate. Gamper, H. B. et al. (1993) *Nucleic Acids Res.* 21: 145. After being kept at ambient temperature for 15 min, the solution was applied onto a silica gel column. Elution of the column with 33% ethyl acetate in hexane and concentration of the pure product fractions afforded 1.0 g (71%) of the desired TFP ester as a white, amorphous solid: (CDCl$_3$, 300 MHz, ppm) 7.76 (d, 2H), 7.58 (d, 2H), 7.5-7.1 (m, 17H), 7.00 (m, 1H), 6.84 (t, 4H), 5.1 (m, 1H), 4.79 (t, 1H), 4.38 (d, 2H), 4.22 (t, 1H), 3.78 (s, 6H), 3.2-2.9 (m, 6H), 2.81 (m, 2H), 1.61 (m, 2H), 1.45 (m, 2H), 1.26 (m, 2H).

Preparation of CPG 22. To a solution of 21 (0.5 g, 0.57 mmol) in 20 mL of dry pyridine was added long chain aminoalkyl CPG (500 A) (5.0 g) followed by 1-methylimidazole (1.0 mL). After being swirled for 15 h at ambient temperature, the suspension was treated with acetic anhydride (3 mL) to cap unreacted amino groups (15 min). The CPG was then washed with DMF, acetone, ether and dried. The CPG was analyzed for DMTr content (Atkinson, T. et al. (1984) Solid-Phase Synthesis of Oligodeoxyribonucleotides by Phosphite-Triester Method. In "Oligonucleotide Synthesis, A practical Approach". (M. J. Gait, Ed.) pp. 35-81. IRL Press, Washington, D.C.) and found to have a loading of 49 μmol/g.

Preparation of CPG 23. CPG 22 (2.8 g) was deprotected by a treatment with 20 mL of 0.2 M 1,8-diazobicyclo[5.4.0]undec-7-ene(1, 5-5) (DBU) for 20 min. The CPG was extensively washed with DMF and ether, dried and re-suspended in a solution of CDPI$_3$-TFP (Lukhtanov, E. A. et al. (1995) *Bioconjugate Chem.*, 6: 418) (200 mg) and N,N-diisopropylethylamine (1 mL) in 8 mL of DMF. After being swirled for 3 days, the CPG was washed with N,N,-dimethylacetamide, acetone, ether and dried. Unreacted amino groups were capped by treatment with 10% acetic anhydride in pyridine for 15 min, and the CPG was washed and dried as described above.

Scheme 6: Preparation of CDPI$_3$-CPG support (below)

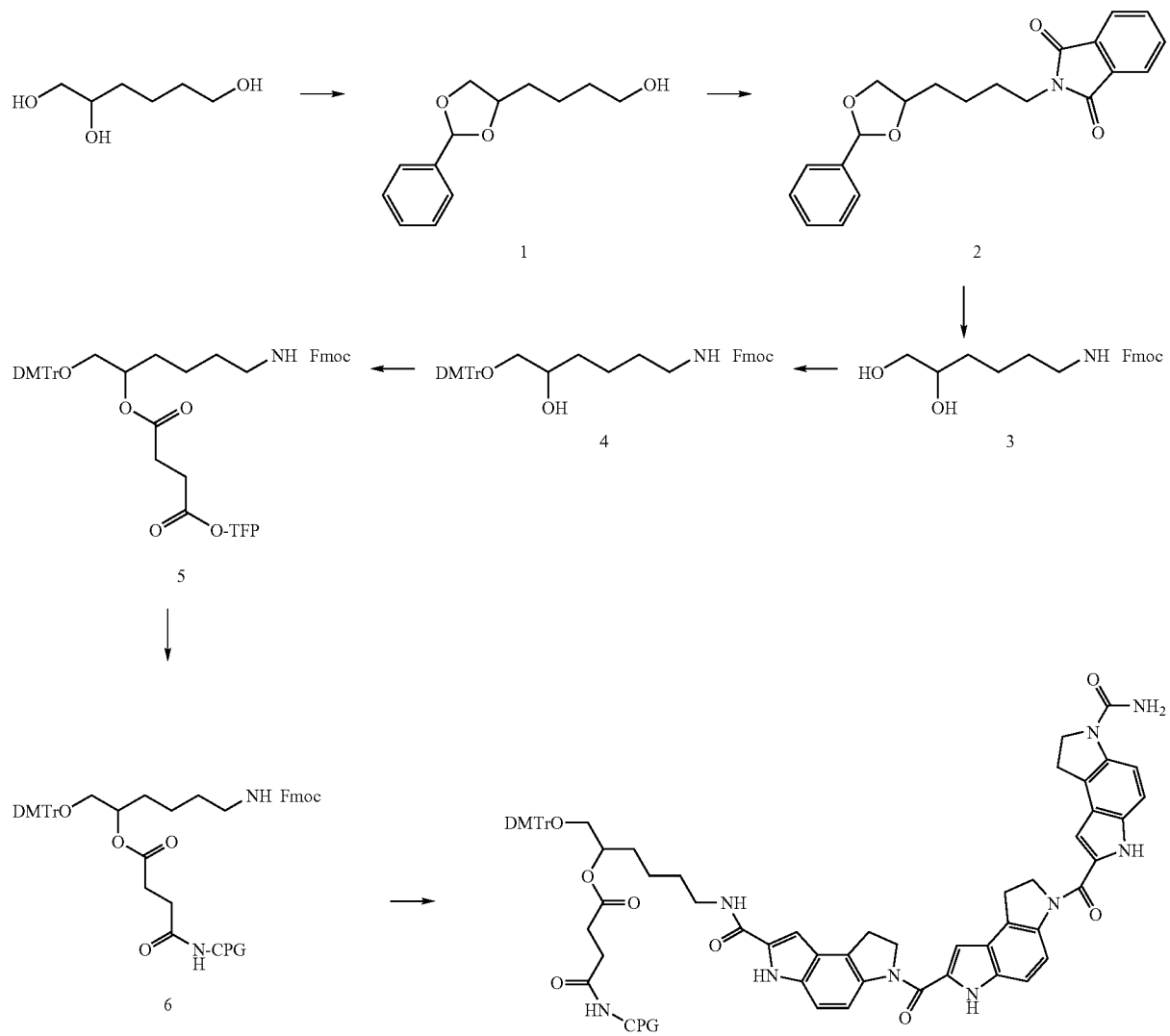

Oligonucleotide synthesis using the CDPI$_3$-CPG support (Scheme 7). Trityl-off 3'-CDPI$_3$ oligonucleotides were prepared in 1 µmol scale using standard 3'-phosphoramidite chemistry on the CDPI$_3$-CPG support (~20-50 mg) on an ABI 394 according to the protocol supplied by the manufacturer with one exception: 0.01 M (instead of the standard 0.1 M) iodine solution in was utilized in the oxidation step to avoid iodination of the CDPI$_3$ moiety. In order to introduce an amino-linker for the postsynthetic incorporation of the TAMRA dye (see below), protected aminopropyl ppG and aminopropyl ppA phosphoramidites were utilized at the desired step instead of the standard guanosine or adenosine phosphoramidites, respectively. See co-owned, PCT WO 90/14353.

Incorporation of 6-FAM and TET Fluorophores (Scheme 8) and Isolation of the Conjugates.

6-FAM (6-carboxyfluorescein) or TET (6-carboxy-4,7,2', 7'-tetrachlorofluorescein) was introduced at the last step of the above-described automated oligonucleotide synthesis using corresponding 6-FAM and TET phosphoramidites (Glen Research) according to the protocol supplied by the manufacturer. After deprotection the modified ODNs were purified by reverse-phase chromatography on a 4.6×250 mm, C-18 column (Dynamax-300, Rainin) eluting with a gradient of acetonitrile (0-60%) buffered at pH 7.5 (0.1 M triethylammonium acetate). The desired fraction was concentrated to a volume of ~50 µL by extraction with n-butanol and then diluted with 2% solution of LiClO$_4$ in acetone (1.2 mL). The Scheme 7: Introduction of 3'-CDPI$_3$ residue using the CDPI$_3$-CPG support (below)

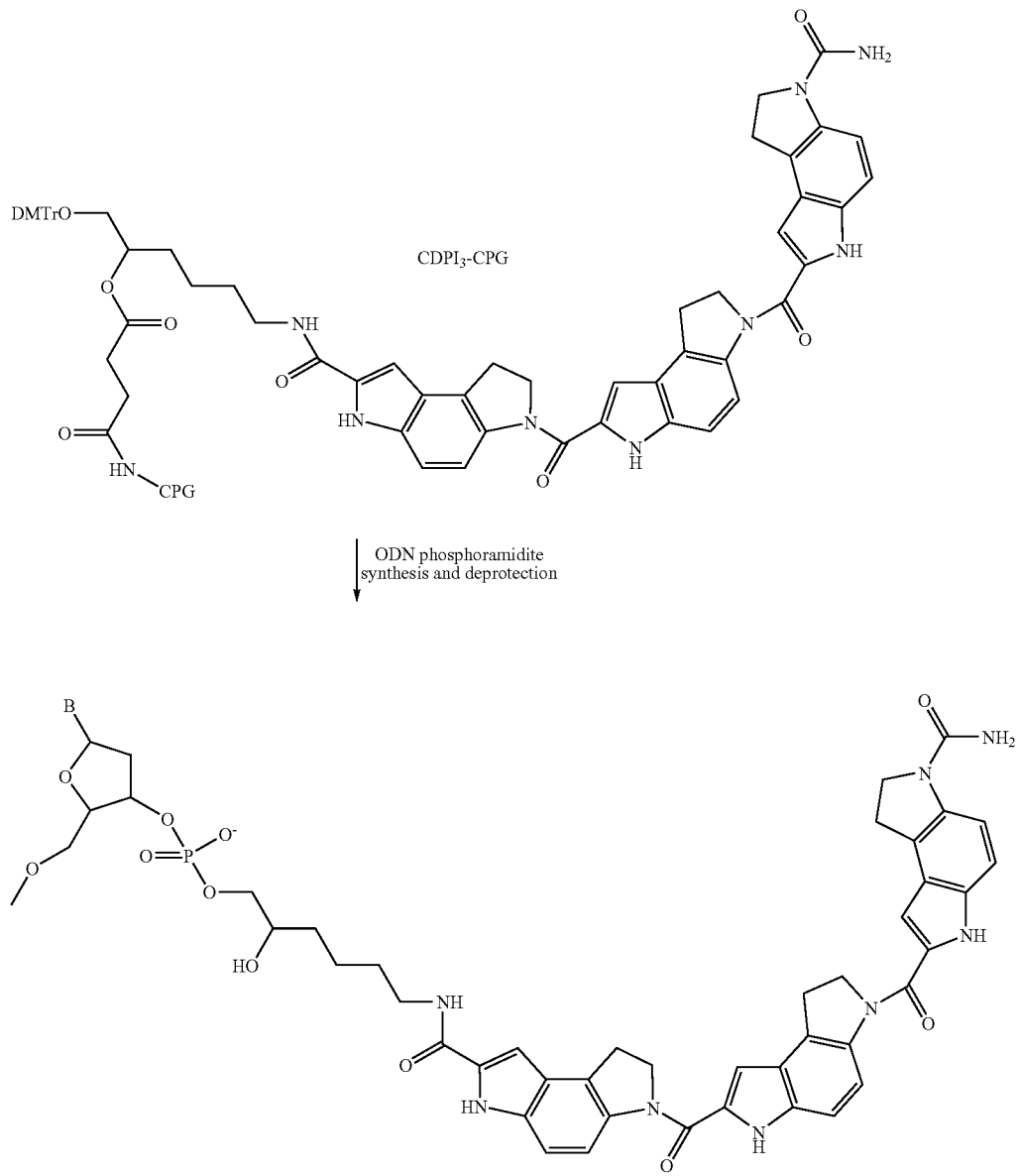

resultant precipitate was collected by centrifugation, the pellet was washed with acetone (2×1.2 mL) and dried under vacuum.

Scheme 8: Introduction of fluorophores at the 5′-end using 6-FAM and TET phosphoramidates (below)

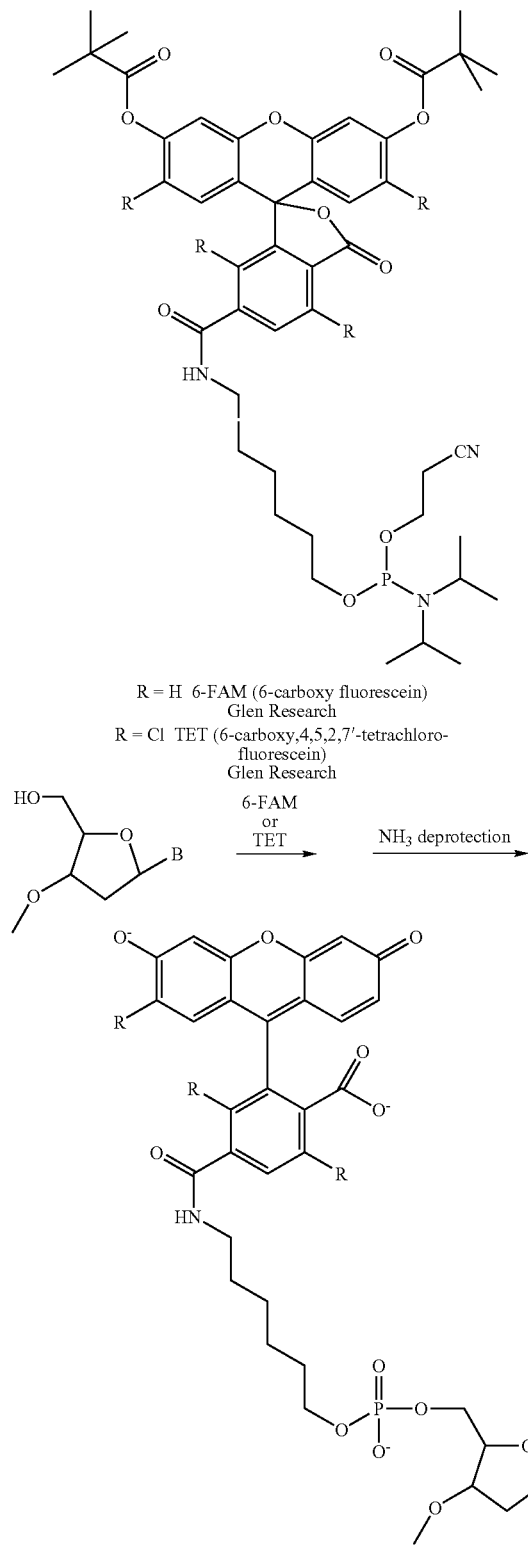

R = H  6-FAM (6-carboxy fluorescein)
Glen Research
R = Cl  TET (6-carboxy,4,5,2′,7′-tetrachlorofluorescein)
Glen Research Postsynthesis introduction of TAMRA residue (Scheme 9). TAMRA (tetramethylrhodamine) was incorporated into the above conjugates by reaction of the oligonucleotide with TAMRA-N-hydroxysuccinimide ester (Glen Research) according to the protocol supplied by the manufacturer. Under these conditions, the TAMRA moiety is added to an amino group linked to a ppG or ppA residue in the oligonucleotide. Purification of the double dye (fluorescein and TAMRA)-labeled CDPI$_3$-ODN conjugates was accomplished by denaturing 20% PAGE, the desired band was cut out and the conjugate extracted by incubation of the gel slice in 0.1 M triethylammonium acetate (10 mL) (pH 7.5) overnight at 37° C. Finally, the conjugates were isolated from the extract by reverse phase HPLC as described above.

Scheme 9: Postsynthesis introduction of TAMRA quencher at the internal ppG or ppA residues (below)

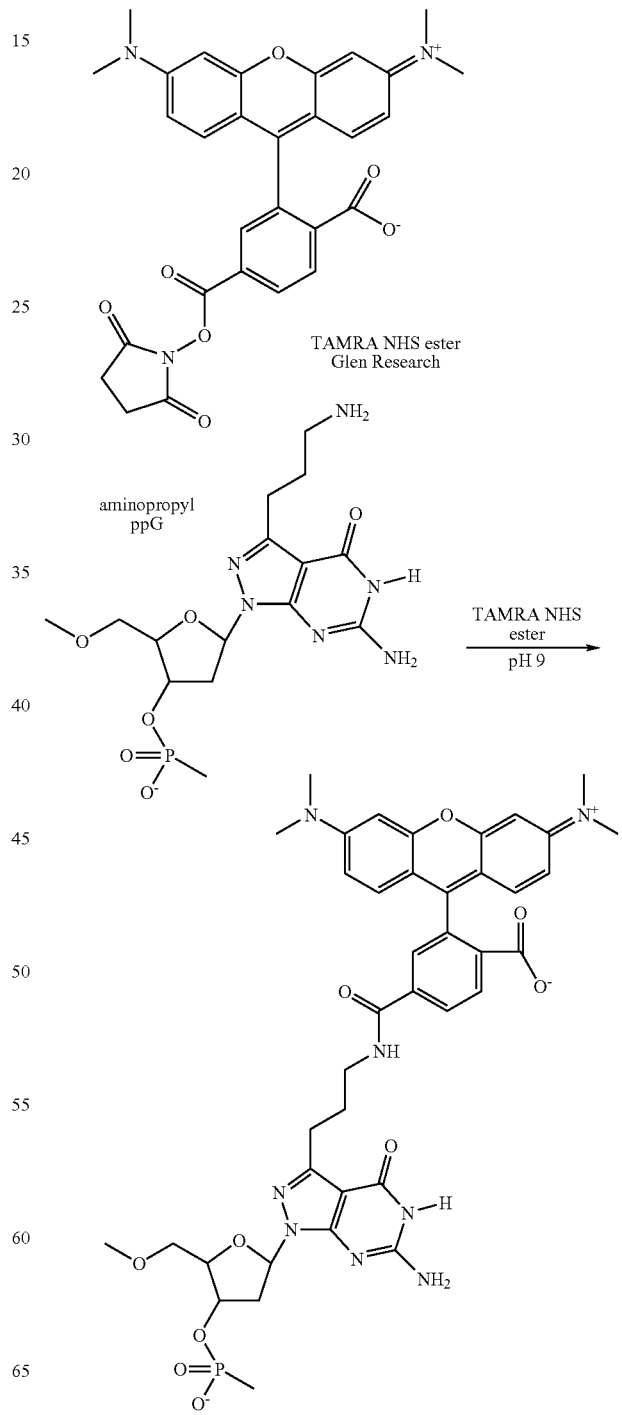

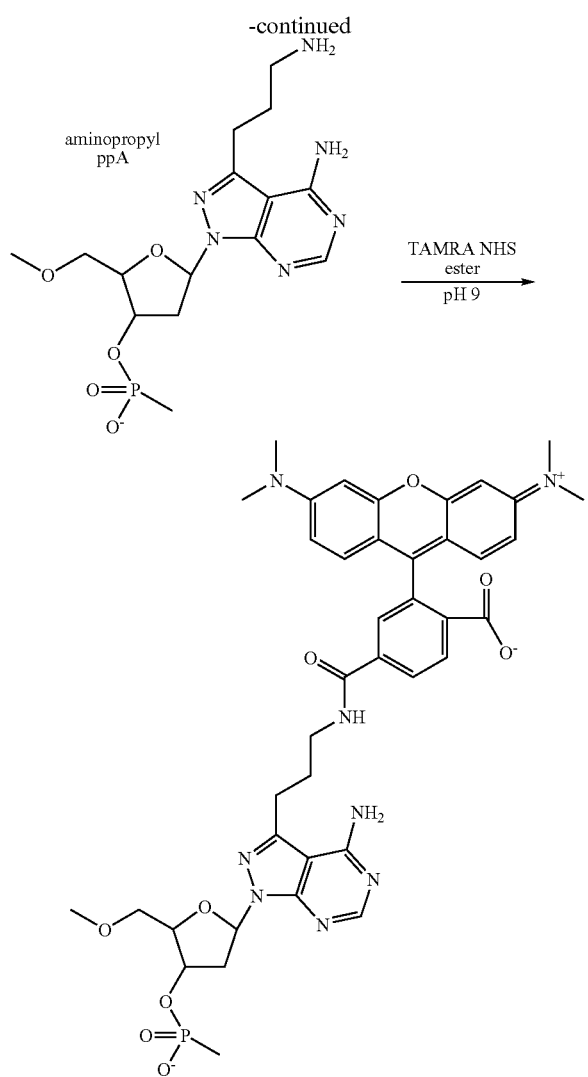

Assay

Reaction mixtures contained 40 mM NaCl, 20 mM Tris-Cl pH 8.9, 5 mM MgSO$_4$, 0.05% (w/v) bovine serum albumin, 125 μM each of the four dNTPs, 1 ng template 0.5 μM each primer, 0.5 μM probe (fluorophore/quencher labeled MGB-oligonucleotide conjugate) and 0.5 μl of Taq Polymerase per 10 μl reaction volume. Forty cycles of amplification were conducted. Each cycle was 0 sec at 94° C. for denaturation (i.e., temperature was raised to 94° C. and immediately lowered to the annealing/elongation temperature), followed by 15 sec at a combined annealing/elongation temperature. The annealing/elongation temperature varied among different reactions and is specified for each particular case.

Assays were conducted following the method of Wittwer et al. (1997a) BioTechniques 22:130-138, and fluorescence measurements were made using a Light Cycler™, available from Idaho Technology. Wittwer et al. (1997b) BioTechniques 22:176-181. Fluorescein fluorescence was determined by excitation at 485 nm and detection of emission between 518-530 nm.

Results

Experiments using different length probes, either unconjugated or conjugated to a MGB (CDPI$_3$) were conducted at various annealing/elongation temperatures. All probes contained a molecule of carboxamidofluorscein conjugated to the 5'-end via a hexyl linker and a molecule of tetramethylrhodamine (TAMRA) conjugated at the 3'-end, as described supra.

The effect of MGB conjugation on hybridization between perfectly-matched sequences and sequences containing a single nucleotide mismatch was assessed for 12-mer oligonucleotides in a hydrolyzable probe assay. In each experiment, there were four samples, each containing a different probe. The probes were either fully complementary to the target sequence (i.e., a perfect match) or had a single base mismatch, and either contained or lacked a MGB conjugated at the 3'-end of the oligonucleotide as described infra. The experiment was conducted at an annealing/elongation temperature of 65° C. Oligonucleotides which did not contain a MGB gave baseline levels of fluorescence through 30 cycles of amplification. A MGB-conjugated 12-mer with perfect complementarity to target showed gradually increasing fluorescence from the start of the amplification process, with a significant increase in fluorescence beginning at about the 18th cycle. A MGB-conjugated 12-mer with a single-nucleotide mismatch showed fluorescence levels that were close to baseline, and that were clearly distinguishable from the levels generated by the perfectly matched sequence.

The behavior of 10-mer oligonucleotides with and without a conjugated MGB was also examined at an annealing/elongation temperature of 65° C. With 10-mers, the background was higher and more variable. Nevertheless, while only background signal was obtained when an unconjugated 10-mer was used in the assay (with either a perfect match or a single-nucleotide mismatch), signal obtained using a MGB-conjugated 10-mer with perfect complementarity was readily distinguished from that obtained using a MGB-conjugated 10-mer with a single-base mismatch.

From these results it is clear that conjugation of a MGB to a short oligonucleotide greatly stabilizes the hybrids formed by such conjugated oligonucleotides, compared to oligonucleotides not containing an attached MGB. It should also be noted that, in all cases, the difference in hybrid stability (as evidenced by differences in fluorescence levels at later amplification cycles) between fully complementary probes and probes with a single base mismatch is more pronounced for probes with a conjugated MGB (compared to unconjugated probes), showing that conjugation of a MGB helps to increase the discriminatory power of a short oligonucleotide probe.

Example 3

Effect of Nucleotide Analogues on Hybridization Strength and Discriminatory Ability of MGB-oligonucleotide Conjugates Further increases in discriminatory ability of a MGB-oligonucleotide conjugate are obtained when the conjugate also contains a pyrazolo[3,4-d]pyrimidine nucleotide analogue. In this system, the target sequence is located in the E. coli supF gene contained in the plasmid pSP189 (FIG. 5, SEQ ID No.: 40). See Parris et al. (1992) Gene 117:1-5. Binding sites for the primers used for amplification are indicated as Primer 1 and Primer 2, with Primer 1 having a sequence and polarity that is identical to that shown in FIG. 5, and Primer 2 having a sequence and polarity that is the reverse complement to that shown in FIG. 5. A 15-mer probe, labeled with fluorescein at the 5'-end, and with TAMRA and CDPI$_3$ at the 3'-end, was designed to be complementary to a region within the approximately 375 nucleotides between the primers, as indicated in FIG. 5. This probe was tested using a series of templates, each containing a different single-nucleotide mismatch with the probe sequence, as shown in FIG. 5 and described infra.

```
Primer sequences
The forward amplification primer has the
sequence:
5'-CTGGGTGAGCAAAAACAGGAAGGC-3'    SEQ ID No.: 14

The reverse primer has the sequence:
5'-TGTGATGCTCGTCAGGGGGG-3'         SEQ ID No.: 15

Sequence of probe:
The 15-mer probe has the following sequence:
5'-GGGTTCCCGAGCGGC                  SEQ ID NO.: 16
```

Template Sequences:

The 15-nucleotide region of the template that is complementary to the probe used in this study was modified to generate a series of point mutations, as shown in FIG. 5. Each of the mutant templates was used in a separate assay with the 15-mer probe. The mutant sequences within this region of the template were as follows, with the mismatched nucleotide indicated by bold underling:

```
5'-GGGTTCCCGAGCGGC (perfect match)    SEQ ID NO.: 17

5'-GAGTTCCCGAGCGGC (32 G-A mismatch)  SEQ ID NO.: 18

5'-GGGTTTCCGAGCGGC (36 C-T mismatch)  SEQ ID NO.: 19

5'-GGGTTGCCGAGCGGC (36 C-G mismatch)  SEQ ID NO.: 20

5'-GGGTTACCGAGCGGC (36 C-A mismatch)  SEQ ID NO.: 21

5'-GGGTTCTCGAGCGGC (37 C-T mismatch)  SEQ ID NO.: 22

5'-GGGTTCACGAGCGGC (37 C-A mismatch)  SEQ ID NO.: 23

5'-GGGTTCCCCAGCGGC (39 G-C mismatch)  SEQ ID NO.: 24

5'-GGGTTCCCGTGCGGC (40 A-T mismatch)  SEQ ID NO.: 25

5'-GGGTTCCCGAACGGC (41 G-A mismatch)  SEQ ID NO.: 26

5'-GGGTTCCCGACCGGC (41 G-C mismatch)  SEQ ID NO.: 27

5'-GGGTTCCCGAGCAGC (43 G-A mismatch)  SEQ ID NO.: 28

5'-GGGTTCCCGAGCTGC (43 G-T mismatch)  SEQ ID NO.: 29

5'-GGGTTCCCGAGCGTC (44 G-T mismatch)  SEQ ID NO.: 30
```

The assay was conducted according to Wittwer (1997a,b, supra). FIG. 6 shows that, when a MGB-conjugated 15-mer, additionally having all guanine residues replaced by the guanine analogue 6-amino-1H-pyrazolo[3,4-d]pyrimidin-4 (5H)-one (ppG), is used in an assay in which annealing/elongation temperature is conducted at 75° C., generation of signal by probes with a single-base mismatch is completely suppressed, with no effect on the level of signal generated by the perfectly-matched probe.

Thus, the combination of MGB conjugation, substitution with modified nucleotides and appropriate reaction conditions enable facile discrimination between a perfect-matched hybrid and a hybrid containing a single-nucleotide mismatch, at high stringency, allowing a heretofore unparalleled degree of specificity to be obtained in hybridization reactions with short oligonucleotides.

Example 4

Effects of Base Composition and Oligonucleotide Backbone on Hybrid Stability of MGB-Oligonucleotide Conjugates Materials and Methods Synthesis of Oligonucleotides (ODNs)

All ODNs were prepared from 1 µmol appropriate CPG support on an ABI 394 synthesizer using the protocol supplied by the manufacturer. Protected β-cyanoethyl phosphoramidites of 2'-deoxyribo and 2'-O-methylribonucleotides, CPG supports, deblocking solutions, cap regents, oxidizing solutions and tetrazole solutions were purchased from Glen Research. 5'-Aminohexyl modifications were introduced using an N-(4-monomethoxytrityl)-6-amino-1-hexanol phosphoramidite linker (Glen Research). 3'-Aminohexyl and 3'-hexanol modifications were introduced using the CPG prepared as previously described. Petrie et al. (1992) *Bioconjugate Chem.* 3:85-87. All other general methods employed for preparative HPLC purification, detritylation and butanol precipitation were carried out as described. Reed et al. (1991) *Bioconjugate Chem.* 2:217-225. All purified octanucleotides were analyzed by C-18 HPLC (column 250× 4.6 mm) in a gradient of 0-30% acetonitrile in 0.1 M triethylamine acetate buffer, pH 7.0, over 20 min at a flow rate of 2 ml/min. Pump control and data processing were performed using a Rainin Dynamax chromatographic software package on a Macintosh computer. ODN purity was further confirmed by capillary gel electrophoresis (CGE) with a P/ACE™ 2000 Series equipped with an eCAP™ cartridge (Beckman, Fullerton, Calif.). The octanucleotides were >95% pure by C-18 HPLC and showed one moor peak on CGE. Thermal denaturation studies were performed as described. Lukhtanov et al. (1995) *Bioconjugate Chem.* 6:418-426; Lukhtanov et al. (1996) *Bioconjugate Chem.* 7:564-567. The melting temperatures ($T_{max}$ values) of the hybrids were determined from the first derivative maxima (change in $A_{260}$ with respect to time) and are shown in Tables 7-10.

Synthesis of $CDPI_3$-tailed ODN Conjugates

Methods for conjugation of the 1,2-dihydro-(3H)-pyrrolo [3,2-e]indole-7-carboxylate trimer ($CDPI_3$) to ODNs have been published. Lukhtanov et al. (1995), supra. All ($CDPI_3$)-tailed octanucleotides were isolated from reaction mixtures and, if necessary, repurified on an analytical (4.6×250 mm) PLRP-S column (Polymer Labs) using a gradient of acetonitrile (0-60% for mono- and 0-80% for bis-$CDPI_3$-tailed ODNs) in 0.1 M triethylammonium acetate, pH 7.5. The column was incubated at 70-75° C. All ODN-$CDPI_3$ conjugates prepared were analyzed and characterized as described. Lukhtanov et al. (1995), supra.

Molar Extinction Coefficients of Octanucleotides and their Derivatives

The concentrations of the octanucleotides and their derivatives were measured spectrophotometrically. The molar extinction coefficients ($\epsilon_{260}$) of unmodified octadeoxyribonucleotides were determined by measuring the absorption of the ODNs before and after complete hydrolysis by snake venom nuclease. Shabarova et al. (1981) *Nucleic Acids Res.* 9:5747-5761. With this value, $^{32}$P-labeled $CDPI_3$-tailed conjugates with known specific activities were prepared and their 8260 values determined as described. Lokhov et al. (1992)

*Bioconjugate Chem.* 3:414-419. Molar extinction coefficients of all octadeoxyribonucleotides and their $CDPI_3$ derivatives used in this study are, in order of unmodified ODN, mono-$CDPI_3$ and di-$CDPI_3$ derivative: $d(pT)_8p$, 65.8, 110.1, 178.1/mM/cm; $d(pA)_8p$; 81.9, 150.0, 218.0/mM/cm; d(pApGpCppGpApTpGp), 74.0, 162.9, 230.9/mM/cm; d(pCpApTpCpCpGpCpTp), 65.0, 136.9, 204.9/mM/cm. These extinction coefficients were used to determine the concentration of all other backbone-modified octanucleotides and their $CDPI_3$ conjugates. To calculate $\epsilon_{6260}$ values for deoxyinosine-containing ODNs the value of 4.6/mM/cm multiplied by the number of hypoxanthine bases was subtracted from the extinction coefficients of the corresponding dG-containing ODNs.

Results $CDPI_3$ Residue Conjugated to AT-Rich Duplexes

The antibiotic CC-1065 (Reynolds et al. (1985) *Biochemistry* 24:6228-6237) and its numerous synthetic derivatives (Boger et al. (1995) *Proc. Nail Acad. Sci. USA* 92:3642-3649), including $CDPI_3$, have a strong affinity for AT-rich sites of double-stranded DNA, as do most of the MGBs. CC-1065 also binds to and alkylates AT-rich sequences in RNA-DNA hybrids. Kim et al. (1995) *Antisense Res. Dev.* 5: 149-154. We expected the binding properties of ODN-conjugated $CDPI_3$ to be similar to that observed for free $CDPI_3$. We reported earlier on binding of oligothymidylates carrying a $CDPI_n$ moiety to polyadenylic acids. Lukhtanov et al. (1995, 1996) supra. Here we use the short $d(pT)_8.d(pA)_8$ duplex as a model system for a more comprehensive investigation. NMR analysis of a CC-1065-DNA complex (Scahill et al. (1990) *Biochemistry* 29:2852-2860) and noncompetitive binding of $CDPI_3$ and ethidium bromide to AT-rich DNA duplexes (roger et al. (1992) *J. Org. Chem.* 57:1277-1284) have shown that these compounds span 5-6 base pairs in the DNA minor groove. An octamer duplex, therefore, is a length of double-stranded DNA sufficient to accommodate the conjugated $CDPI_3$ residue and the linkers used in the present study.

A variety of octa-adenylate and octathymidylate derivatives with DNA, 2'-O-methyl RNA or DNA phosphorothioate backbones and carrying $CDPI_3$ residues at either or both termini were prepared. The structures of $CDPI_3$ and linkers for 5'- and 3'-tailed ODN conjugates are shown in FIG. 2. Complementary duplexes constructed from these sequences were melted and the $T_{max}$ data are shown in Table 7. Although the complex strands were taken in equimolar ratio and only single melting transitions were observed in all cases, the possibility of higher order structure formation, other than duplex, cannot be completely excluded. However, a previous study conducted on $d(pT)_8.poly(dA)/poly(rA)$ did not reveal a tendency of $CDPI_3$-tailed ODNs to form triplex structures. Lukhtanov et al. (1995) supra.

As expected, the most dramatic stabilization was achieved for AT duplexes with a regular DNA backbone in both strands. The $T_{max}$ of the weak $d(pT)_8.d(pA)_8$ complex, 12-14° C. under these conditions, was increased to 53-61° C. after one of the strands was conjugated to a MGB. Positioning of the MGB on the duplex gave some strand-specific effects. Location of the $CDPI_3$ moiety on either the 3'- or 5'-end of octathymidylate did not significantly affect duplex stability ($T_{max}$=56 or 58° C.), but did so when conjugated to oligoadenylate sequences. Octa-adenylate carrying the 3'-$CDPI_3$ residue formed the most stable complementary complex ($T_{max}$=61° C.) and the 5'-tailed conjugate the least in this series ($T_{max}$=53° C.).

Table 8 shows two examples of longer DNA duplexes with terminal AT-rich sequences, which were also stabilized by tethered $CDPI_3$ residues. These tetradecanucleotides were designed to test the effect of $CDPI_3$ binding in a region of mixed or alternating AT sequences, as opposed to the $A_8T_8$ homopolymeric sequence above. Conjugation of $CDPI_3$ to the 3'-end of these ODNs increased $T_{max}$ values of the complementary duplexes by 21-22° C. Although this value is half that observed for $d(pT)_8.d(pA)_8$ duplexes (40-49° C.), the overall free energy contribution of the $CDPI_3$ residue was estimated and found to be comparable in both cases. The decrease in $\Delta T_{max}$ was expected, since unmodified hexadecanucleotide duplexes (Table 8) were significantly more stable than $d(pT)_8.d(pA)_8$ ($T_{max}$=48-49 versus 12-14° C.).

Enhancement of nuclease resistance of ODNs by replacement of the phosphodiester group with a phosphorothioate is well established. Eckstein et al. (1970) *Eur. J. Biochem.* 13:558-564; Agrawal et al. (1991) *Proc. Natl. Acad. Sci. USA* 88:7595-7599. This modification generally reduces, however, the affinity of the ODN for a complementary single-stranded target See, for example, Suggs et al. (1985) *Nucleic Acids Res.* 13:5707-5716; Cosstick et al. (1985) *Biochemistry* 24:3630-3638; LaPlanche et al. (1986) *Nucleic Acids Res.* 14:9081-9093; and Stein et al. (1988) *Nucleic Acids Res.* 16:3209-3221. As we found here, $d(PT)_8.d(pA)_8$ duplexes having a phosphorothioate backbone in either the $d(pT)_8$ strand or both strands were significantly destabilized and showed no melting transition over 0° C. (Table 7). The phosphorothioate analog of $d(pA)_8$ formed a weak hybrid with unmodified $d)_8$ ($T_{max}$=8-9° C.). Conjugation of a single $CDPI_3$ residue increased the $T_{max}$ of all these duplexes into a melting range of 35-56° C., a stabilization effect in some cases of >45° C. over the $T_{max}$ of the analogous unmodified complexes. An implication of this finding is that replacement of a phosphate oxygen atom with sulfur does not seem to change the geometry of the minor groove of AT-rich regions, which is still optimal for binding the $CDPI_3$ moiety.

The tethered $CDPI_3$ has almost no effect on RNA.RNA duplexes, which are known to adopt the A-form in aqueous solutions and have a very broad minor groove. For example, addition of a $CDPI_3$ residue to the 3'-end of either strand of a 2'-O-Me-r$(pT)_8$.2'-O-Me-r$(pA)_8$ duplex showed a modest positive effect on $T_{max}$ of 4-9° C. The geometry of RNA.DNA hybrids is somewhere between the A- and B-duplex configurations and both of the 2'-O-Me-RNA.DNA duplexes studied here showed a substantial level of MGB-assisted stabilization, although with some backbone preference. Tethering the MGB residue to the 2'-O-Me-RNA strand was more beneficial, providing an increase in $T_{max}$ of 18° C. for 2'-O-Me-r$(pT)_8.d(pA)_8$ and >21-22° C. for the $d(pT)_8$.2'-O-Me-r$(pA)_8$ duplex. In contrast, a lower effect on stabilization ($\Delta T_{max}$=7° C.) was found when the $CDPI_3$ residue was bound to the $d(pA)_8$ strand. $CDPI_3$-tailed $d(pT)_8$ was unusual in that conjugation of the MGB to the 5'-end of octadeoxythymidylate provided >19° C. stabilization for its duplex with 2'-O-Me-r$(pA)_8$, whereas 3'-$CDPI_3$ had almost no effect on stability of this complex. Good agreement of these data with our previously reported results obtained on poly(rA).d$(pT)_8$ (Lukhtanov et al. (1995, 1996) supra) indicates that addition of a methyl group on a 2'-OH in the minor groove of an RNA.DNA duplex does not substantially alter binding properties of the conjugated $CDPI_3$ residue. Similar results have been obtained for unconjugated CC-1065 bound to AT-rich sites in duplexes with varying backbone structures. Kim et al. (1995) *Antisense Res. Dev.* 5:49-57.

TABLE 7

Melting temperatures (±1° C.) of duplexes formed by octathymidylate and octa-adenylate with different backbone modifications and CDPI₃ residues attached to different ends.

| Octa-adenylate derivatives: | | Octathymidylate derivatives | | | | | 2'-O-Methyl RNA | | Phosphorothioate DNA | |
|---|---|---|---|---|---|---|---|---|---|---|
| Type of backbone | 3'- and 5'-tails[a] | DNA | | | | | | | | |
| | | 3'-HEX | 5'-Hex-NH₂ | 3'-CDPI₃ | 5'-CDPI₃ | 5',3'-di-CDPI₃ | 3'-HEX-OH | 3'-CDPI₃ | 3'-Hex-NH₂ | 3'-CDPI₃ |
| DNA | 3'-Hex-NH₂ | 14 | 12 | 58 | 58 | 55 | 12 | 30 | <0 | 41 |
| | 5'-Hex-NH₂ | 13 | 13 | 58 | 56 | 44 | 10 | 28 | <0 | 42 |
| | 3'-CDPI₃ | 61 | 61 | 71 | 67 | 64 | 19 | 50 | 49 | 61 |
| | 5'-CDPI₃ | 53 | 53 | 63 | 74 | 61 | 17 | 49 | 41 | 56 |
| | 5',3'-di-CDPI₃ | 60 | 57 | 69 | 68 | 71 | — | — | — | — |
| 2'-O-Methyl RNA | 3'-Hex-OH | <0 | <0 | ~0 | 19 | — | 20 | 29 | ND[b] | ND[b] |
| | 3'-CDPI₃ | 22 | 21 | 54 | 58 | — | 24 | 41 | <0 | ND[b] |
| Phosphorothioate DNA | 3'-Hex-NH₂ | 8 | 9 | 55 | 55 | — | 34 | 48 | <0 | 35 |
| | 3'-CDPI₃ | 55 | 56 | 70 | 73 | — | 43 | 65 | 40 | 57 |

[a] The oligonucleotides with this modification have a terminal phosphate linked to the hydroxy group of 1,6-hexanediol (Hex-OH) or 6-amino-1-hexanol (Hex-NH₂) residues. The structure of the CDPI₃ residue and linkers for 3'- and 5'-oligonucleotide conjugates are shown in FIG. 2.
[b] No melting transition detected.

TABLE 8

Structure and stability of tetradecanucleotide duplexes modified by a CDPI₃ residue

| Duplex structure | 3'-Tail | $T_{max}$ (° C. ± 1° C.) |
|---|---|---|
| 5'-d(GpTpGpTpGpTpCpApTpApTpApTpAp)-X-3' (SEQ ID No.: 31) | X = —O(CH₂)₆NH₂ | 48 |
| NH₂(CH₂)₆O-d(pCpApCpApCpApGpTpApTpApTpApT)-5' (SEQ ID No.: 32) | X = —O(CH₂)₆NH—CDPI₃ | 69 |
| 5'-d(GpTpGpTpGpTpCpApTpApApApTpAp)-X-3' (SEQ ID No.: 33) | X = —O(CH₂)₆NH₂ | 49 |
| 3'-d(CpApCpApCpApGpTpApTpTpTpApT)-5' (SEQ ID NO: 34) | X = —O(CH₂)₆NH—CDPI₃. | 71 |

TABLE 9

Melting temperatures (±1° C.) of GC-rich octanucleotide duplexes with CDPI₃ residues attached to the ends

| | | ApGpCpGpGpApTpG (strand B) | | | | | | | | | |
|---|---|---|---|---|---|---|---|---|---|---|---|
| CpApTpCpCpGpCpT (strand A) | | | | | | | 2'-O-Methyl RNA | | Phosphorothioate DNA | | |
| Type of backbone: | 3'- and 5'-tails[a]: | DNA | | | | | 5'-CPDI₃ and 3'-Hex-OH | 3'-CDPI₃ | Unmodified[b] | 5'-CDPI₃ | 3'-CDPI₃ |
| | | 3'-Hex-NH₂ | 5'-CDPI₃ | 3'-CDPI₃ | 5',3'-di-CDPI₃ | 3'-HEX-OH | | | | | |
| DNA | 3'-Hex-NH₂ | 41 | 45 | 52 | 50 | 46 | 48 | 47 | 33 | 27 | 40 |
| | 5'-CDPI₃ | 58 | 76 | 79 | 76 | 52 | 71 | 80 | 49 | 70 | 75 |
| | 3'-CDPI₃ | 57 | 78 | 81 | 77 | 51 | 68 | 72 | 50 | 73 | 77 |
| | 3',5'-di-CDPI₃ | 60 | BT[d] | 72 | 65 | — | — | — | — | — | — |
| 2'-O-Methyl RNA | 3'-Hex-OH | 37 | 20 | 29 | — | 66 | 67 | 67 | 28 | ND[c] | ND[c] |
| | 5'-CDPI₃ and 3'-Hex-OH | 44 | 69 | 70 | — | 68 | ~95 | 87 | 41 | 58 | 64 |
| | 3'-CDPI₃ | 44 | 71 | BT[d] | — | 72 | 90 | 82 | 37 | 58 | 40 |

TABLE 9-continued

Melting temperatures (±1° C.) of GC-rich octanucleotide duplexes with CDPI₃ residues attached to the ends

| | | ApGpCpGpGpApTpG (strand B) | | | | | | | | | |
|---|---|---|---|---|---|---|---|---|---|---|---|
| CpApTpCpCpGpCpT (strand A) | | | | | | 2'-O-Methyl RNA | | | | | |
| | | DNA | | | | 5'-CPDI₃ | | | Phosphorothioate DNA | | |
| Type of backbone: | 3'- and 5'-tails[a]: | 3'-Hex-NH₂ | 5'-CDPI₃ | 3'-CDPI₃ | 5',3'-di-CDPI₃ | 3'-HEX-OH | and 3'-Hex-OH | 3-CDPI₃ | Unmodified[b] | 5'-CDPI₃ | 3'-CDPI₃ |
| Phosphorothioate | Unmodified[b] | 32 | 32 | 43 | — | 38 | 43 | 39 | 24 | 16 | 28 |
| | 5'-CDPI₃ | 38 | 67 | 69 | — | 38 | 64 | 66 | 28 | 62 | 63 |
| DNA | 3'-CDPI₃ | 45 | 71 | 74 | — | 44 | 75 | 53 | 36 | 64 | 69 |

[a]Structures of the CDPI₃ residue and linkers for 3'- and 5'-oligonucleotide conjugates are shown in FIG. 2.
[b]These ODNs have no tails.
[c]No melting transition was detected.
[d]Melting transition was too broad for $T_{max}$ to be accurately determined.

Effect of Addition of a MGB Residue to a GC-rich Octanucleotide Duplex

It is well recognized that A/T preference dominates the binding specificity of most MGBs, including CDPI oligomers. This preference is likely due to the hydrophobicity, depth and narrow width of the groove. Together these provide a perfect isohelical and van der Waals fit of the crescent-shaped MGB molecules in the minor groove. Free CDPI₃ was shown to bind not only to poly(dA).poly(dT) but also to poly(dG).poly(dC), although with a lower strength. Boger et al. (1992) *J. Org. Chem.* 57:1277-1284. Therefore, it was interesting to investigate the ability of the CDPI₃ residue to stabilize short GC-rich and mixed duplexes. Table 9 shows the effect of the same MGB modifications discussed above on GC-rich octanucleotide duplexes, in which the nature of the minor groove is altered. The test sequence, with a 3'-hexylamino tail, gave a duplex $T_{max}$ of 41° C. Addition of a single MGB to either end of strand A increased the $T_{max}$ by 16-17° C., while addition to strand B gave a smaller increase in $T_{max}$ ($\Delta T_{max}$=4-11° C.). Strand B showed a preference for the position of CDPI₃ conjugation, with its 3'-CDPI₃-tailed conjugate forming a more stable duplex ($T_{max}$=52° C.) than its corresponding 5'-CDPI₃ derivative ($T_{max}$=45° C.). This effect was seen for all of the other duplexes presented in Table 9 (except when strand B has a 2'-O-methyl backbone) and could be due to the presence of the two AT pairs in the test sequence proximal to the site of conjugation of the MGB.

Addition of the 2'-O-methyl modification (Table 9) to both strands gave a 25° C. increase in $T_{max}$ over the 2'-deoxy strands. This has previously been shown to be a stabilizing modification. Inoue et al. (1987) *Nucleic Acids Res.* 15:6131-6148. A single MGB tethered to strand B did not change the $T_{max}$ and addition to strand A gave a modest increase ($\Delta T_{max}$=2-6° C.). Hybrids between one strand bearing the 2'-O-methyl modification and one with a DNA backbone were similar to those of an unmodified DNA duplex ($T_{max}$=41° C.), with duplex stability lower when strand A was 2'-O-methyl ($T_{max}$=37° C.) and higher when strand B was 2'-O-methyl ($T_{max}$=46° C.). Interestingly, CDPI₃ conjugation destabilized the former of these duplexes. This effect was observed for both 3'-($T_{max}$=29° C.) and 5'-CDPI₃-tailed ($T_{max}$=20° C.) derivatives of strand B (the DNA strand). This destabilizing effect was exacerbated by phosphorothioate modification of strand B. In both cases, no detectable melting transition over 0° C. was detected, compared with a $T_{max}$ of 28° C. for the non-conjugated counterpart.

Conversion of both backbones of the DNA octameric duplex to all phosphorothioate linkages reduced the $T_{max}$ by 17° C. (from 41° C. to 24° C.). Addition of a single MGB to strand B gave little change in $T_{max}$ (even a decrease of 8° C. in the 5'-CDPI₃ case) and addition to strand A gave a modest increase of 4-12° C. In general, phosphorothioate analogs of strands A and B demonstrated hybridization properties similar to those observed for phosphodiester ODNs except that all of their complementary complexes have lower $T_{max}$.

The conjugated CDPI₃ residue stabilized GC-rich DNA duplexes, with the extent of stabilization being about half, in terms of enhancement of $T_{max}$, of that observed for the d(pT)₈.d(pA)₈ complex. In contrast, another type of conjugated MGB, N-methylpyrrole carboxamide (MPC) oligomers, failed to stabilize the same GC-rich octadeoxyribonucleotide duplex used in this study. Sinyakov et al. (1995) *J. Am. Chem. Soc.* 117:4995-4996. Without wishing to be bound by theory, CDPI₃ may be less sensitive to the structure of the minor groove of a duplex than the netropsin-type MPC peptides, because it does not form any hydrogen bonds with the bases and therefore the interaction is driven by van der Waals contacts or hydrophobic forces. A narrower minor groove may promote better CDPI₃ binding and hence greater duplex stabilization.

CDPI₃-conjugated Duplexes Containing Deoxyinosine in Place of Deoxyguanosine

Substitution of deoxyguanosine (dG) by deoxyinosine (dI) in the modified ODN could create a minor groove environment more suitable for CDPI₃ binding, as was observed for netropsin and Hoechst 33258 (44). Nielsen (1991) *Bioconjugate Chem.* 2:1-12; Wartell et al. (1974) *J. Biol. Chem.* 249: 6719-6731; Marck et al. (1982) *Nucleic Acids Res.* 10:6147-6161; and Moon et al. (1996) *Biopolymers* 38:593-606. dI-containing analogues of the GC-rich duplex were prepared and studied with respect to MGB-assisted stabilization (Table 10). Replacement of the single dG of strand A with a dI residue gave a 10° C. decrease in $T_{max}$. Addition of a single MGB to the 3'-end of either strand of this complex raised the $T_{max}$ to a value 7-13° C. higher than the parent dG-containing duplex.

The effect of the tethered MGB on the duplex containing four dI residues in strand B was dramatic. The duplex formed between this modified strand B and either the native or dI-substituted analog of strand A was weak ($T_{max}$=11° C. for native strand A) or nonexistent (for dI-substituted strand A). Addition of the MGB to the 3'-end of strand A raised the $T_{max}$ from 11° C. to 48° C.; while addition of a MGB to the 3'-end of strand B raised the $T_{max}$ from essentially 0° C. to 41° C. These values represent a 37-48° C. increase in $T_{max}$ due to conjugation of a MGB to oligonucleotides forming duplexes containing dI.dC base pairs, which is close to the stability of the analogous dG-containing native strands. This shows that the conjugated $CDPI_3$ residue stabilizes dIdC-rich sequences as well as those rich in dAdT.

Duplexes with two or More Conjugated $CDPI_3$ Residues

The ability of the minor groove of double-stranded DNA to bind two MGB residues in a side-by-side antiparallel orientation has been noted. Kubista et al. (1987) *Biochemistry* 26:4545-4553; Mohan et al. (1992) *J. Biomol. Struct. Dyn.* 9:695-704; Fagan et al. (1992) *J. Am. Chem. Soc.* 114:1080-1081; Mrksich et al. (1992) *Proc. Natl. Acad. Sci. USA* 89:7586-7590; and Chen et al. (1994) *J. Am. Chem. Soc.* 116:6995-7005. Side-by-side binding of two MGB moieties in the duplex minor groove affords hyperstabilization in all duplexes studied which carry two $CDPI_3$ residues tethered to opposite strands (Tables 7 and 9). For example, a $d(pT)_8.d(pA)_8$ duplex, already stabilized by 40-49° C. by one conjugated $CDPI_3$ residue, was further stabilized by an additional 5-18° C. to reach a $T_{max}$ of 74° C. for $d(pT)_8.d(pA)_8$ (Table 7). This is unprecedented for short duplexes with a phosphodiesler backbone. The greatest stabilization occurred when either the 5'- or 3'-end of both strands was modified with an MGB; these could bind in the minor groove in an antiparallel mode ($T_{max}$=71 and 74° C.). The parallel orientation was less beneficial ($T_{max}$=63 and 67° C.). This is consistent with literature data for 'free' MGBs in which only the antiparallel orientation was experimentally observed. Mohan, supra; Fagan, supra; Mrksich, supra; and Animati et al. (1995) *J. Med. Chem.* 38:1140-1149.

This hyperstabilization did not seem to depend on either sequence or backbone modification. All AT- and GC-rich duplexes that contained two MGB residues, with one conjugated to each of the opposite strands, were substantially stabilized compared with analogous duplexes bearing a single $CDPI_3$ tail (Tables 7 and 9). For example, Table 7 shows that complexes formed by phosphorothioate analogs of $d(pT)_8$ and/or $d(pA)_8$ possessing two $CDPI_3$ residues showed a $T_{max}$ in the same range ($T_{max}$=56-73° C.) as their phosphodiester counterparts ($T_{max}$=63-74° C.). Addition of a MGB to both strands of a duplex with 2'-O-methyl modifications increased the stability by 21° C. (from 20° C. to 41° C., Table 7). In the case of GC-rich duplexes, the stabilization resulting from conjugation of a second $CDPI_3$ residue to an opposite duplex strand was even greater than that observed for the first $CDPI_3$ incorporation. For instance, attachment of one $CDPI_3$ residue increased stability of the GC DNA duplex by 4-17° C. and addition of the second $CDPI_3$ moiety contributed 18-33° C. to $T_{max}$.

The data on duplexes with multiple conjugated MGBs in Tables 7 and 9 show the following trends. If the duplex bore two $CDPI_3$ residues tethered to the same strand at the 3'- and 5'-ends almost no advantage in stability versus the corresponding mono-$CDPI_3$-tailed duplex was seen. This implies a strong hydrophobic interaction between two $CDPI_3$ residues occupying the same site in the minor groove of a short duplex. Furthermore, additional binding between the two MGB moieties attached to the opposite duplex strands appears to add significantly to hybrid stability. Similar effects of interaction of pendant hydrophobic groups on duplex and triplex stabilization were seen with ODNs conjugated to cholesterol residues. Gryaznov et al. (1993) *Nucleic Acids Res.* 21:5909-5915. Addition of third and fourth $CDPI_3$ conjugated residues normally had no or a slightly negative effect on stability of the GC-rich duplexes studied (Table 9).

TABLE 10

Melting temperatures (±1° C.) of dG- and dI-containing octanucleotide duplexes carrying a 3'-$CDPI_3$ residue

| | | Strand B | | | |
|---|---|---|---|---|---|
| | | d(AGCGGATG)p | | d(AICIIATT)p | |
| Strand A: | 3'-Tails[a] | 3'-Hex-$NH_2$ | 3'-$CDPI_3$ | 3'-Hex-$NH_2$ | 3'-$CDPI_3$ |
| d(CATCCGCT)p | 3'-Hex-$NH_2$ | 41 | 52 | 11 | — |
| | 3'-$CDPI_3$ | 57 | 81 | 48 | 67 |
| d(CATCCICT)p | 3'-Hex-$NH_2$ | 31 | 48 | ~0 | 41 |
| | 3'-$CDPI_3$ | 54 | 79 | 48 | 63 |

[a]Structures of the $CDPI_3$ residue and linker for the conjugates are shown in FIG. 1.

Example 5

Reduced Dependence of $T_m$ on Base Composition of MGB-oligonucleotide Conjugates Short oligonucleotides of differing A+T content, conjugated to a MGB, were used to investigate the effect of base composition on $T_m$ for MGB-short oligonucleotide conjugates (Table 11). $T_m$s were determined on a Perkin Elmer λ2S UV/VIS spectrophotometer, equipped with a PTP-6 temperature controller, using the PECSS software package. The A+T content of the oligonucleotides tested ranged from 12.5% to 100% and $T_m$ was determined for the hybrid of each of the oligonucleotides with its exact complement. As shown in Table 11, 8-mer MGB-oligonucleotide conjugates with A+T contents between 37.5% and 100% had $T_m$s that ranged between 45-54° C., a 9-degree span; while the $T_m$s for unconjugated 8-mers having similar A+T contents ranged over 38° C.

Other experiments have shown that, for 7-mers, $T_m$s of oligonucleotides with A+T contents between 28% and 100% varied over a range of only 4.4° C. These results and those shown in Table 11 suggest that, for short oligonucleotides conjugated to a MGB, $T_m$ is more closely related to length than to base composition.

In addition, the range of $T_m$ values for MGB-conjugated 8-mers extends from 45° C., for oligonucleotides having a base composition of 100% A+T, to 63° C., for 0% A+T. Thus, the $T_m$ values for MGB-conjugated 8-mers range over approximately 18° C. By comparison, the $T_m$ range for unconjugated 8-mers (between 0 and 100% A+T) encompasses at least 52° C. (Table 11). There is therefore a clear trend toward lessening of the differences in $T_m$ between short oligonucleotides of different base compositions, when such short oligonucleotides are conjugated to a MGB.

Example 6

Retention of Mismatch Discriminatory Capability of a Short Oligonucleotide Conjugated to a MGB Although the dependence of $T_m$ on base composition is suppressed for short, 8-mer oligonucleotides that are conjugated to a MGB; their heightened discriminatory ability, compared to unconjugated oligonucleotides, is retained. Table 12 shows examples of $T_m$ determinations for an 8-mer MGB-conjugated oligonucleotide hybridized to a perfectly-matched sequence and to four other sequences, each containing a different single-nucleotide mismatch. The minimum difference in $T_m$ between a perfect match and a single-nucleotide mismatch is 19° C., while the maximum difference is 41° C.

TABLE 11

Effect of MGB conjugation on $T_m$ values of 8-mer MGB-oligonucleotide conjugates with varying A + T content

| Sequence | $T_m$ +MGB | $T_m$ −MGB |
|---|---|---|
| 5'-MGB-CAGCGGCG | 63 | 52 |
| 5'-MGB-CAGCGACG | 53 | 45 |
| 5'-MGB-CAGTGACG | 49 | 38 |
| 5'-MGB-CAGTGACA | 47 | 33 |
| 5'-MGB-CAITIACA | 53 | 17 |
| 5'-MGB-CAATGACA | 54 | 27 |
| 5'-MGB-CAATGATA | 45 | 20 |
| 5'-MGB-CAATAATA | 45 | 12 |
| 5'-MGB-TAATAATA | 45 | <0 |

TABLE 12

Mismatch discrimination by 8-mer MGB-oligonucleotide conjugates

| Sequence | | $T_m$ |
|---|---|---|
| 5'-TTTTGTCACTGTTT ACAGTGAC-MGB-5' | (SEQ ID NO.:35) | 47 |
| 5'-TTTTGTCATTGTTT ACAGTGAC-MGB-5' | (SEQ ID NO.:36) | 20 |
| 5'-TTTTGTTACTGTTT ACAGTGAC-MGB-5' | (SEQ ID NO.:37) | 25 |
| 5'-TTTTGACACTGTTT ACAGTGAC-MGB-5' | (SEQ ID NO.:38) | 28 |
| 5'-TTTTATCACTGTTT ACAGTGAC-MGB-5' | (SEQ ID NO.:39) | 6 |

While the foregoing invention has been described in some detail by way of illustration and example for purposes of clarity of understanding, it will be apparent to those skilled in the art that various changes and modifications may be practiced without departing from the spirit of the invention. Therefore the foregoing descriptions and examples should not be construed as limiting the scope of the invention.

What is claimed is:

1. An oligonucleotide probe comprising a 5'-end, a 3'-end and one or more detectable labels, wherein the probe is a MGB-oligonucleotide conjugate, wherein the MGB is a molecule having a molecular weight of approximately 150 to approximately 2,000 Daltons that binds into the minor groove of a double-stranded nucleic acid with an association constant of greater than approximately $10^3$ $M^{-1}$.

2. The probe according to claim 1, wherein said MGB is a radical of a compound selected from the group consisting of netropsin, distamycin and lexitropsin, mithramycin, chromomycin A3, olivomycin, anthramycin, sibiromycin, diarylamidines, pentamidine, stilbamidine, berenil, CC-1065, pyrroloindole, indole polypeptides, Hoechst 33258, and 4'-6-diamino-2-phenylindole.

3. The probe according to claim 1, wherein MGB is crescent shaped.

4. The probe according to claim 1, wherein MGB is selected from the group consisting of a dimer of 1,2-dihydro-(3H)-pyrrolo[3,2-e]indole-7-carboxylate ($CDPI_2$), a trimer of 1,2-dihydro-(3H)-pyrrolo[3,2-e]indole-7-carboxylate ($CDPI_3$), tetramer of 1,2-dihydro-(3H)-pyrrolo[3,2-e]indole-7-carboxylate ($CDPI_4$) and a pentamer of N-methylpyrrole-4-carbox-2-amide ($MPC_5$).

5. The probe according to claim 1, wherein said MGB is an analog of a compound selected from the group consisting of netropsin, distamycin and lexitropsin, mithramycin, chromomycin A3, olivomycin, anthramycin, sibiromycin, diarylamidines, pentamidine, stilbamidine, berenil, CC-1065, pyrroloindole, indole polypeptides, Hoechst 33258, and 4'-6-diamino-2-phenylindole.

* * * * *

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (xi) SEQUENCE DESCRIPTION: SEQ ID NO: 1:

ATAAAACAGA GGTGAG                                          16

(2) INFORMATION FOR SEQ ID NO: 2:

(i) SEQUENCE CHARACTERISTICS:
       (A) LENGTH: 12 base pairs
       (B) TYPE: nucleic acid
       (C) STRANDEDNESS: single
       (D) TOPOLOGY: linear (xi) SEQUENCE DESCRIPTION: SEQ ID NO: 2:

ATAAAACAGA GG                                              12

(2) INFORMATION FOR SEQ ID NO: 3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 3:

ATAAAACAGA                                                              10

(2) INFORMATION FOR SEQ ID NO: 4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 4:

TAATAACGTT CGGGCA                                                       16

(2) INFORMATION FOR SEQ ID NO: 5:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO: 5:

ATAACG                                                                   6

(2) INFORMATION FOR SEQ ID NO: 6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 6:

TAATAACGTT CG                                                           12

(2) INFORMATION FOR SEQ ID NO: 7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 7:

TAATAACGTT                                                              10

(2) INFORMATION FOR SEQ ID NO: 8:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (xi) SEQUENCE DESCRIPTION: SEQ ID NO: 8:

CGGGCAAA                                                                 8

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 9:

CGGGCAAAGG ATTTAA                                                      16

(2) INFORMATION FOR SEQ ID NO: 10:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO: 10:

GGCAAA                                                                         6

(2) INFORMATION FOR SEQ ID NO: 11:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (xi) SEQUENCE DESCRIPTION: SEQ ID NO: 11:

CGGCTCTA                                                                     8

(2) INFORMATION FOR SEQ ID NO: 12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 12:

CGGCTCTAAT CTATTA                                                   16

(2) INFORMATION FOR SEQ ID NO: 13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 13:

TATTTTAGAT AACCTT                                                   16

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 14:

CTGGGTGAGC AAAAACAGGA AGGC                                  24

```
(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 15:

TGTGATGCTC GTCAGGGGGG                                               20

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 16:

GGGTTCCCGA GCGGC                                                    15

(2) INFORMATION FOR SEQ ID NO: 17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 17:

GGGTTCCCGA GCGGC                                                    15

(2) INFORMATION FOR SEQ ID NO: 18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 18:

GAGTTCCCGA GCGGC                                                    15

(2) INFORMATION FOR SEQ ID NO: 19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 19:

GGGTTTCCGA GCGGC                                                    15

(2) INFORMATION FOR SEQ ID NO: 20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 20:

GGGTTGCCGA GCGGC                                                    15
```

-continued (2) INFORMATION FOR SEQ ID NO: 21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 21:

GGGTTACCGA GCGGC                                                      15

(2) INFORMATION FOR SEQ ID NO: 22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 22:

GGGTTCTCGA GCGGC                                                      15

(2) INFORMATION FOR SEQ ID NO: 23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 23:

GGGTTCACGA GCGGC                                                      15

(2) INFORMATION FOR SEQ ID NO: 24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 24:

GGGTTCCCCA GCGGC                                                      15

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 25:

GGGTTCCCGT GCGGC                                                      15

(2) INFORMATION FOR SEQ ID NO: 26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 26:

GGGTTCCCGA ACGGC                                                      15

(2) INFORMATION FOR SEQ ID NO: 27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 27:

GGGTTCCCGA CCGGC         15

(2) INFORMATION FOR SEQ ID NO: 28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 28:

GGGTTCCCGA GCAGC         15

(2) INFORMATION FOR SEQ ID NO: 29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 29:

GGGTTCCCGA GCTGC         15

(2) INFORMATION FOR SEQ ID NO: 30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 30:

GGGTTCCCGA GCGTC         15

(2) INFORMATION FOR SEQ ID NO: 31:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 31:

GTGTGTCATA TATA         14

(2) INFORMATION FOR SEQ ID NO: 32:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 32:

TATATATGAC ACAC         14

-continued (2) INFORMATION FOR SEQ ID NO: 33:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 33:

GTGTGTCATA AATA                                          14

(2) INFORMATION FOR SEQ ID NO: 34:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 34:

TATTTATGAC ACAC                                          14

(2) INFORMATION FOR SEQ ID NO: 35:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 35:

TTTTGTCACT GTTT                                          14

(2) INFORMATION FOR SEQ ID NO: 36:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 36:

TTTTGTCATT GTTT                                          14

(2) INFORMATION FOR SEQ ID NO: 37:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 37:

TTTTGTTACT GTTT                                          14

(2) INFORMATION FOR SEQ ID NO: 38:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 38:

TTTTGACACT GTTT                                          14

```
(2) INFORMATION FOR SEQ ID NO: 39:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 39:

TTTTATCACT GTTT                                                             14

(2) INFORMATION FOR SEQ ID NO: 40:

(i) SEQUENCE CHARACTERISTICS:
        (A) LENGTH: 510 base pairs
        (B) TYPE: nucleic acid
        (C) STRANDEDNESS: single
        (D) TOPOLOGY: linear (xi) SEQUENCE DESCRIPTION: SEQ ID NO: 40:

AAAACTCTCA AGGATCTTAC CGCTGTTGAG ATCCAGTTCG ATGTAACCCA CTCGTGCACC            60

CAACTGATCT TCAGCATCTT TTACTTTCAC CAGCGTTTCT GGGTGAGCAA AAACAGGAAG           120

GCAAAATGCC GCAAAAAAGG GAATAAGGGC GACACGGAAA TGTTGAATAC TCATACTCTT           180

CCTTTTTCAA TATTATTGAA GCATTTATCA GGGAATTCGA GAGCCCTGCT CGAGCTGTGG           240

TGGGGTTCCC GAGCGGCCAA AGGGAGCAGA CTCTAAATCT GCCGTCATCG ACTTCGAAGG           300

TTCGAATCCT TCCCCCACCA CCACGGCCGA AATTCGGTAC CCGGATCCTT AGCGAAAGCT           360

AAGATTTTTT TTACGCGTGA GCTCGACTGA CTCCNNNNNN NNGAGCTCAA TTCGGTCGAG           420

GTCGGGCCGC GTTGCTGGCG TTTTTCCATA GGCTCCGCCC CCTGACGAG CATCACAAAA           480

ATCGACGCTC AAGTCAGAGG TGGCGAAACC                                           510
```